US007977342B2

(12) United States Patent
Simmen et al.

(10) Patent No.: US 7,977,342 B2
(45) Date of Patent: Jul. 12, 2011

(54) HCV INHIBITING BI-CYCLIC PYRIMIDINES

(75) Inventors: Kenneth Alan Simmen, Tervuren (BE); Tse-I Lin, Mechelen (BE); Oliver Lenz, Sint-Katelijne-Waver (BE); Dominique Louis Nestor Ghislain Surleraux, Braine-le-château (BE); Pierre Jean-Marie Bernard Raboisson, Sterrebeek (BE)

(73) Assignee: Tibotec-Virco Virology BVBA, Turnhoutseweg (BE)

( * ) Notice: Subject to any disclaimer, the term of this patent is extended or adjusted under 35 U.S.C. 154(b) by 0 days.

(21) Appl. No.: 11/684,288

(22) Filed: Mar. 9, 2007

(65) Prior Publication Data
US 2007/0155716 A1 Jul. 5, 2007

(51) Int. Cl.
A01N 43/54 (2006.01)
A01N 43/90 (2006.01)
A61K 31/517 (2006.01)
A61K 31/519 (2006.01)
(52) U.S. Cl. .................. 514/258.1; 514/260.1
(58) Field of Classification Search .................. None
See application file for complete search history.

(56) References Cited

U.S. PATENT DOCUMENTS

| 6,476,031 | B1 | 11/2002 | Chakravarty et al. |
| 2004/0038856 | A1 | 2/2004 | Chakravarty et al. |
| 2008/0182863 | A1 | 7/2008 | Simmen et al. |
| 2009/0131460 | A1 | 5/2009 | Simmen et al. |
| 2009/0156595 | A1 | 6/2009 | Raboisson et al. |

FOREIGN PATENT DOCUMENTS

| GB | 2295387 | * | 5/1996 |
| WO | WO 00/12497 A2 | | 3/2000 |
| WO | WO 01/47921 A1 | | 7/2001 |
| WO | WO 02/22601 A1 | | 3/2002 |
| WO | WO 02/076976 A2 | | 10/2002 |
| WO | WO 03/077921 A1 | | 9/2003 |
| WO | WO 03/078423 A1 | | 9/2003 |
| WO | WO 03/078426 A1 | | 9/2003 |
| WO | WO 03/078427 A1 | | 9/2003 |
| WO | WO 03/097615 A1 | | 11/2003 |
| WO | WO 2004/047818 A2 | | 6/2004 |
| WO | WO 2004/048930 A2 | | 6/2004 |
| WO | WO 2004/065392 A | | 8/2004 |
| WO | WO 2004/074270 A2 | | 9/2004 |
| WO | WO 2004/087056 A | | 10/2004 |
| WO | WO 2005/032481 A2 | | 4/2005 |
| WO | WO 2006/100310 A1 | | 9/2006 |
| WO | WO 2006/105063 A1 | | 10/2006 |

OTHER PUBLICATIONS

Dorwald F. A. Side Reactions in Organic Synthesis, 2005, Wiley: VCH, Weinheim p. IX of Preface.*
Kimura, et. al., Journal of Infectious Diseases, (2006); 193, 1371-4.*
Choo, Qui-Lim et al., "Isolation of a cDNA Clone Derived from a Blood-Borne Non-A, Non-B Viral Hepatitis Genome", Science, Apr. 21, 1989, pp. 359-362, vol. 244.
Cooper, Kelvin et al., "Bicyclo[3.3.0]octenones in Synthesis. An Approach to the Synthesis of the Antitumor Sesquiterpene Quadrone", J. Chem. Soc. Perkin Trans., 1984, pp. 799-809, vol. 1.
Dowd, Paul et al., "Free Radical Ring-Expansion Leading to Novel Six- and Seven-Membered Heterocycles", Tetrahedron, 1991, pp. 4847-4860, vol. 47, No. 27.
Goodman & Gilman's the Pharmacological Basis of Therapeutics.
Greco, Michael N. et al., "Highly Stereoselective Synthesis of Substituted Hydrindanes Related to the Antiepileptic Drug Topiramate", Tetrahedron Letters, 1992, pp. 5009-5012, vol. 33, No. 35.
Kim, W. Ray, "The Burden of Hepatitis C in the United States", Hepatology, 2002, pp. 530-534, vol. 36, No. 5, Suppl. 1.
Kolykhalov, Alexander A. et al., "Hepatitis C Virus-Encoded Enzymatic Activities and Conserved RNA Elements in the 3' Nontranslated Region Are Essential for Virus Replication In Vivo", Journal of Virology, Feb. 2000, pp. 2046-2051, vol. 74, No. 4.
Krieger, Nicole et al., "Enhancement of Hepatitis C Virus RNA Replication by Cell Culture-Adaptive Mutations", Journal of Virology, May 2001, pp. 4614-4624, vol. 75, No. 10.
Lauer, Georg M. et al., "Hepatitis C Virus Infection", New Engl. J. Med., Jul. 5, 2001, pp. 41-52, vol. 345, No. 1.
Lohmann, V. et al., "Replication of Subgenomic Hepatitis C Virus RNAs in a Hepatoma Cell Line", Science, Jul. 2, 1999, pp. 110-113, vol. 285.
Moyer, Mikel P. et al., Intramolecular N-H, O-H and S-H Insertion Reactions. Synthesis of Heterocycles from α-Diazo β-Keto Esters, J. Org. Chem., 198, pp. 5223-5230, vol. 50, year issued: 1985.
National Institutes of Health Consensus Development Conference Statement: Management of Hepatitis C: 2002-Jun. 10-12, 2002, Hepatology, Nov. 2002, pp. S3-S-20.
Wolff, Manfred E. et al., Thia Steroids. III. Derivatives of 2-Thia-A-nor-5α-androstan-17β-ol As Probes of Steroid-Receptor Interactions, Journal of Medicinal Chemistry, 1970, pp. 531-534, vol. 13, No. 3.
In the U.S. Patent and Trademark Office, Final Office Action in re: U.S. Appl. No. 11/914,044 dated Apr. 29, 2010, 7 pages.
In the U.S. Patent and Trademark Office, Non-Final Office Action in re: U.S. Appl. No. 11/914,044 dated Sep. 3, 2009, 11 pages.
In the U.S. Patent and Trademark Office, Final Office Action in re: U.S. Appl. No. 11/909,118 dated Jul. 13, 2009, 11 pages.
In the U.S. Patent and Trademark Office, Non-Final Office Action in re: U.S. Appl. No. 11/909,118 dated Dec. 30, 2008, 15 pages.
Murata et al., "Suppression of Hepatitis C Virus Replicon by TGF-β," *Virology*, 331: 407-417, 2005.

(Continued)

*Primary Examiner* — James O Wilson
*Assistant Examiner* — Jeffrey H Murray

(57) ABSTRACT

The present invention relates to the use of bi-cyclic pyrimidines as inhibitors of HCV replication as well as their use in pharmaceutical compositions aimed to treat or combat HCV infections. In addition, the present invention relates to processes for preparation of such pharmaceutical compositions. The present invention also concerns combinations of the present bi-cyclic pyrimidines with other anti-HCV agents.

9 Claims, No Drawings

OTHER PUBLICATIONS

Valentino J. Stella, "Prodrugs as Therapeutics," *Expert Opinion on Therapeutic Patents*, 14(3): 277-280, 2004.

Manfred E. Wolff, "Some Considerations for Prodrug Design," *Burger's Medicinal Chemistry and Drug Discovery*, 5th Ed., vol. 1, 975-977, 1994.

Bernard Testa, "Prodrug Research: Futile or Fertile?" *Biochemical Pharmacology* 68: 2097-2106, 2004.

Ettmayer et al., "Lessons Learned from Marketed and Investigational Prodrugs," *Journal of Medicinal Chemistry*, 47(10): 2393-2404, 2004.

* cited by examiner

HCV INHIBITING BI-CYCLIC PYRIMIDINES

CROSS REFERENCE TO RELATED APPLICATIONS

This application claims priority from PCT/EP2005/054912, filed Sep. 29, 2005, which claims priority to EP Application No. 05102810.8, filed Apr. 8, 2005, which claims priority from EP Application No. 04104815.8, filed Sep. 30, 2004. The complete disclosures of the aforementioned related patent applications are hereby incorporated herein by reference in their entirety and for all purposes.

BACKGROUND

The present invention relates to the use of bi-cyclic pyrimidines as inhibitors of HCV replication as well as their use in pharmaceutical compositions aimed to treat or combat HCV infections. In addition, the present invention relates to processes for preparation of such pharmaceutical compositions. The present invention also concerns combinations of the present bi-cyclic pyrimidines with other anti-HCV agents.

Following its discovery in 1989 as the agent implicated in the majority of viral non-A, non-B hepatitis (Choo et al., Science 244, 359-362, 1989), hepatitis C virus (HCV) has become a focus of considerable medical research (Lauer, G. M and Walker, B. D., New Eng. J Med. 345, 41-52, 2001). HCV is a member of the Flaviviridae family of viruses in the hepacivirus genus, and is closely related to the flavivirus genus, which includes a number of viruses implicated in human disease, such as dengue virus and yellow fever virus, and to the animal pest virus family, which includes bovine viral diarrhea virus (BVDV). HCV is a positive-sense, single-stranded RNA virus, with a genome of around 9,600 bp. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and post-translational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA in chimpanzee models of infection (Kolykhalov, A. A., Mihalik, K., Feinstone, S. M., and Rice, C. M. J Virol. 74, 2046-2051, 2000). In addition to the NS3 serine protease, HCV also encodes a metalloproteinase in the NS2 region.

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus (HCV). Following the initial acute infection, a majority of infected individuals develop chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. Hepatology, 36, 5 Suppl. S3-S20, 2002). Liver cirrhosis due to HCV infection is responsible for about 10,000 deaths per year in the U.S.A. alone, and is the leading cause for liver transplantations. Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades (Kim, W. R. Hepatology, 36, 5 Suppl. S30-S34, 2002).

The treatment of this chronic disease is an unmet clinical need, since current therapy is only partially effective and limited by undesirable side effects. Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, combination therapy has significant side effects and is poorly tolerated in many patients. For instance, in registration trials of pegylated interferon and ribavirin, significant side effects resulted in discontinuation of treatment in approximately 10 to 14 percent of patients. Major side effects of combination therapy include influenza-like symptoms, hematologic abnormalities, and neuropsychiatric symptoms. The development of more effective, convenient and tolerated treatments is a major public health objective. Thus, there is a high medical need for low molecular weight compounds that lead to an inhibition of HCV replication. By inhibiting the HCV replication, a rapid reduction in the viral loads of patients infected with the hepatitis C virus is achieved. A reduction of the viral load is a proof of principle of the clinical antiviral activity of HCV inhibitors. By maintaining low to undetectable levels of viral load in patients, disease progression is delayed or even stopped, avoiding thus the development of chronic hepatitis, liver fibrosis, cirrhosis, end-stage liver disease, and HCC (hepatocellular carcinoma).

Resistance of viruses, and in particular the HCV virus, against inhibitors is also a cause of therapy failure. Many patients receiving anti-HCV therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for antiviral therapy, more particularly for hepatitis therapy. The need in the art is particularly acute for compounds that are active not only on wild type HCV virus, but also on the increasingly more common resistant HCV viruses.

The compounds used in the present invention are derivatives of pyrimidine or triazine. PCT publication WO01/47921 describes pyrimidine and triazine compounds that are inhibitors of kinase activities associated with various inflammatory conditions. In addition, PCT publications WO00/12497 and WO02/076976 describe quinazoline derivatives that are inhibitors of TGFOR receptor kinase and TGF-β mediated signaling.

WO04/087056 relates to bi-cyclic pyrimidine inhibitors of TGF-β, in which a pyrimidine nucleus is bridged at the (5) and (6) position and are further substituted at positions (2) and (4) with substituents comprising aromatic moieties. These compounds are useful in treating subjects with conditions ameliorated by inhibition of TGFβ activity.

WO03/097615 concerns methods of treating fibroproliferative disorders associated with TGF-β signaling, by administering non-peptide small molecule inhibitors of TGF-β specifically binding to the type I TGF-β receptor (TGFβ-R1). The inhibitors are quinazoline derivatives.

WO04/065392 relates to condensed pyridines and pyrimidines and their use as ALK-5 receptor ligands. These compounds are therapeutically active, particularly in the treatment or prophylaxis of disorders characterised by overexpression of transforming growth factor β (TGF-β). Pharmaceutical compositions for use in such therapy are disclosed.

WO03/078426 discloses azolylaminoazines as inhibitors of protein kinases, pharmaceutically acceptable compositions comprising said compounds, and methods of using the compositions in the treatment of various disease, conditions, or disorders.

WO03/078427 discloses azolylaminoazines as inhibitors of protein kinases, pharmaceutically acceptable compositions comprising said compounds, and methods of using the compositions in the treatment of various disease, conditions, or disorders.

WO2003077921 discloses azinylaminoazoles as inhibitors of protein kinases, pharmaceutically acceptable compositions comprising said compounds, and methods of using the compositions in the treatment of various disease, conditions, or disorders.

WO03/078423 discloses compounds useful as inhibitors of protein kinases, pharmaceutically acceptable compositions comprising said compounds, and methods of using the compositions in the treatment of various disease, conditions, or disorders.

WO02/22601 describes pyrazole compositions comprising a pharmaceutically acceptable carrier and compounds which are useful as protein kinase inhibitors, especially as inhibitors of aurora-2 and GSK-3, for treating diseases such as cancer, diabetes and Alzheimer's disease.

DISCLOSURE OF THE INVENTION

The compounds of the present invention are pyrimidine derivatives which contain a fused ring bridging positions 5 and 6. The compounds are of the formula

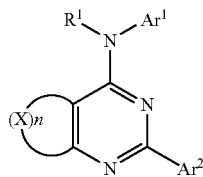

(1)

or a pharmaceutically acceptable salt thereof, wherein the fused ring bridging positions 5 and 6 of the pyrimidine ring is saturated, unsaturated or aromatic. The fused ring is an optionally substituted ring and contains 4-7 members, where each member is independently C, N, O or S. However, if said fused ring contains 6 members, it is not aromatic.

Each of $Ar^1$ and $Ar^2$ is independently an optionally substituted aromatic moiety or optionally substituted heteroaromatic moiety wherein said heteroaromatic moiety contains one or more O, S, and/or N; typically these moieties contain 5-12 members.

$R^1$ is H, or optionally substituted alkyl (1-10C), alkenyl (2-10C), or alkynyl (2-10C).

The compounds useful in the invention are derivatives of pyrimidine containing a bridge at positions 5-6 and mandatory substituents at positions corresponding to the 2- and 4-positions of pyrimidine. Further non-interfering substituents may also be included.

The present invention relates to the use of a compound of the formula

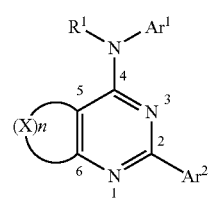

(1)

or a pharmaceutically acceptable salt thereof,
wherein the fused ring bridging positions 5 and 6 of the pyrimidine ring is an optionally substituted saturated, unsaturated or aromatic ring containing 4-7 members, wherein
X is an atom selected from N, O, or S;
n is 0, 1, 2, or 3;
each of $Ar^1$ and $Ar^2$ is independently an optionally substituted aromatic moiety or optionally substituted heteroaromatic moiety wherein said heteroaromatic moiety contains one or more O, S, and/or N, and these aromatic or heteroaromatic moieties contain 5-12 members;
$R^1$ is H, or optionally substituted alkyl (1-10C), alkenyl (2-10C), or alkynyl (2-10C); with the proviso that if said fused ring bridging positions 5 and 6 of the pyrimidine ring contains 6 members, it is not an aromatic ring;
for the manufacture of a medicament useful for inhibiting HCV activity, preventing or treating conditions associated with HCV, in a mammal infected with HCV.

In one embodiment of the present invention, there is provided the use of a compound of the formula (1) for the manufacture of a medicament useful for preventing disease progression towards chronic hepatitis, liver fibrosis, cirrhosis, end-stage liver disease, HCC (hepatocellular carcinoma) and the like, in a mammal infected with HCV.

In one embodiment of the present invention, there is provided the use of a compound of the formula (1) for the manufacture of a medicament useful for treating chronic hepatitis, liver fibrosis, cirrhosis, end-stage liver disease, HCC (hepatocellular carcinoma) and the like, in a mammal infected with HCV.

The compounds useful in the invention are derivatives of pyrimidine containing a bridge at positions 5-6 and mandatory substituents at positions corresponding to the 2- and 4-positions of pyrimidine. Further non-interfering substituents may also be included.

In one embodiment of the present invention, the $Ar^1$ and $Ar^2$ are each independently an optionally substituted aromatic moiety or optionally substituted heteroaromatic moiety wherein said heteroaromatic moiety contains one or two O, S, and/or N, and these aromatic or heteroaromatic moieties contain 5-12 members.

In one embodiment, the present invention relates to the use of a compound of the formula

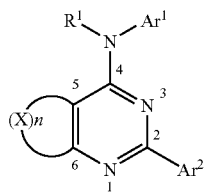

(1)

or a pharmaceutically acceptable salt thereof,
wherein the fused ring bridging positions 5 and 6 of the pyrimidine ring is an optionally substituted saturated, unsaturated or aromatic ring containing 5 or 6 members, wherein X is an atom selected from N or O;
n is 0, 1, or 2;
each of $Ar^1$ and $Ar^2$ is independently an optionally substituted aromatic moiety or optionally substituted heteroaromatic moiety wherein said heteroaromatic moiety contains one or two N, and these aromatic or heteroaromatic moieties contain 5-7 members;
$R^1$ is H, or optionally substituted alkyl (1-10C);
with the proviso that if said fused ring bridging positions 5 and 6 of the pyrimidine ring contains 6 members, it is not an aromatic ring;
for the manufacture of a medicament useful for inhibiting HCV activity, preventing or treating conditions associated with HCV, in a mammal infected with HCV.

In one embodiment, the present invention relates to the use of a compound of the formula

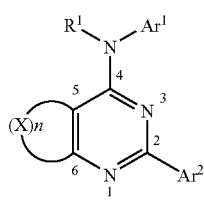

(1)

or a pharmaceutically acceptable salt thereof,
wherein the fused ring bridging positions 5 and 6 of the pyrimidine ring is an optionally substituted saturated, unsaturated or aromatic ring containing 5 or 6 members, wherein X is an atom selected from N or O;
n is 0, 1, or 2;
each of $Ar^1$ and $Ar^2$ is independently an optionally substituted phenyl or an optionally substituted pyridiyl;
$R^1$ is H, or optionally substituted alkyl (1-6C); with the proviso that if said fused ring bridging positions 5 and 6 of the pyrimidine ring contains 6 members, it is not an aromatic ring;
for the manufacture of a medicament useful for inhibiting HCV activity, preventing or treating conditions associated with HCV, in a mammal infected with HCV.

In one embodiment, the present invention relates to the use of a compound of the formula

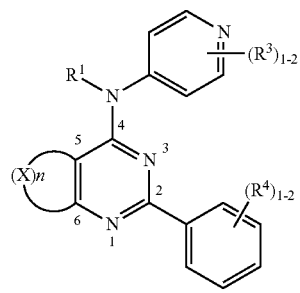

(2)

or a pharmaceutically acceptable salt thereof,
wherein the fused ring bridging positions 5 and 6 of the pyrimidine ring is an optionally substituted saturated, unsaturated or aromatic ring containing 5 or 6 members, wherein X is an atom selected from N or O;
n is 0, 1, or 2;
$R^1$ is H, or optionally substituted alkyl (1-6C);
each $R^3$ is, independently, hydrogen, halo, cyano, nitro, alkyl (1-6C), polyhaloalkyl(1-6C), —COR, —CONR$_2$, —COOR, —OR, —OCOR, —NR$_2$, or —NRCOR;
each $R^4$ is, independently, hydrogen, halo, cyano, nitro, polyhaloalkyl(1-6C), or alkyl(1-6C);
wherein each R is independently hydrogen, hydroxy, amino, mono- or dialkyl(1-6C)amino, cycloalkyl(3-7C), Het, or alkyl(1-6C) optionally substituted with one or two substituents selected from hydroxy, cycloalkyl(3-7C), amino, mono- or dialkyl(1-6C)amino, and Het;
Het is a 5 or 6 membered saturated, partially unsaturated or completely unsaturated heterocyclic ring containing 1 to 2 heteroatoms each independently selected from nitrogen, oxygen and sulfur, and wherein the group Het as a whole may be optionally substituted with one, two or three substituents each independently selected from the group consisting of halo, alkyl(1-6C), hydroxy, and oxo;
with the proviso that if said fused ring bridging positions 5 and 6 of the pyrimidine ring contains 6 members, it is not an aromatic ring;
for the manufacture of a medicament useful for inhibiting HCV activity, preventing or treating conditions associated with HCV, in a mammal infected with HCV.

In one embodiment, the present invention relates to the use of a compound of the formula

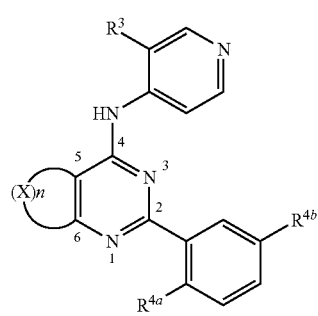

(3)

or a pharmaceutically acceptable salt thereof,
wherein the fused ring bridging positions 5 and 6 of the pyrimidine ring together with the pyrimidine ring forms a group selected from

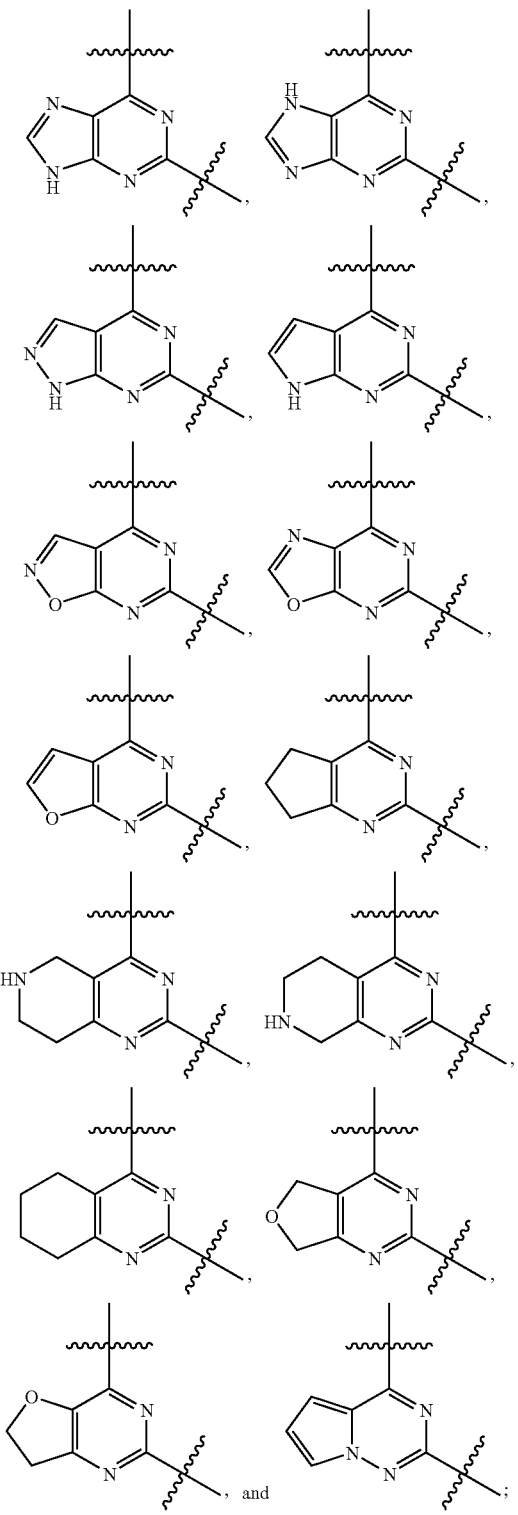

wherein any of these groups may be optionally substituted with one or two substituents selected from alkyl(1-6C), phenyl, and benzyl;
R³ is hydrogen, halo, alkyl(1-6C), —CF₃, —COR, —CONR₂, or —COOR;
each R⁴ᵃ R⁴ᵇ are, independently, hydrogen or halo;
wherein each R is independently hydrogen, hydroxy, amino, mono- or dialkyl(1-6C)amino, cycloalkyl(3-7C), Het, or alkyl(1-6C) optionally substituted with one or two substituents selected from hydroxy, cycloalkyl(3-7C), amino, mono- or dialkyl(1-6C)amino, and Het;

Het is a group selected from

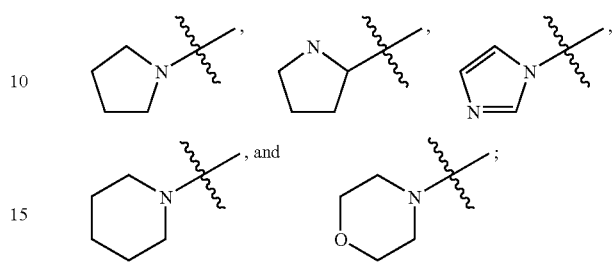

wherein the group Het may be optionally substituted with one or two substituents each independently selected from the group consisting of alkyl(1-6C), and oxo;

for the manufacture of a medicament useful for inhibiting HCV activity, preventing or treating conditions associated with HCV, in a mammal infected with HCV.

In one embodiment, the present invention relates to the use of a compound of the formula

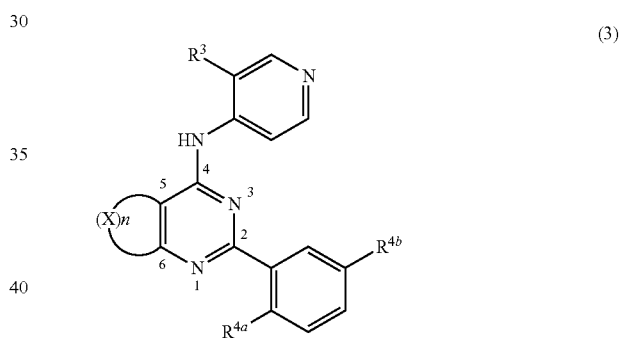

(3)

or a pharmaceutically acceptable salt thereof, wherein the fused ring bridging positions 5 and 6 of the pyrimidine ring together with the pyrimidine ring forms a group selected from

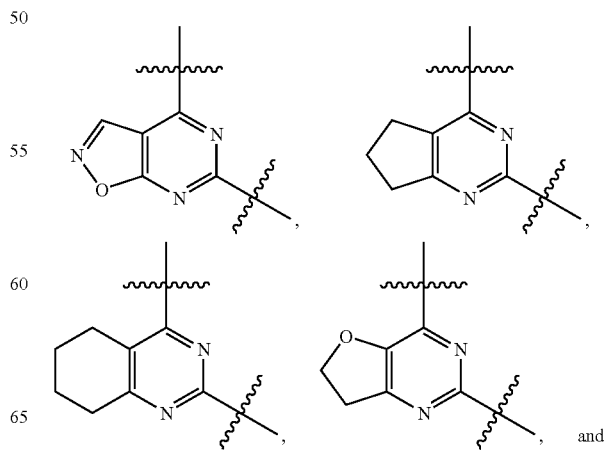

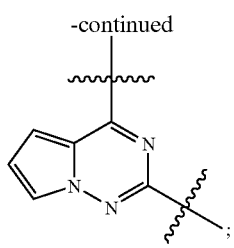

wherein any of these groups may be optionally substituted with one or two alkyl(1-6C);
R³ is hydrogen, alkyl(1-6C), or —CONR₂;
each R$^{4a}$ R$^{4b}$ are, independently, hydrogen or halo;
wherein each R is independently hydrogen, amino, mono- or dialkyl(1-6C)amino, or alkyl(1-6C) optionally substituted with one hydroxy;
for the manufacture of a medicament useful for inhibiting HCV activity, preventing or treating conditions associated with HCV, in a mammal infected with HCV.

As used herein, a "noninterfering substituent" is a substituent which leaves the ability of the compound of formula (1) to inhibit HCV activity qualitatively intact. Thus, the substituent may alter the degree of inhibition, but as long as the compound of formula (1) retains the ability to inhibit activity, the substituent will be classified as "noninterfering."

As used herein, the term "alkyl," "alkenyl" and "alkynyl" include straight-chain, branched-chain and cyclic monovalent substituents, containing only C+H when they are unsubstituted. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (lower alkyl) or 2-6C (lower alkenyl or lower alkynyl).

Heteroalkyl, heteroalkenyl and heteroalkynyl are similarly defined but may contain 1 or more O, S or N heteroatoms or combinations thereof within the backbone residue.

As used herein, "acyl" encompasses the definitions of alkyl, alkenyl, alkynyl, and heteroacyl includes the related heteroforms, each of which are coupled to an additional residue through a carbonyl group.

"Aromatic" moiety or "aryl" moiety refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-8C, or the hetero forms thereof. These carbon chains may also include a carbonyl group, thus making them able to provide substituents as an acyl or heteroacyl moiety.

The term "polyhaloalkyl(1-6C)" as a group or part of a group is defined as mono- or polyhalo substituted alkyl(1-6C), in particular alkyl(1-6C) substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoroalkyl(1-6C) groups, which are alkyl(1-6C) groups wherein all hydrogen atoms are replaced by fluoro atoms, e.g. pentafluoroethyl. In case more than one halogen atom is attached to an alkyl group within the definition of polyhaloalkyl(1-6C), the halogen atoms may be the same or different.

In general, any alkyl, alkenyl, alkynyl, acyl, or aryl group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included. The features of the invention compounds are defined by formulae (1), (2), and (3) and the nature of the substituents is less important as long as the substituents do not interfere with the stated biological activity of this basic structure.

The term halo is generic to fluoro, chloro, bromo and iodo.

As used herein before, the term oxo or (=O) forms a carbonyl moiety when attached to a carbon atom. Whenever a ring or ring system is substituted with an oxo group, the carbon atom to which the oxo is linked is a saturated carbon.

Radicals used in the definitions of the variables include all possible isomers unless otherwise indicated. For instance pyridyl includes 1-pyridyl, 2-pyridyl, 3-pyridyl and 4-pyridyl; pentyl includes 1-pentyl, 2-pentyl and 3-pentyl.

When any variable occurs more than one time in any constituent, each definition is independent.

Non-interfering substituents on Ar¹ or Ar², include, but are not limited to, alkyl, alkenyl, alkynyl, halo, —OR, —NR₂, —SR, —SOR, —SO₂R, —OCOR, —NRCOR, —NRCONR₂, —NRCOOR, —OCONR₂, —RCO, —COOR, —NRSOR, —NRSO₂R, —SO₃R, —CONR₂, SO₂NR₂, wherein each R is independently H or alkyl (1-8C), —CN, —CF₃, and NO₂, and like substituents. Non-interfering substituents on Ar¹ or Ar², include, but are not limited to, alkyl, alkenyl, alkynyl, halo, —OR, —NR₂, —SR, —SOR, —SO₂R, —OCOR, —NRCOR, —NRCONR₂, —NRCOOR, —OCONR₂, —RCO, —COR, —COOR, —NRSOR, —NRSO₂R, —SO₃R, —CONR₂, SO₂NR₂, wherein each R is independently H or alkyl (1-8C), —CN, —CF₃, and NO₂, and like substituents. Preferred embodiments for R are H, alkyl (1-10C) or a heteroatom-containing form thereof, each optionally substituted, especially (1-4C) alkyl; alkoxy (1-8C), acylamido, aryloxy, arylalkyloxy, especially wherein the aryl group is a phthalimido group, and alkyl or arylalkyl amine.

Preferably Ar¹ and Ar² are optionally substituted phenyl, 2-, 3- or 4-pyridyl, indolyl, 2- or 4-pyrimidyl, pyridazinyl, benzotriazolyl or benzimidazolyl. More preferably Ar¹ and Ar² are phenyl, pyridyl, or pyrimidyl. Preferably Ar¹ is pyridyl or pyrimidyl and Ar² is phenyl. Each of these embodiments may optionally be substituted with a group such as alkyl, alkenyl, alkynyl, aryl, —O-aryl, —O-alkylaryl, —O-aroyl, —NR-aryl, —N-alkylaryl, —NR-aroyl, halo, —OR, —NR₂, —SR, —OOCR, —NROCR, —RCO, —COOR, —CONR$_2$, and/or SO$_2$NR$_2$, wherein each R is independently H or alkyl (1-8C), and/or by —CN, —CF$_3$, and/or NO$_2$. Each of these embodiments may optionally be substituted with one or two groups such as alkyl, alkenyl, alkynyl, aryl, —O-aryl, —O-alkylaryl, —O-aroyl, —NR-aryl, —N-alkylaryl, —NR-aroyl, halo, —OR, —NR$_2$, —SR, —OOCR, —OCOR, —NROCR, —NRCOR, —RCO, —COR, —COOR, —CONR$_2$, and/or SO$_2$NR$_2$, wherein each R is independently H or alkyl (1-8C), and/or by —CN, —CF$_3$, and/or NO$_2$. Alkyl, alkenyl, alkynyl and aryl portions of these may be further substituted by similar substituents.

Preferred substituents on Ar$^1$ or Ar$^2$ include alkyl, alkenyl, alkynyl, halo, —OR, —SR, —NR$_2$ wherein R is H or alkyl (1-4C); and/or arylamino, arylalkylamino, including alkylamino which is substituted by more than one aryl. As stated above, any aryl or alkyl group included within a substituent may itself be substituted similarly. These substituents may occupy all available positions of the ring, preferably 1-2 positions, or more preferably only one position.

Any of the aryl moieties, including those depicted in formulae (1), (2), and (3) especially the phenyl moieties, may also comprise two substituents which, when taken together, form a 5-7 membered carbocyclic or heterocyclic aliphatic ring. The bridge between positions 5 and 6 of the pyrimidine ring forms a fused ring system wherein, if the fused ring contains 6 members, it is not aromatic. However, the bridge may contain pi bonds and may contain one or more heteroatoms which are selected from N, O, and S. Preferred embodiments include those wherein the bridge results in a 5-membered ring optionally containing one or two nitrogens, a nitrogen and an oxygen, an oxygen, an additional double bond, a saturated bridge, or a 6-membered ring formed by a bridge which is saturated. In one embodiment, the 6-membered saturated bridge-generated ring contains one or two nitrogen. The ring formed by the bridge may itself be substituted. The substituents described above for Ar$^1$ and Ar$^2$ may also be present as fused ring systems.

Whenever used hereinafter, the term "compounds of formula (1)", "compounds of formula (2)", "compounds of formula (3)", or "the present compounds" or similar terms, it is meant to include the compounds of formulae (1), (2), and (3), their prodrugs, N-oxides, addition salts, quaternary amines, metal complexes, and stereochemically isomeric forms. One embodiment comprises the compounds of formula (1) or any subgroup of formula (1) specified herein, including compounds of formula (2) and (3), as well as the N-oxides, salts, as the possible stereoisomeric forms thereof. Another embodiment comprises the compounds of formula (1) or any subgroup of compounds of formula (1) specified herein, as well as the salts as the possible stereoisomeric forms thereof.

For therapeutic use, salts of the compounds of formula (1) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (1) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), benzoic, maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (1) containing an acidic proton may also be converted into their non-toxic metal or amine addition salt forms by treatment with appropriate organic and inorganic bases. Thus, if a carboxyl moiety is present on the compound of formula (1), the compound may also be supplied as a salt with a pharmaceutically acceptable cation. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (1) as well as the salts thereof, are able to form. Such solvates are for example hydrates, alcoholates and the like.

The compounds of formula (1) may also be supplied in the form of a "prodrug" which is designed to release the compound of formula (1) when administered to a subject. The term "prodrug" as used herein means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Prodrug formed designs are well known in the art, and depend on the substituents contained in the compound of formula (1). For example, a substituent containing sulfhydryl could be coupled to a carrier which renders the compound biologically inactive until removed by endogenous enzymes or, for example, by enzymes targeted to a particular receptor or location in the subject.

Preferred are pharmaceutically acceptable ester prodrugs that are hydrolysable in vivo and are derived from those compounds of formula (1) having a hydroxy or a carboxyl group. An in vivo hydrolysable ester is an ester, which is hydrolysed in the human or animal body to produce the parent acid or alcohol. Suitable pharmaceutically acceptable esters for carboxy include alkoxymethyl esters for example methoxymethyl, alkanoyloxymethyl esters for example pivaloyloxymethyl, phthalidyl esters, cycloalkoxycarbonyloxyalkyl esters for example 1-cyclohexylcarbonyloxyethyl; 1,3-dioxolen-2-onylmethyl esters for example 5-methyl-1,3-dioxolen-2-onylmethyl; and alkoxycarbonyloxyethyl esters for example 1-methoxycarbonyloxyethyl which may be formed at any carboxy group in the compounds of this invention.

An in vivo hydrolysable ester of a compound of the formula (1) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

The term "quaternary amine" as used hereinbefore defines the quaternary ammonium salts which the compounds of formula (1) are able to form by reaction between a basic nitrogen of a compound of formula (1) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (1) wherein one or several nitrogen atoms are oxidized to the so-called N-oxide.

It will be appreciated that the compounds of formula (1) may have metal binding, chelating, complex forming properties and therefore may exist as metal complexes or metal chelates. Such metalated derivatives of the compounds of formula (1) are intended to be included within the scope of the present invention.

Some of the compounds of formula (1) may also exist in their tautomeric form. Such forms although not explicitly indicated in the above formula are intended to be included within the scope of the present invention.

The compounds of formula (1) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (1) may possess.

With reference to the instances where (R) or (S) is used to designate the absolute configuration of a chiral atom within a substituent, the designation is done taking into consideration the whole compound and not the substituent in isolation.

In the event that any of the substituents of formula (1) contain chiral centers, as some, indeed, do, the compounds of formula (1) include all stereoisomeric forms thereof, both as isolated stereoisomers and mixtures of these stereoisomeric forms. Said mixtures may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereo specifically. Preferably, if a specific stereoisomer is desired, said compound is will be synthesized by stereospecific methods of preparation. These methods will advantageously employ enantiomerically pure starting materials.

The diastereomeric racemates of the compounds of formula (1) can be obtained separately by conventional methods. Appropriate physical separation methods that may advantageously be employed are, for example, selective crystallization and chromatography, e.g. column chromatography.

For some of the compounds of formula (1), their prodrugs, N-oxides, salts, solvates, quaternary amines, or metal complexes, and the intermediates used in the preparation thereof, the absolute stereochemical configuration was not experimentally determined.

A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Synthesis of the Invention Compounds

A number of synthetic routes may be employed to produce the compounds of the invention. In general, they may be synthesized using reactions known in the art. Any art-known method for synthesis may be employed. However, the following synthetic routes are convenient for preparation of the invention compounds. Typical invention compounds are as shown below:

| Co. No | Structure |
|---|---|
| 1 | 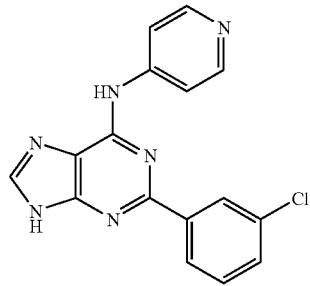 |
| 2 | 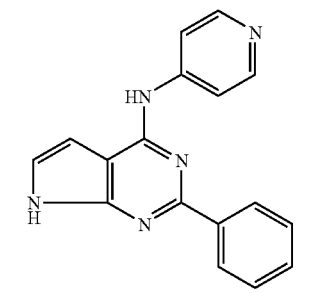 |
| 3 | 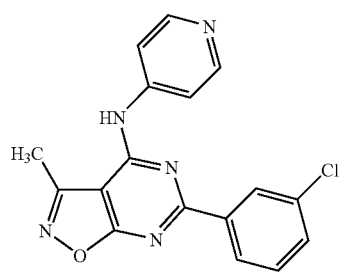 |
| 4 | 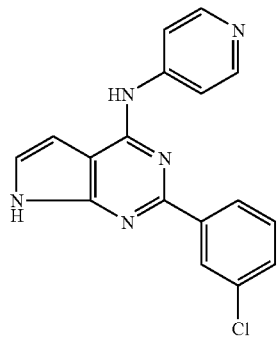 |
| 5 | 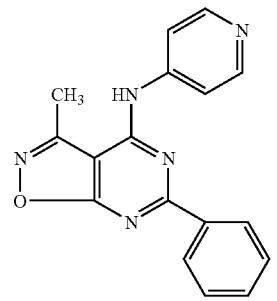 |
-continued
| Co. No | Structure |
|---|---|
| 6 | 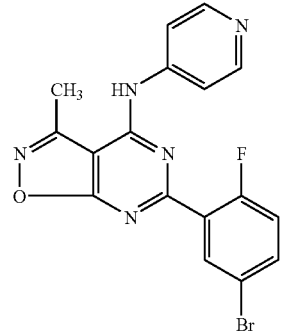 |
| 7 | 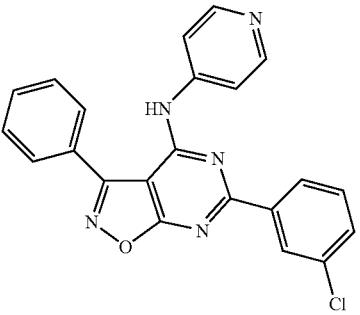 |
| 8 | 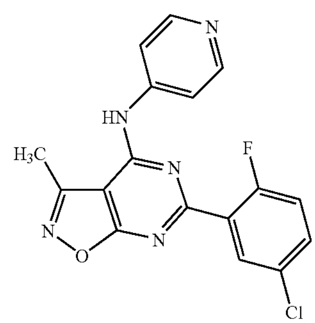 |
| 9 | 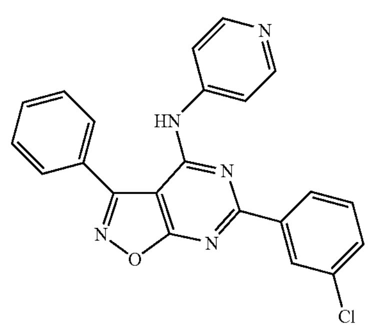 |

-continued

| Co. No | Structure |
|---|---|
| 10 | 3-methyl-N-(pyridin-4-yl)-6-(3-iodophenyl)isoxazolo[5,4-d]pyrimidin-4-amine |
| 11 | 3-ethyl-N-(pyridin-4-yl)-6-(5-chloro-2-fluorophenyl)isoxazolo[5,4-d]pyrimidin-4-amine |
| 12 | 3-methyl-N-(pyridin-4-yl)-6-(2-fluorophenyl)isoxazolo[5,4-d]pyrimidin-4-amine |
| 13 | 3-methyl-N-(pyridin-3-yl)-6-(2-fluorophenyl)isoxazolo[5,4-d]pyrimidin-4-amine |
| 14 | 3-methyl-N-(pyridin-4-yl)-6-(2-chlorophenyl)isoxazolo[5,4-d]pyrimidin-4-amine |

-continued

| Co. No | Structure |
|---|---|
| 15 | 3-methyl-N-(pyridin-4-yl)-6-(3-bromophenyl)isoxazolo[5,4-d]pyrimidin-4-amine |
| 16 | 7-methyl-N-(pyridin-4-yl)-2-phenyl-7H-purin-6-amine |
| 17 | 3-methyl-N-(pyridin-4-yl)-6-(3-chlorophenyl)isoxazolo[5,4-d]pyrimidin-4-amine |
| 18 | 6-methyl-N-(pyridin-4-yl)-2-(3-chlorophenyl)furo[2,3-d]pyrimidin-4-amine |
| 19 | 2-methyl-N-(pyridin-4-yl)-5-(3-chlorophenyl)oxazolo[5,4-d]pyrimidin-7-amine |

-continued

| Co. No | Structure |
|---|---|
| 20 | (structure) |
| 21 | (structure) |
| 22 | (structure) |
| 23 | (structure) |

-continued

| Co. No | Structure |
|---|---|
| 24 | (structure) |
| 25 | (structure) |
| 26 | (structure) |
| 27 | (structure) |
| 28 | (structure) |

-continued

| Co. No | Structure |
|--------|-----------|
| 29 | 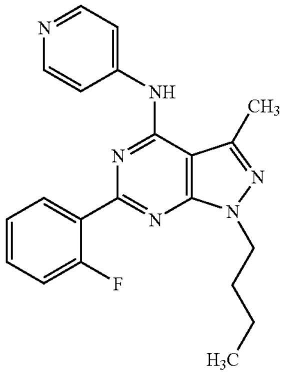 |
| 30 | 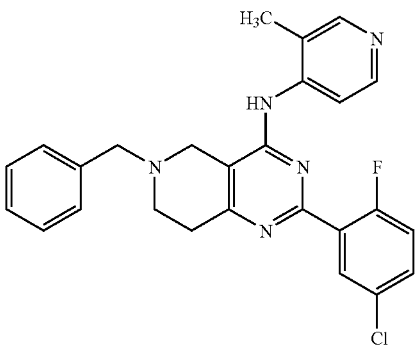 |
| 32 | 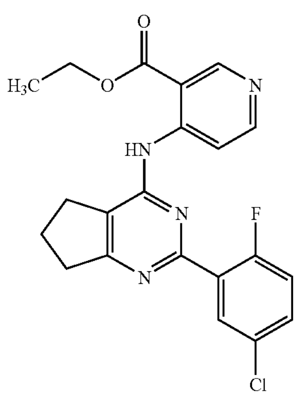 |
| 33 | 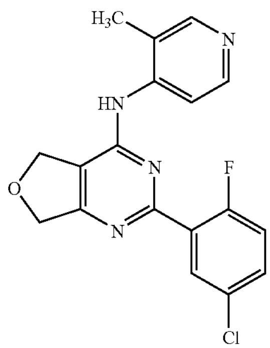 |
| 34 | |
| 35 | |
| 36 | |
| 37 | |

-continued

| Co. No | Structure |
|---|---|
| 38 | 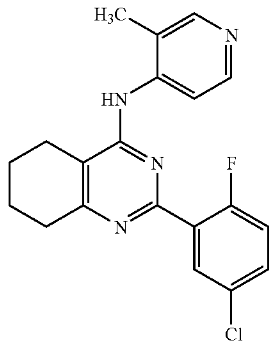 |
| 39 | 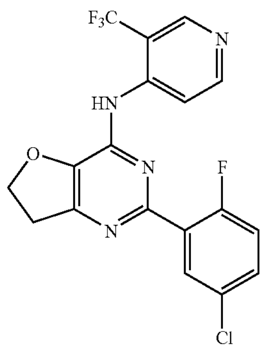 |
| 40 | 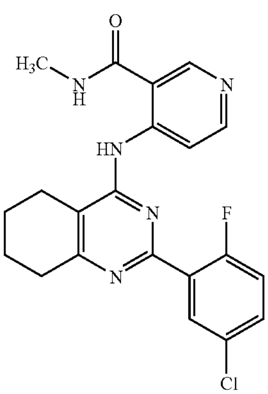 |
| 41 | 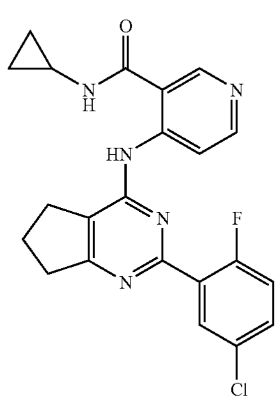 |

-continued

| Co. No | Structure |
|---|---|
| 42 | 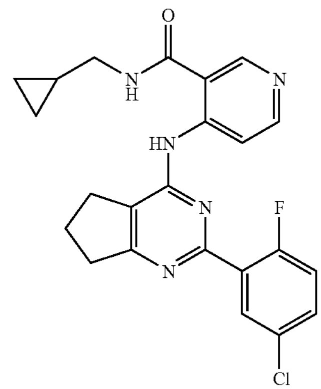 |
| 43 | 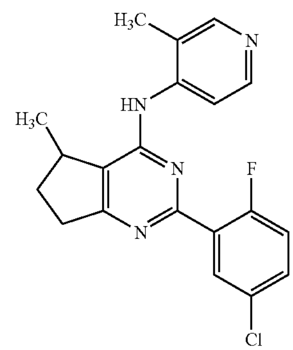 |
| 44 | 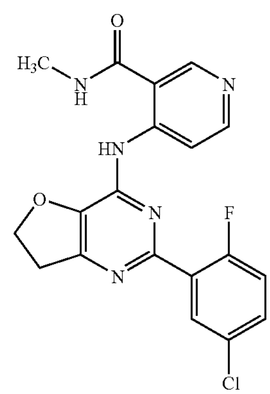 |
| 45 | 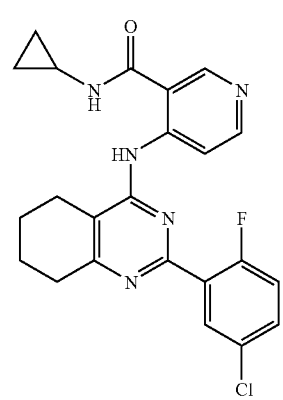 |

-continued
| Co. No | Structure |
|---|---|
| 46 | 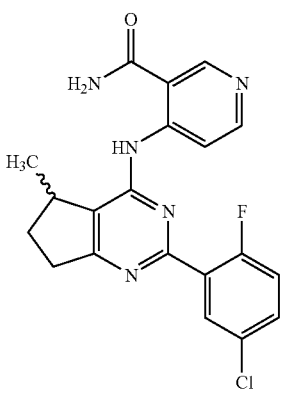 |
| 47 | 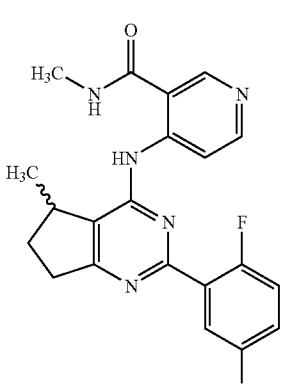 |
| 48 | 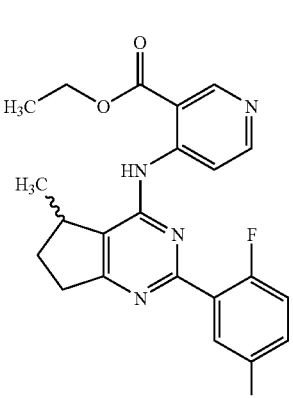 |
| 49 | 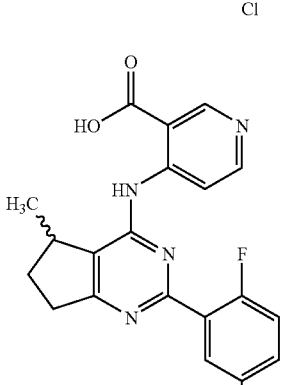 |
-continued
| Co. No | Structure |
|---|---|
| 50 | 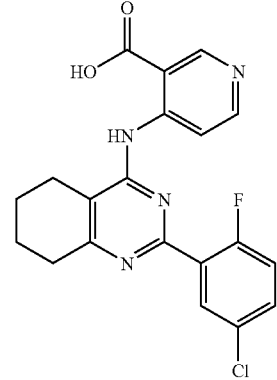 |
| 51 | 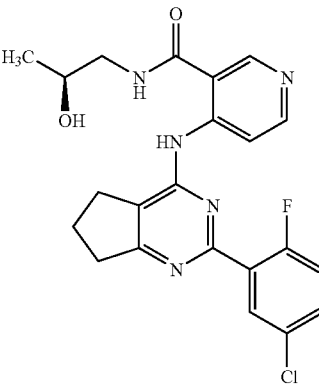 |
| 52 | 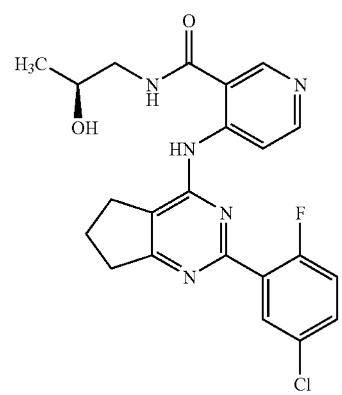 |
| 53 | Chiral |

-continued
| Co. No | Structure |
|---|---|
| 54 | 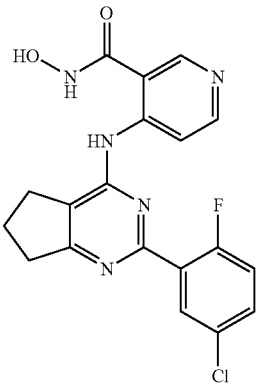 |
| 55 | Chiral 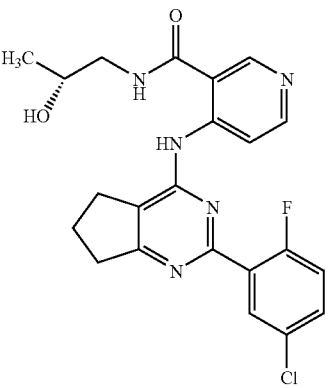 |
| 56 | 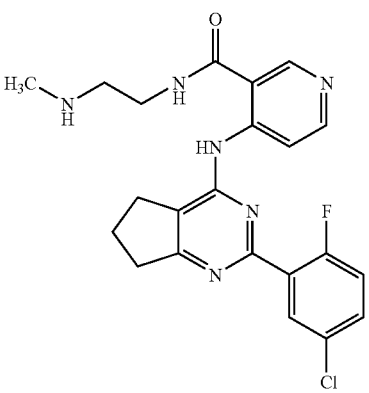 |
-continued
| Co. No | Structure |
|---|---|
| 57 | 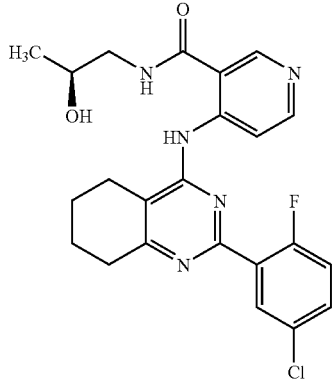 |
| 58 | 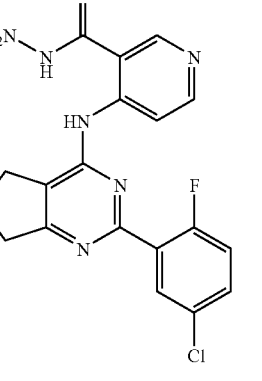 |
| 59 | 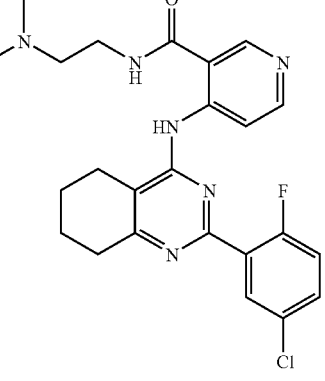 |
| 60 | 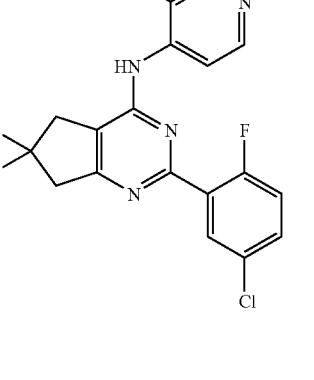 |

| Co. No | Structure |
|---|---|
| 61 | 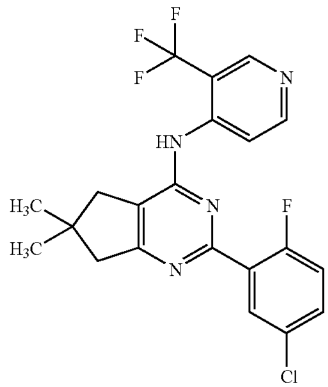 |
| 62 | 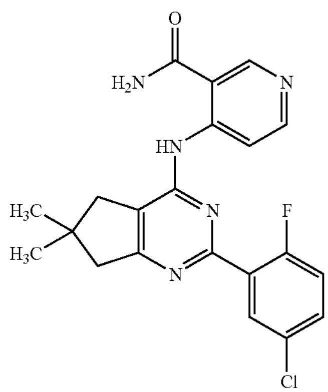 |
| 63 | 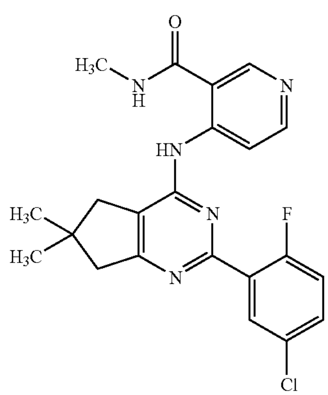 |
| 64 | Chiral |
| 65 | Chiral |
| 66 | |
| 67 | |
| 68 | |

| Co. No | Structure |
|---|---|
| 69 | 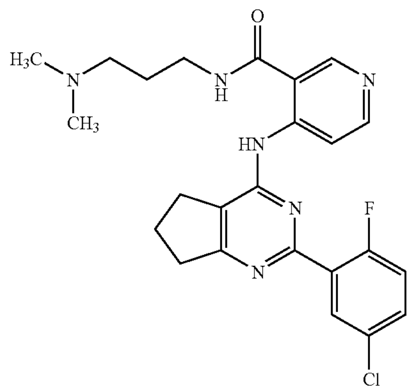 |
| 70 | 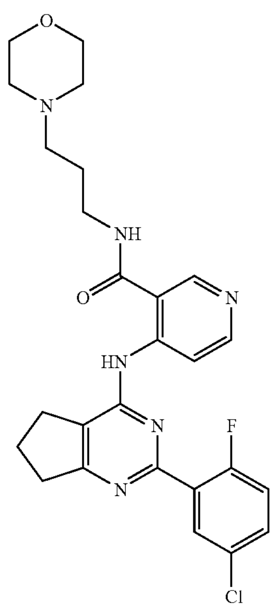 |
| 71 | 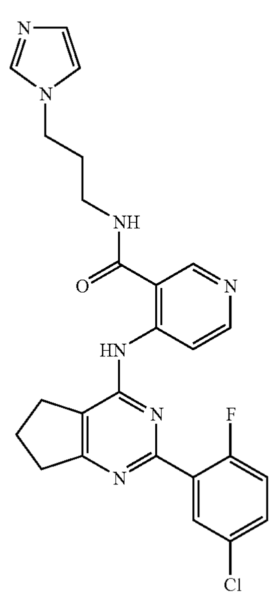 |
| 72 | |
| 73 | |

-continued
| Co. No | Structure |
|---|---|
| 74 | 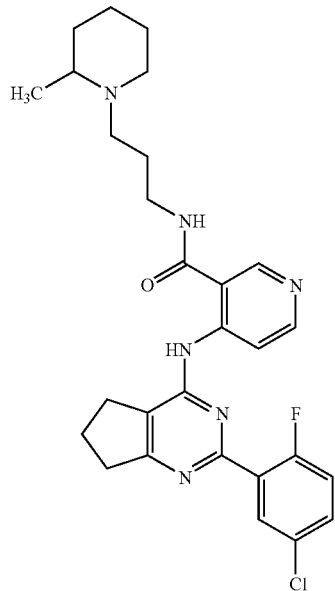 |
| 75 | 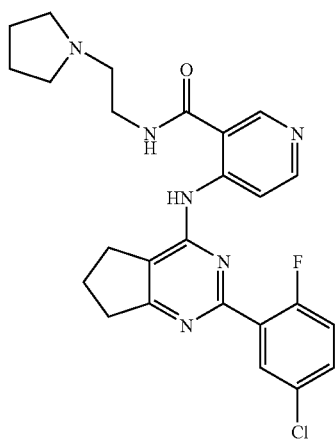 |
| 76 | 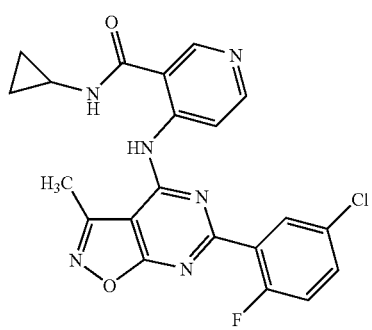 |
-continued
| Co. No | Structure |
|---|---|
| 77 | 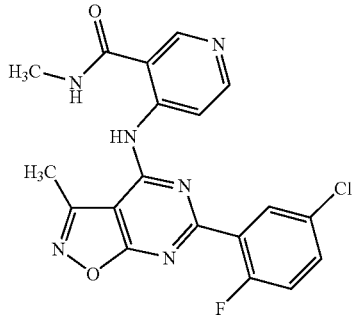 |
| 78 | 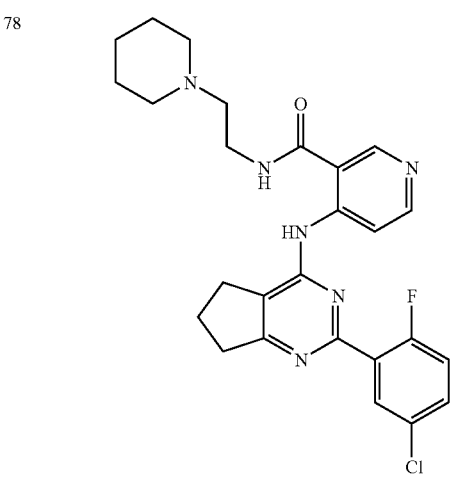 |
| 79 | 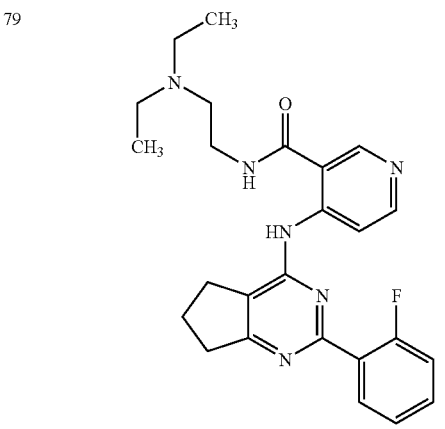 |
| 80 | 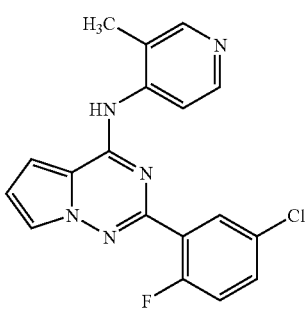 |

-continued

| Co. No | Structure |
|---|---|
| 81 | 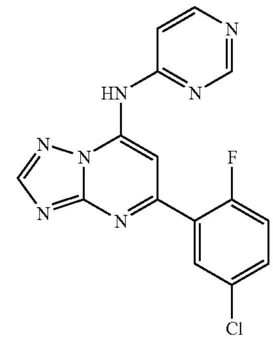 |
| 82 | 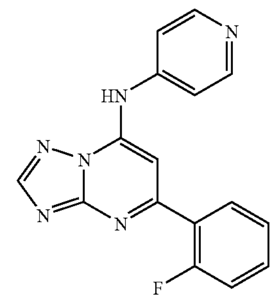 |
| 83 | 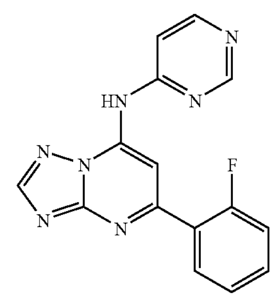 |

Scheme A

Synthesis of Compounds 1 and 26

This general scheme was used to prepare compounds 1 and 16.

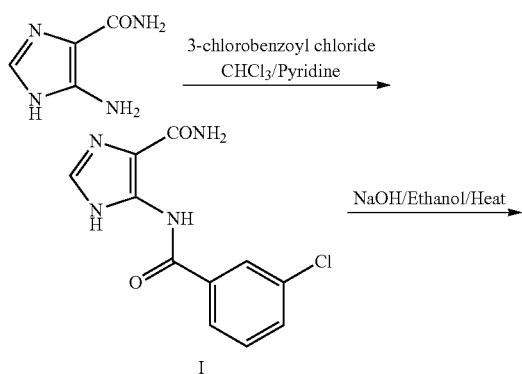

I

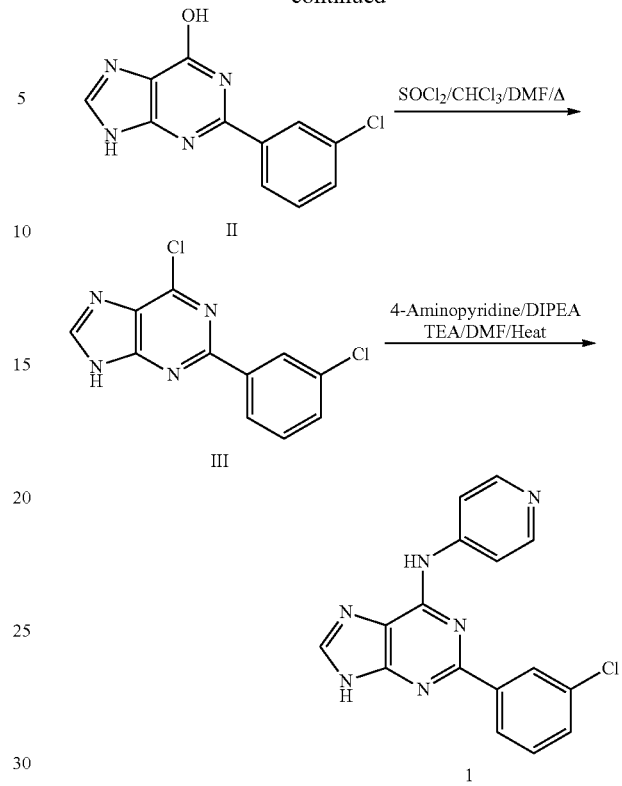

Preparation of Compound of Formula (I):

2.53 g of 4-amino-5-imidazolecarboxamide was dissolved in 30 mL chloroform and 30 mL dimethylformamide. To this solution was added at 0° C. 3.02 mL of 3-chlorobenzoylchloride, followed by 5.4 mL di-isopropylethylamine. The reaction mixture was allowed to warm to room temperature and maintained at room temperature overnight. The reaction mixture was diluted with chloroform and washed with water, 10% aqueous sodium carbonate solution and brine. The organic layer was dried over anhydrous sodium sulfate and filtered. The crude residue obtained after concentration was taken up in the minimal amount of chloroform and chromatographed on silica gel, using ethyl acetate, 5% methanol to give 4.81 g of compound of formula (I). Note: For the synthesis of compound 16, methyl-4-amino-5-imidazolecarboxamide, was used.

Preparation of Compound of Formula (II):

2.74 g of compound of formula (I) was suspended in 75 mL ethanol, added 5 mL 10 N sodium hydroxide to the reaction mixture and the reaction mixture was refluxed for four hours. After cooling to room temperature the reaction mixture was concentrated to remove ethanol and then diluted with water. The solution was then acidified by the addition of 1 N hydrochloric acid, at 0° C., to pH 6.5. The white precipitate that formed was collected by filtration, washed with water and ether and dried under high vacuum to give 0.84 g of compound of formula (II).

Preparation of Compound of Formula (III):

0.84 g of compound of formula (II) was suspended in 60 mL chloroform, to this suspension was added 1.1 mL thionyl chloride and 2 mL dimethylformamide. The resulting mixture was refluxed under nitrogen for three hours. The reaction mixture was cooled to room temperature and concentrated to a yellow residue. This residue was taken up in chloroform and ice was added to the reaction mixture. The cold solution was washed with 5% aqueous sodium bicarbonate solution and brine. The organic layer was dried over anhydrous sodium sulfate and filtered. After concentration, the residue that was obtained was treated with cold ethyl acetate. A white solid separates. This solid was filtered and washed with ethyl acetate, to give 0.46 g of compound of formula (III).

Preparation of Compound of Formula (1):

0.46 g of compound of formula (III) was dissolved in 10 mL dry dimethylformamide, to this was added 0.67 ml diisopropylethylamine. The reaction mixture was heated to 60° C., and to this was added a solution of 0.21 g 4-aminopyridine. The reaction mixture was heated under reflux for one hour. After cooling to room temperature the reaction mixture was concentrated to a minimal volume and the product purified by preparative reverse phase HPLC, using a C18 Vydac® column, using a gradient of water, acetonitrile (both containing 0.1% trifluoroacetic acid). 15 mg of compound of formula (1) was obtained after lyophilization of fractions containing desired product. Analysis: $^1$H NMR $d_6$ DMSO, LCMS, $M^+$323.

Preparation of Compound of Formula (26):

Compound 26 was prepared according to the procedures outline in Scheme A, using N-1-phenyl-2-aminoimidazole-3-carboxamide and benzoyl chloride.

Scheme B (Synthesis of Compounds 3, 5-15 and 17):

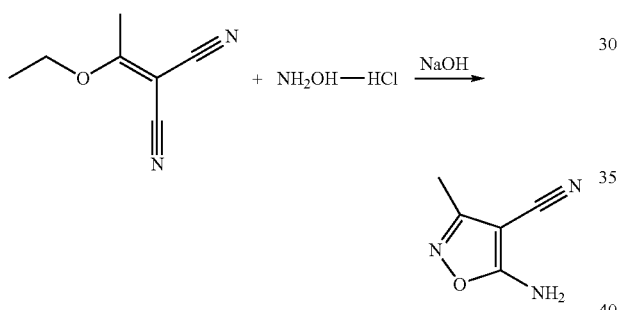

Preparation of 3-amino-4-cyano-5-methyl isoxazole

Hydroxylamine hydrochloride (12.78 g, 0.184 mole) was dissolved in 40 ml water, treated with sodium hydroxide (7.36 g, 0.184 mole). 60 ml ethanol (anhydrous) was added and while stirring (1-ethoxyethylidene)malonitrile (25 g, 0.184 mole) was added carefully. The reaction mixture was heated to 50° C. for 30 min, then stirred overnight at room temperature. Ethanol was removed under vacuum, the filtered solid product was washed with water, dried under vacuum to obtain 21.93 g (96.8% yield).

Note: For the synthesis of 7 and 11, the corresponding ethyl hydroxylamine was used and for the synthesis of 9, the corresponding phenyl hydroxylamine was used.

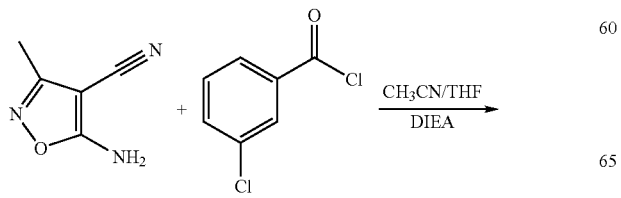

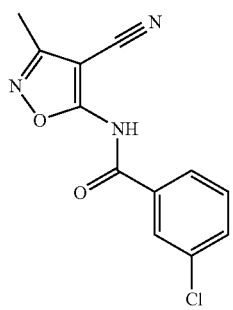

Preparation of N-(3-chlorobenzoyl)-4-cyano-3-methyl-5-carboxamide 3-amino-4-cyano-5-methyl isoxazole (6.0 g, 0.0487 mole) was suspended in acetonitrile/tetrahydrofuran (30 ml/10 ml). Diisopropylethylamine (8.26 ml, 0.0487 mole) was added followed by dropwise addition of 3-chlorobenzoyl chloride. The mixture was stirred at room temperature overnight. The precipitated product was isolated by filtration, washed with chloroform. 1.31 g product were obtained (11% yield).

Note: For the synthesis of compounds 3, 5, 6, 8, 10, 12, 13, 14, 15 and 17, the corresponding acid chlorides were used.

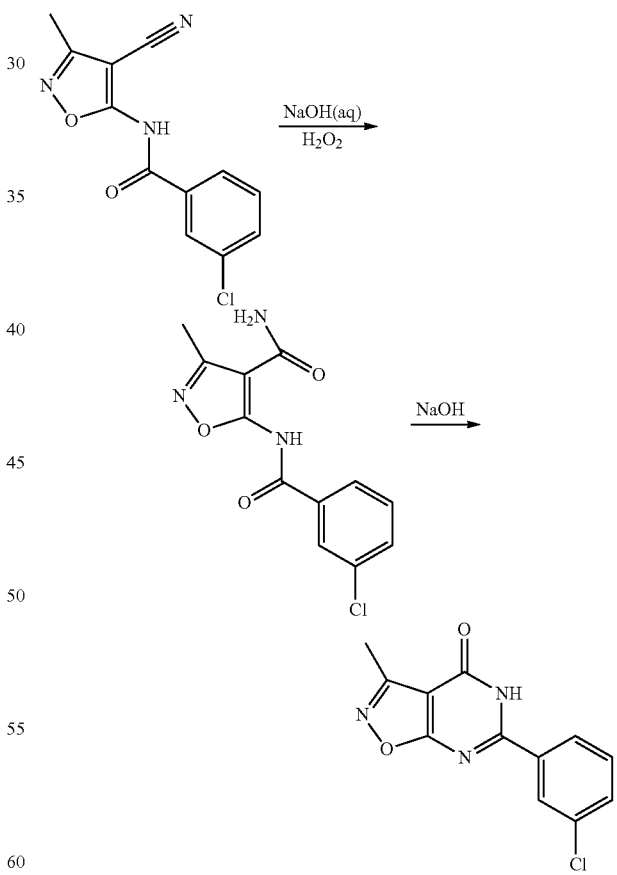

Preparation of 3-methyl-6-(3-chlorophenyl) isoxazole[5,4d]pyrimidone

N-(3-chlorobenzoyl)-4-cyano-3-methyl-5-carboxamide (1.0 g, 15 mmole) was suspended in 20 ml 1 M sodium hydroxide and treated with 8 ml 30% hydrogen peroxide. The mixture was refluxed overnight. The cooled reaction mixture was placed on an ice batch and treated with 1 M hydrochloric acid to pH 6. Filtered the product as a white precipitate and dried under vacuum to give 537 mg (53% yield).

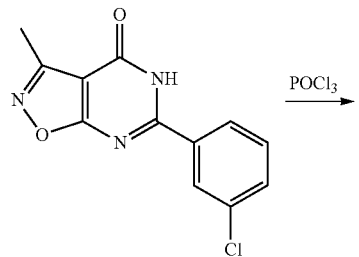

Preparation of 3-methyl-4-chloro-6-(3-chlorophenyl) isoxazole[5,4d]pyrimidine 3-methyl-6-(3-chlorophenyl) isoxazole[5,4d]pyrimidone (535 mg, 2.04 mmole) was suspended in phosphorus oxychloride (6 ml) and heated to reflux for 4 hours. The excess of phosphorus oxychloride was removed, ice and chloroform (10 ml) were added, basified with saturated sodium bicarbonate, the product into chloroform was extracted and the extracts dried over sodium sulfate (anh). The product was purified by silica gel chromatography eluting with chloroform. 200 mg product was obtained.

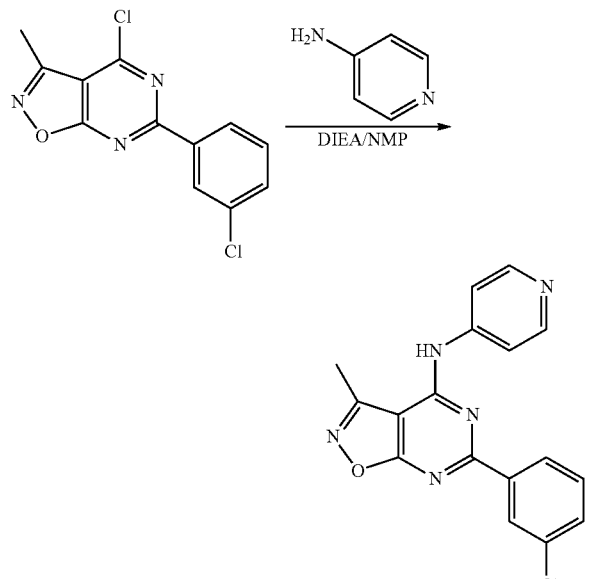

Preparation of 3-methyl-4-(4-aminopyridyl)-6-(3-chlorophenyl) isoxazole[5,4d]pyrimidine (17)

4-aminopyridine (80.6 mg, 0.859 mmole) was dissolved in N-methylpyrrolidone, diisopropylethylamine (149 microliters) was added followed by 3-methyl-4-chloro-6-(3-chlorophenyl) isoxazole[5,4d]pyrimidine (120 mg, 0.428 mmole). The mixture was heated to 50° C. with stirring for 1 hour. Product was purified by preparative HPLC on C18 column.

Scheme C (Synthesis of Compounds 2 and 4):

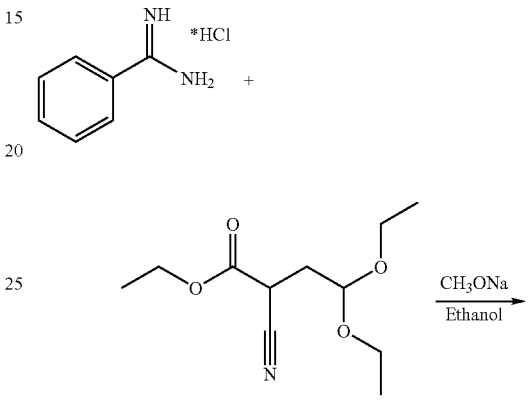

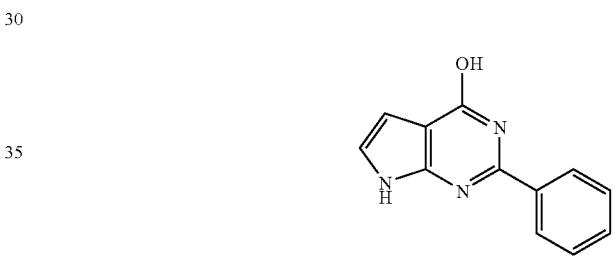

Preparation of 2-phenyl-pyrrolo[2,3d]pyrimidinone

Benzamidine hydrochloride (4.0 g, 0.25 mol) was dissolved in 64 ml of ethanol. To this 8.0 ml of a 25 wt % solution of sodium methoxide was added. Reaction was then stirred at room temperature for 5 hrs, and filtered. Filtrate was then added to ethyl-2-cyano-4,4-diethoxybutyrate (4.80 g, 0.21 mol). This solution was refluxed for 5 hrs. Half of solvent was removed under reduced pressure, then 80 ml of ice water was added, and the pH was adjusted to 7 with acetic acid. Material was then chilled for 6 hrs and product was isolated by vacuum filtration.

Note: For the synthesis of compound 4, 3-chlorobenzamidine was used.

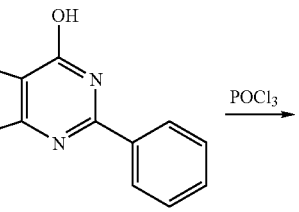

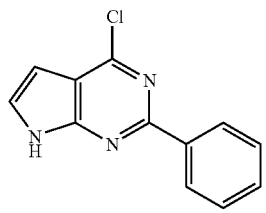

Preparation of 4-chloro-2-phenyl-pyrrolo[2,3d]pyrimidine 2-phenyl-pyrrolo[2,3d]pyrimidinone (1.0 g 4.73 mmol) was treated with phosphorous oxychloride (7 ml, 27.7 mmol) and refluxed for 5 hrs. Excess phosphorous oxychloride was removed under reduced pressure and then extracted with chloroform, washed with sodium bicarbonate. The organic layer was dried over sodium sulfate (anh), then concentrated to dryness to give the product.

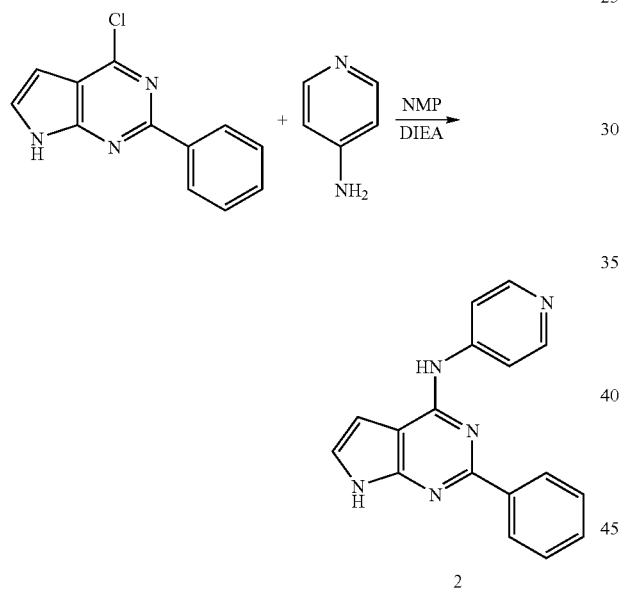

2

Preparation of 4-(4-aminopyridyl)-2-phenyl-pyrrolo[2,3d]pyrimidine (2)

4-chloro-2-phenyl-pyrrolo[2,3d]pyrimidine (0.12 g, 1.27 mmol) was dissolved in 4 ml of NMP. N,N'-Diisopropylethylamine (0.229 ml) was added followed by 4-amino-pyridine (0.15 g, 0.635 mmol). Reaction mixture was heated to reflux for 2 hours, cooled and purified by preparative HPLC.

Scheme D (Synthesis of Compound 18):

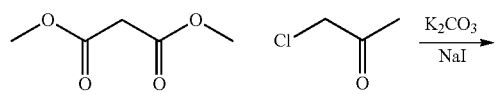

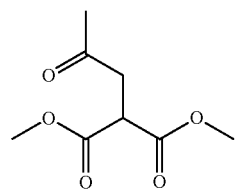

Preparation of Acetylmethyl-dimethylmalonate

Dimethyl malonate (5 g, 0.189 mole) was treated with potassium carbonate (34.78 g, 0.25 mole), sodium iodide (1.00 g, 0.0067 mole) and then warmed while chloroacetone (23.1 g, 0.25 mole) was added rapidly batchwise. The reaction mixture was heated to 100° C. for 20 min. To the cooled reaction mixture 50 ml ethanol were added, and the filtered solid material was washed with ethanol. Ethanol was removed from filtrate under vacuum. Product was isolated by vacuum distillation. 11.26 g product were obtained (32% yield).

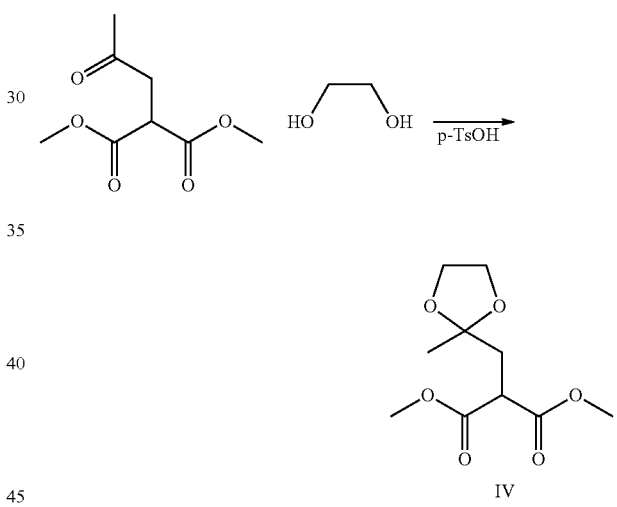

IV

Preparation of Compound of Formula (IV):

Ethylene glycol (3.90 g, 0.0628 mole), the acetylmethyldimethylmalonate (11.26 g, 0.06 mole), and p-toluene sulfonic acid (0.21 g, 0.0011 mole) were combined in 25 ml benzene. The reaction mixture was heated to reflux collecting water in a Dean Stark trap overnight. The reaction mixture was washed with sodium 10% sodium bicarbonate (2×10 ml) and the benzene was dried over sodium sulfate. Solvent was removed to obtain product as an oil, 14.1 g.

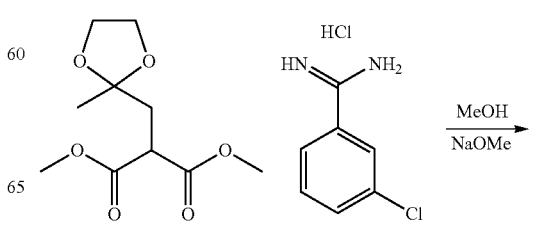

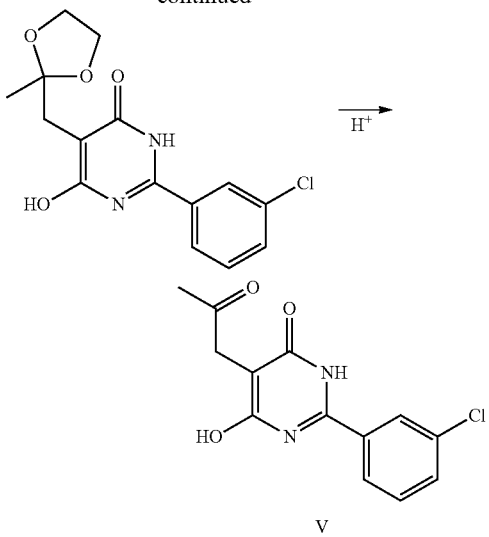

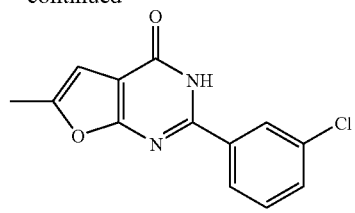

Preparation of 6-methyl-2-chlorophenyl-furano[3,2d]pyrimidone 6-hydroxy-5-acetylmethyl-2-(3-chlorophenyl)pyrimidone (5.0 g) was treated with concentrated sulfuric acid (80 ml). The reaction mixture was stirred at room temperature for 4 hours, then neutralized with sodium carbonate and extracted with chloroform, the chloroform extract was washed with water, dried over sodium sulfate (anh) and the solvent was removed to give product (1.10 g).

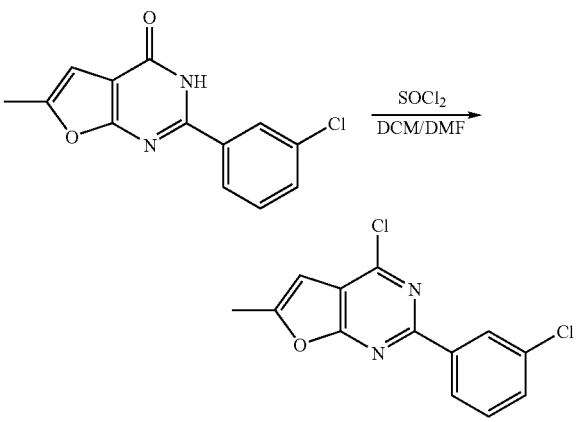

Preparation of Compound of Formula (V):

Protected dimethyl malonate derivative (5.0 g, 0.0215 mole) was dissolved in methanol (20 ml), 3-chlorobenzamidine hydrochloride was added, followed by 25% sodium methoxide (16 ml, 0.0646 mole). The reaction mixture was stirred at room temperature for 3 days. Mixture was diluted with water (50 ml) and 60 ml 1 M HCl was added and stirred for 1 hour room temp, then 4 ml concentrated HCl were added and stirred overnight, to give final product. Methanol was removed under vacuum, and product was obtained by filtration and vacuum drying. 5 g product were obtained.

Preparation of 6-methyl4-chloro-2-chlorophenyl-furano[3,2d]pyrimidine 6-methyl-2-chlorophenyl-furano[3,2-d]pyrimidone (480 mg, 1.84 mmole) was suspended in dichloromethane (4 ml). Thionyl chloride (1.6 ml, 22.5 mmole) and dimethylformamide (0.5 ml) was added and heated to reflux for 3 hours. Excess solvent was removed, the residue was treated with ice, extracted into chloroform, washed with 10% sodium bicarbonate and water, dried over sodium sulfate (anh) and the solvent was removed to give 480 mg product.

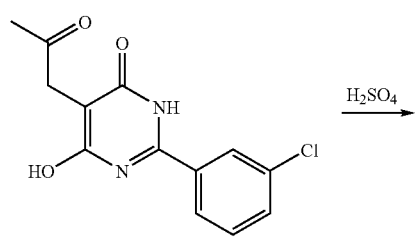

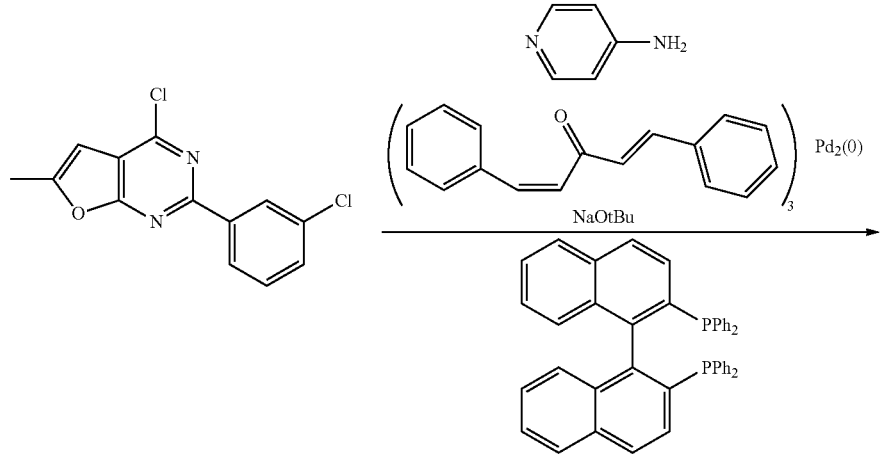

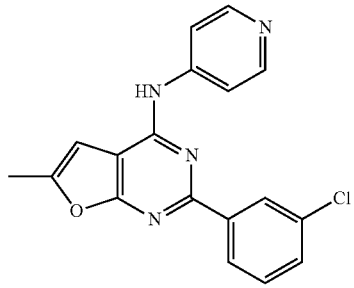

Preparation of 6-methyl4-(4-aminopyridyl)-2-chlorophenylfurano[3,2d]pyrimidine (18)

6-methyl4-chloro-2-chlorophenyl-furano[3,2d]pyrimidine (480 mg, 1.72 mmole, 1 eq), BINAP (8 mg, 0.013 mmole, 0.0075 eq), Pd$_2$(dba)$_3$ (3.9 mg, 0.0043 mmole, 0.0025 eq), sodium t-butoxide (231 mg, 2.4 mmole, 1.4 eq), 4-aminopyridine (194 mg, 2.06 mmole, 1.2 eq) were combined in 5 ml dioxane and heated to 50° C. for 5 hours. Product was isolated by preparative HPLC on C18 column.

Scheme E (Synthesis of compound 19)

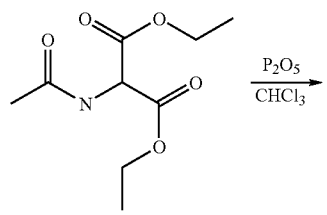

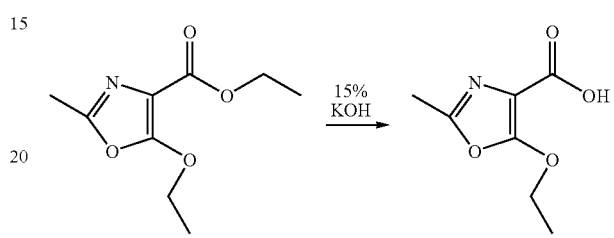

Preparation of 2-methyl-5-ethoxy-4-oxazole-4-carboxylic acid

Ethyl-2-methyl-5-ethoxy-4-oxazole-4-carboxylate (8.26 g, 41.5 mmol) was treated with 74 ml of a 15% solution of KOH. This was refluxed for 15 minutes then cooled and acidified using a 10% HCl solution. Product was collected by vacuum filtration.

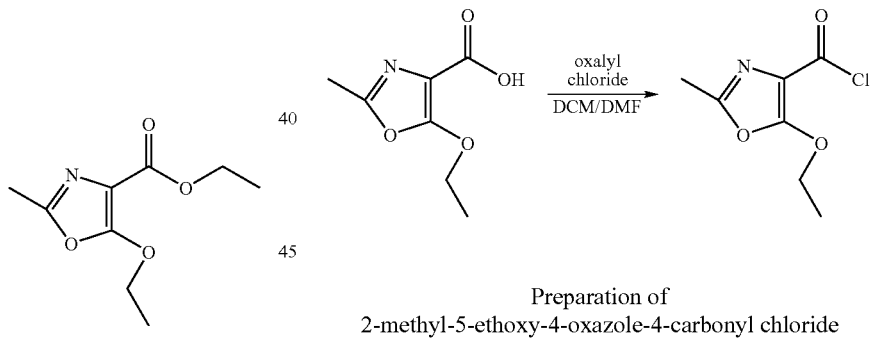

Preparation of 2-methyl-5-ethoxy-4-oxazole-4-carbonyl chloride 2-methyl-5-ethoxy-4-oxazole-4-carboxylic acid (2.56 g, 14.9 mmol) was dissolved in dichloromethane. Two drops of dimethylformamide was added and the reaction was cooled in an ice bath. Oxalyl chloride (12 ml, 22.3 mmol) was added dropwise. The ice bath was removed and the reaction was stirred at room temperature for 2 hours. Solvent was removed by reduced pressure.

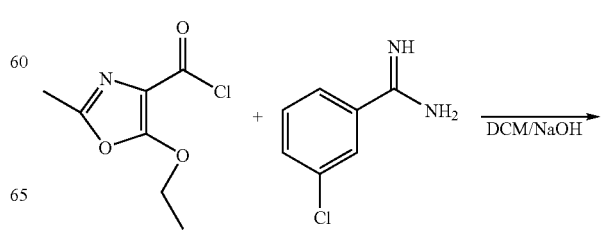

Preparation of Ethyl-2-methyl-5-ethoxy-4-oxazole-4-carboxylate

Diethyl Acetamidomalonate (15.0 g, 69.1 mmol) was dissolved in 60 ml of chloroform then treated with 60 g of phosphorous pentoxide. Reaction mixture was refluxed for 6 hours then cooled to room temperature. This solution was treated with sodium hydroxide (1 M) to neutralize the reaction mixture. The organic layer was washed with water and dried over sodium sulfate (anh). Crude product was vacuum distilled to isolate product. 8.26 g of product were obtained (60% yield).

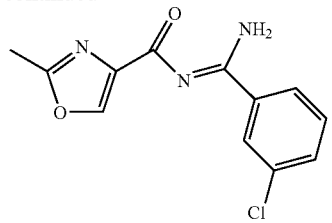

Preparation of 4-(3-chlorobenzamidinamide)-2-methyl-5-ethoxy-4-oxazole-4-carbonyl chloride 3-chlorobenzamidine (2.29 g, 14.8 mmol) was dissolved in 40 ml of DCM and brought to 0° C. A 15 ml 2.0 M solution of sodium hydroxide was then added. 2-methyl-5-ethoxy-4-oxazole-4-carbonyl chloride (2.8 g, 14.8 mmol), dissolved in 30 ml of DCM was added dropwise to the reaction mixture and stirred at room temperature for 3 hours. Organic solvent was then washed with water followed by sodium bicarbonate, then dried with sodium sulfate and concentrated.

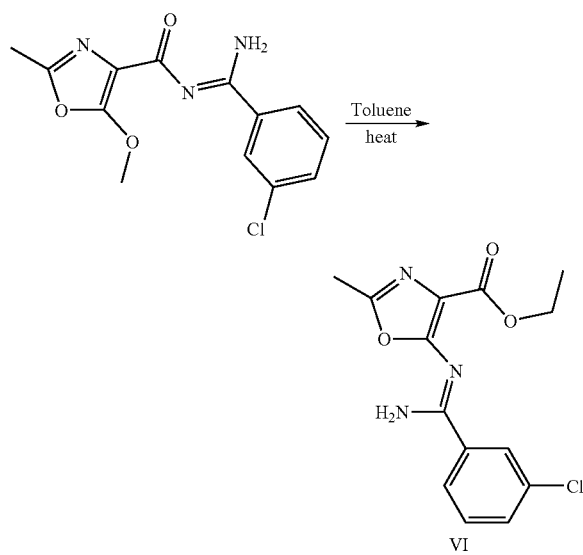

Preparation of Compound of Formula (VI):

4-(3-chlorobenzamidinamide)-2-methyl-5-ethoxy-4-oxazole-4-carbonyl chloride (2.0 g, 6.5 mmol) was dissolved in 30 ml of toluene and refluxed for 1.5 hours. The solvent was then removed by reduced pressure.

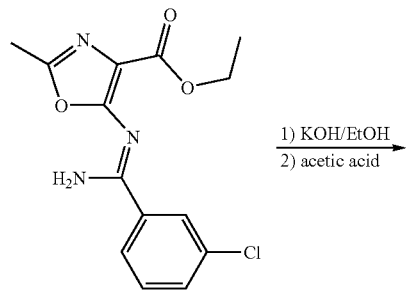

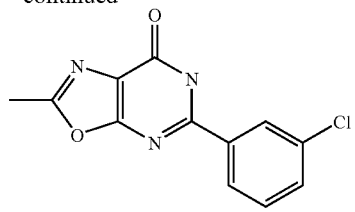

Preparation of 7-methyl-2-(3-chlorophenyl)-oxazolo[2,3d]pyrimidone 1.86 g, 5.93 mmol, of the oxazole ester was treated with 0.86 g, 15.4 mmol of KOH in 20 l of ethanol. This was stirred at room temperature overnight. The organic solvent was evaporated under reduced pressure and the compound was dissolved in water and acidified using a 15% solution of HCl. Solid product was collected by vacuum filtration.

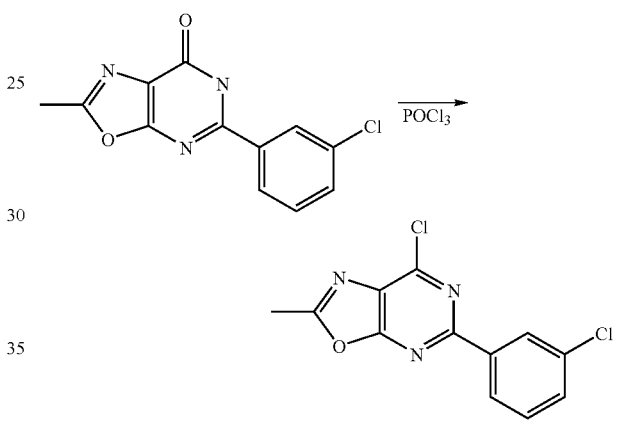

Preparation of 7-methyl-4-chloro-2-(3-chlorphenyl)-oxazolo[2,3d]pyrimidine 7-methyl-2-(3-chlorophenyl)-oxazolo[2,3d]pyrimidone (1.32 g, 5.06 mmol) was treated with phosphorus oxychloride (13.2 ml, 141.7 mmol and refluxed for three hours. Reaction was cooled, solvent was removed by reduced pressure and residue was taken up in chloroform. Ice was added to the organic solvent, then organic solvent was washed with sodium bicarbonate, dried over sodium sulfate and then concentrated. Crude product was purified by flash column chromatography.

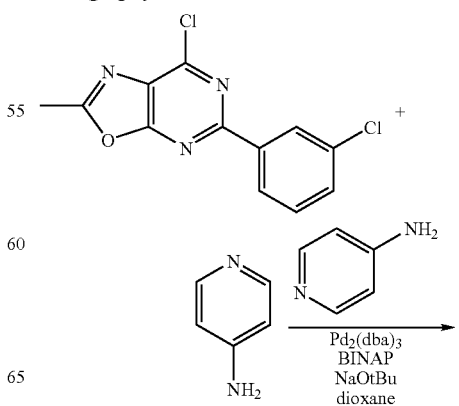

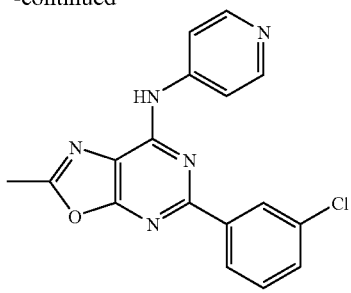

Preparation of 7-methyl-4-(4-aminopyridyl)-2-(3-chlorophenyl)oxazolo[2,3d]pyrimidine (19)

7-methyl-4-chloro-2-(3-chlorophenyl)-oxazolo[2,3 d]pyrimidine (0.100 g, 0.358 mmol), 4-aminopyridine (0.040 g, 0.430 mmol), sodium t-butoxide (0.048 g, 0.501 mmol), Bis(diphenylphosphino)-1,1'-binaphthyl (0.0009 g, 0.0014 mmol), and $Pd_2(dba)_3$ (0.0004 g, 0.0043 mmol) were combined and dissolved in 2 ml of dry dioxane and refluxed for 3.5 hours. Reaction was cooled, then filtered through Celite®, and then purified by HPLC.

temperature (r.t.) and the white precipitate was filtered and washed with cold ethyl acetate (2×20 ml). The crude residue was partitioned between chloroform and water. The aqueous layer was acidified to pH 4 and the product was extracted with chloroform (3×50 ml). The organic layers were combined, washed with brine, dried over $MgSO_4$, filtered and concentrated in vacuo to give a crude white solid (VI) (4.5 g, 60%) which was not further purified.

Preparation of Compound of Formula (VII):

A suspension of compound of formula (VI) (200 mg, 0.757 mmol) in $POCl_3$ (5 ml) was stirred under reflux for 1 h. The solution was then cooled to room temperature and concentrated under reduced pressure to give a white solid which was dissolved in dry methylene chloride. The solution was cooled to 0° C. and ice was added followed by sat. $NaHCO_3$. The organic layer was separated, washed with brine, dried ($MgSO_4$), filtered and evaporated in vacuo to provide a crude white solid which was not further purified.

Preparation of Compound of Formula (20): (General Buchwald Reaction Procedure):

The crude imino chloride compound of formula (VII) (210 mg, 0.76 mmol, 1 eq) was dissolved in dioxane (5 ml) and to this was added $Pd(OAc)_2$ (9 mg, 0.04 mmol, 0.05 eq) followed by BINAP (35 mg, 0.056 mmol, 0.075 eq), 4-amino- Scheme F

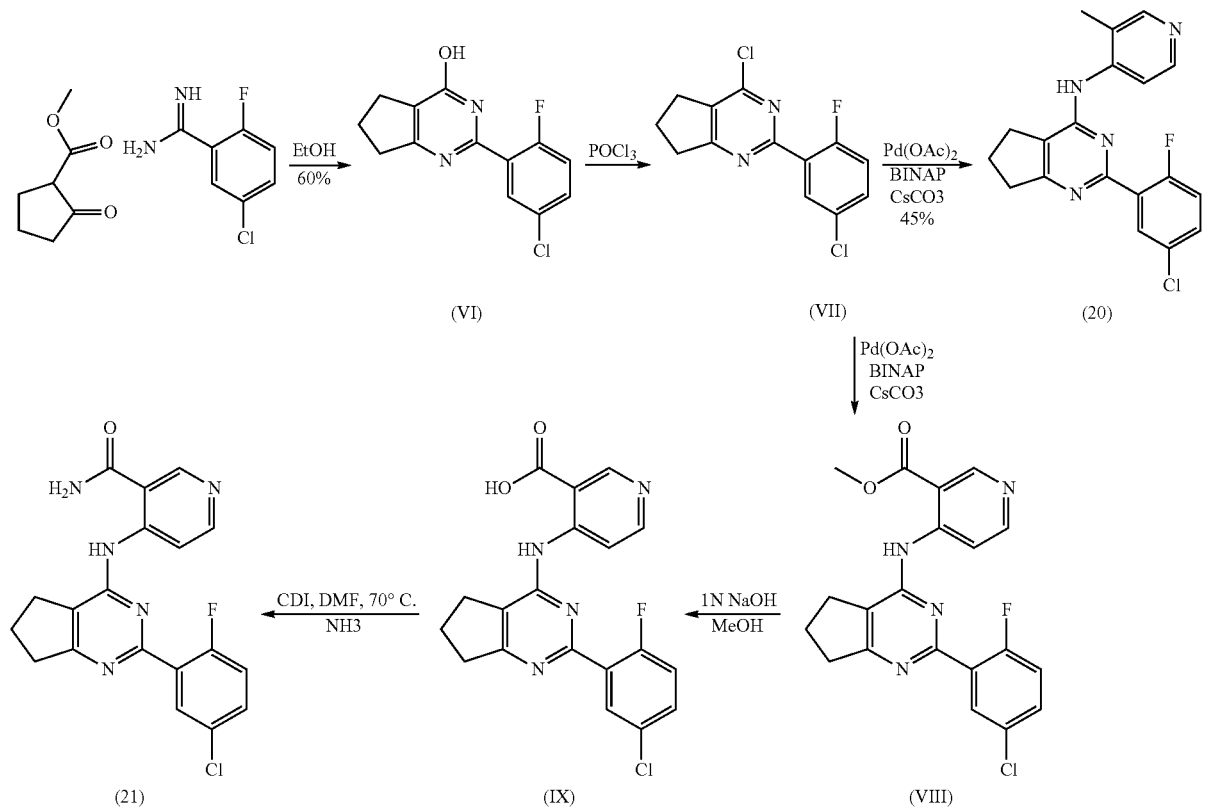

Preparation of Compound of Formula (VI):

To a solution of methyl-2-oxocyclopentane carboxylate (4.10 g, 28.9 mmol, 1 eq), in dry ethanol (20 ml) was added a solution of 2-fluoro-5-chlorobenzamidine (5.0 g, 28.9 mmol, 1 eq) in ethanol (20 ml) and the reaction mixture was heated to 80° C. overnight. The reaction mixture was cooled to room 3-picoline (82 mg, 0.760 mmol, 1 eq) and $Cs_2CO_3$ (370 mg, 1.13 mmol, 1.5 eq). The reaction mixture was heated to 80° C. for 15 h. The reaction mixture was cooled to r.t. and filtered through Celite® and the crude material was purified by flash column chromatography (3:2/ethyl acetate:hexane) to give compound of formula (20) (110 mg, 41%).

Preparation of Compound of Formula (IX):

To a suspension of compound of formula (VIII) (100 mg, 0.25 mmol, 1 eq) in MeOH (5 ml) was added a 1 N NaOH$_{(aq)}$ solution (500 μl, 0.50 mmol, 2 eq) and the reaction mixture was refluxed for 2 h. The mixture was cooled to r.t. and concentrated in vacuo. Water (10 ml) was added to the crude material and the aqueous layer was acidified to pH 4. The solid was filtered, washed with water (2×5 ml) and dried overnight to give compound of formula (IX) (50 mg, 52%) as a cream colored solid.

Preparation of Compound of Formula (21):

To a suspension of compound of formula (IX) (50 mg, 0.13 mmol, 1 eq) in dry DMF (2 ml) was added 1-1'-carbonyldiimidazole (42 mg, 0.26 mmol, 2 eq) and the reaction mixture was warmed to 70° C. for 2 h. The mixture was cooled to r.t. and NH$_{3(g)}$ was bubbled through for 10 min. The reaction mixture was stirred at r.t. for a further 1 h. The reaction was concentrated in vacuo. Water (10 ml) was added to the crude material and solid was filtered, washed with water (2×5 ml) and dried overnight to give compound of formula (21) (30 mg, 60%) as a cream colored solid.

Additional Compounds Prepared According to Scheme F

Compound of formula (32) was prepared according to the procedure outlined in scheme F, for the preparation of compound of formula (VIII), using 4-aminooyrdine-3-carboxylic acid ethyl ester. Compound of formula (36) was prepared by the method described for the synthesis of compound of formula (20) employing 4-amino-3-trifluoromethyl-picoline in place of 4-amino-3-picoline. Compound of formula (35) was prepared by the method described for the synthesis of compound of formula (21) employing methyl amine in place of ammonia. Compound of formula (37) was prepared by the method described for the synthesis of compound of formula (21) employing pyrrolidine in place of ammonia. Compound of formula (41) was prepared by the method described for the synthesis of compound of formula (21) employing cyclopropylamine in place of ammonia. Compound of formula (42) was prepared by the method described for the synthesis of compound of formula (21) employing cyclopropylmethylamine in place of ammonia. Compound of formula (51) was prepared by the method described for the synthesis of compound of formula (21) employing 2-amino-ethanol in place of ammonia. Compound of formula (52) was prepared by the method described for the synthesis of compound of formula (21) employing 1-amino-propan-2-(S)-ol in place of ammonia. Compound of formula (53) was prepared by the method described for the synthesis of compound of formula (21) employing 3-amino-propane 1,2(S)-diol in place of ammonia. Compound of formula (54) was prepared by the method described for the synthesis of compound of formula (21) employing HO—NH$_2$ in place of ammonia. Compound of formula (55) was prepared by the method described for the synthesis of compound of formula (21) employing 1-amino-propan-2-(R)-ol in place of ammonia. Compound of formula (56) was prepared by the method described for the synthesis of compound of formula (21) employing N-methylethylenediamine in place of ammonia. Compound of formula (58) was prepared by the method described for the synthesis of compound of formula (21) employing hydrazine in place of ammonia. Compound of formula (67) was prepared by the method described for the synthesis of compound of formula (21) employing benzamidine. Compound of formula (68) was prepared by the method described for the synthesis of compound of formula (21) employing methylamine in place of ammonia and benzamidine in place of 2-F, 3-Cl-benzamidine. Compound of formula (69) was prepared by the method described for the synthesis of compound of formula (21) employing N,N'-dimethyl-1,3-propanediamine in place of ammonia. Compound of formula (70) was prepared by the method described for the synthesis of compound of formula (21) employing 4-(3-aminopropyl)morpholine in place of ammonia. Compound of formula (71) was prepared by the method described for the synthesis of compound of formula (21) employing 1-(3-aminopropyl)imidazole in place of ammonia. Compound of formula (72) was prepared by the method described for the synthesis of compound of formula (21) employing 1-(3-aminopropyl)-2-pyrrolidinone in place of ammonia. Compound of formula (73) was prepared by the method described for the synthesis of compound of formula (21) employing 2-(2-aminoethyl)-1-methylpyrrolidine in place of ammonia. Compound of formula (74) was prepared by the method described for the synthesis of compound of formula (21) employing 1-(3-aminopropyl)-2-pipecoline in place of ammonia. Compound of formula (75) was prepared by the method described for the synthesis of compound of formula (21) employing 1-(2-aminoethyl)pyrrolidine in place of ammonia. Compound of formula (78) was prepared by the method described for the synthesis of compound of formula (21) employing 1-(2-aminoethyl)piperdine in place of ammonia. Compound of formula (79) was prepared by the method described for the synthesis of compound of formula (21) employing N,N-diethylethenediamine in place of ammonia.

Scheme G (Synthesis of Compound of formula (22), (24), (25), and (30))

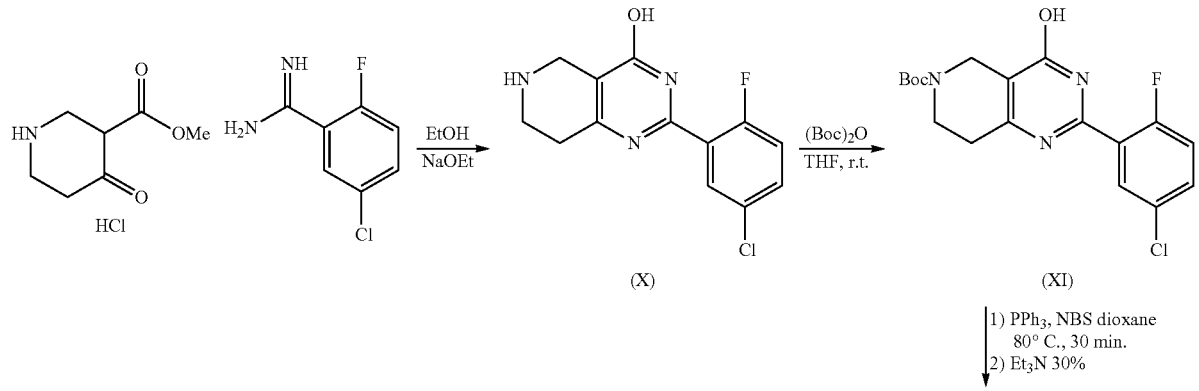

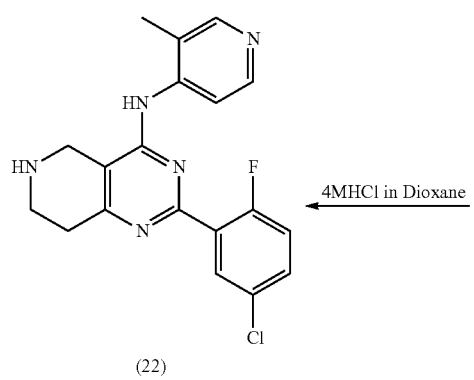 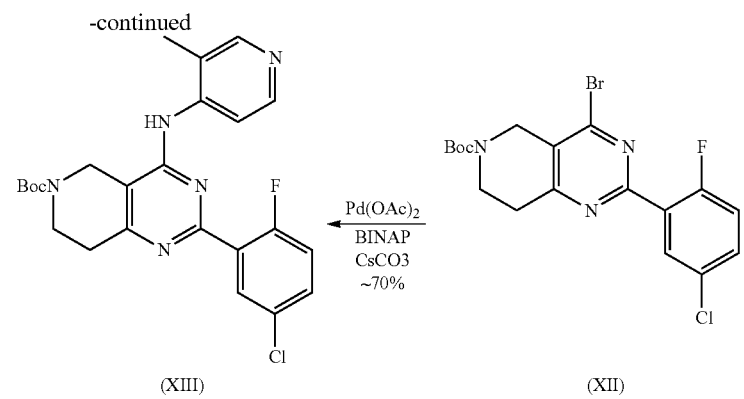

Preparation of Compound of Formula (X):
To a solution of 2-fluoro-5-chlorobenzamidine (1.79 g, 10.4 mmol, 1 eq) in EtOH (10 ml) was added solid NaOEt (705 mg, 10.4 mmol, 1 eq) followed by methyl-4-oxo-3-piperidine carboxylate.HCl (2.0 g, 10.4 mmol, 1 eq). The reaction mixture was heated to 70° C. for 2 h, then cooled to r.t. The precipitate was filtered and washed with ethyl acetate (2×20 ml) to give a white solid which (2.2 g, 76%) was not further purified.

Preparation of Compound of Formula (XI):
To a suspension of compound of formula (X) (300 mg, 1.08 mmol, 1 eq) in dry THF (10 ml) was added a solution of Boc₂O (258 mg, 1.18 mmol, 1.1 eq) in dry THF (10 ml) at r.t. The reaction mixture was stirred at r.t. for 2 h and then the solution was concentrated in vacuo to give a crude residue which was purified by flash column chromatography to give compound of formula (XI) (320 mg, 79%) as a white solid.

Preparation of Compound of Formula (XII):
To a solution of PPh₃ (813 mg, 3.03 mmol, 5 eq) in dry dioxane (20 ml) was added NBS (540 mg, 3.03 mmol, 5 eq) at once and the suspension was stirred at r.t. for 30 min. A solution of compound of formula (XI) (230 mg, 0.61 mmol, 1 eq) in dry dioxane (5 ml) was added and the reaction mixture was heated to 80° C. for 45 min. The reaction mixture was cooled to r.t. and Et₃N (160 µl, 1.21 mmol, 2 eq) was added. The mixture was concentrated in vacuo and the crude residue was purified by flash column chromatography (1:9 ethyl acetate:hexane) to give compound of formula (XII) (72 mg, 30%).

Preparation of Compound of Formula (XIII):
To a solution of compound of formula (XII) (72 mg, 0.16 mmol, 1 eq) in dry dioxane (2 ml) was added Pd(OAc)₂ (2 mg, 0.008 mmol, 0.05 eq) followed by BINAP (8 mg, 0.001 mmol, 0.075 eq), 4-amino-3-picoline (18 mg, 0.16 mmol, 1 eq) and Cs₂CO₃ (80 mg, 0.24 mmol, 1.5 eq). The reaction mixture was heated to 80° C. for 15 h. The reaction mixture was cooled to r.t. and filtered through Celite® and the crude material was purified by flash column chromatography (7:3/ethyl acetate:hexane) to give compound of formula (XIII) (65 mg, 85%).

Preparation of Compound of Formula (22):
To a solution of compound of formula (XIII) (65 mg, 0.14 mmol, 1 eq) in dry dioxane (2 ml) was added a 4 M HCl solution in dioxane (1 ml). The resultant suspension was stirred at r.t. for 2 h. The precipitate was filtered and washed with chloroform (1×5 ml), ethyl acetate (1×5 ml) and cold methanol (1×2 ml) to give compound of formula (22) (35 mg, 68%) as a white solid.

Preparation of Compound of Formula (24):
Compound of formula (24) was prepared according to the procedure outlined in scheme G, using ethyl 1-benzyl-4-oxopiperidine-3-carboxylate and benzamidine.

Preparation of Compound of Formula (25):
Compound of formula (25) was prepared according to the procedure outlined in scheme G, using benzamidine.

Preparation of Compound of Formula (30):
Compound of formula (30) was prepared according to the procedure outlined in scheme G, using ethyl 1-benzyl-4-oxopiperidine-3-carboxylate.

Scheme H (Synthesis of compound of formula (23))

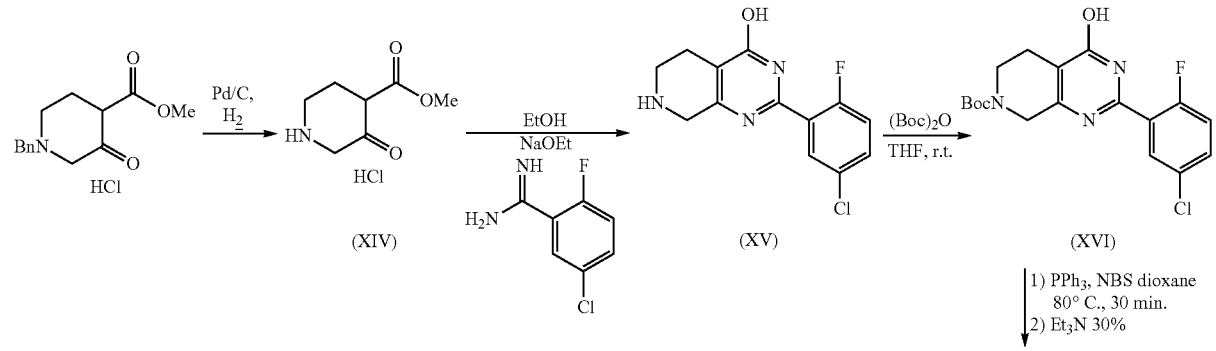

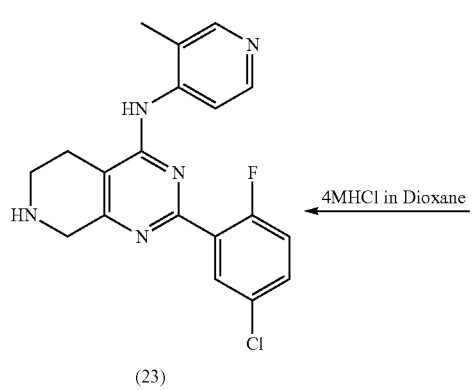

(23)

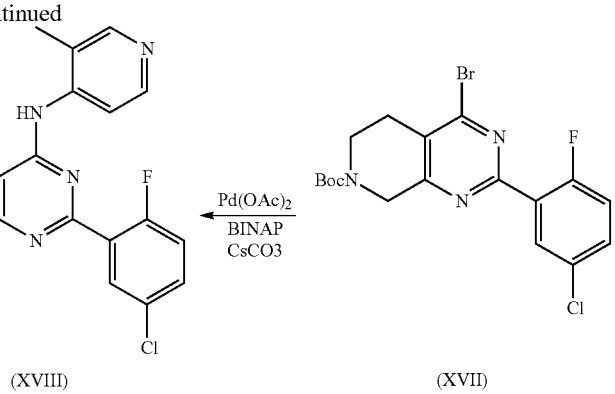

(XVIII)                    (XVII)

Preparation of Compound of Formula (XIV):

To a solution of ethyl-N-benzyl-3-oxo-4-piperdine carboxylate.HCl (2 g, 6.73 mmol, 1 eq) in ethanol (60 ml) was added 10% Pd/C. The air was evacuated and replaced with hydrogen via a balloon. The reaction mixture was left to stir at r.t. for 4 h. The reaction mixture was filtered through a short pad of Celite® to give compound of formula (XIV) which was not further purified.

Preparation of Compound of Formula (XV):

To a solution of 2-fluoro-5-chlorobenzamidine (1.16 g, 6.71 mmol, 1 eq) in EtOH (10 ml) was added solid NaOEt (457 mg, 6.71 mmol, 1 eq) followed by compound of formula (XIV) (1.39 g, 6.71 mmol, 1 eq). The reaction mixture was heated to 70° C. for 2 h and then cooled to r.t. The precipitate was filtered and washed with ethyl acetate (2×20 ml) to give compound of formula (XV) (1.12 g, 60%) as a white solid which was not further purified.

Preparation of Compound of Formula (XVI):

To a suspension of crude compound of formula (XV) (1.12 mg, 4.01 mmol, 1 eq) in dry THF (10 ml) was added a solution of Boc$_2$O (960 mg, 4.42 mmol, 1.1 eq) in dry THF (10 ml) at r.t. The reaction mixture was stirred at r.t. for 2 h and then the solution was concentrated in vacuo to give a crude residue which was purified by flash column chromatography to give compound of formula (XVI) (750 mg, 50%) as a white solid.

Preparation of Compound of Formula (XVII):

To a solution of PPh$_3$ (2.28 g, 8.70 mmol, 5 eq) in dry dioxane (20 ml) was added NBS (1.55 mg, 8.71 mmol, 5 eq) at once and the suspension was stirred at r.t. for 30 min. A solution of compound of formula (XVI) (660 mg, 1.74 mmol, 1 eq) in dry dioxane (5 ml) was added and the reaction mixture was heated to 80° C. for 45 min. The reaction mixture was cooled to r.t. and 2 eq of Et$_3$N were added. The mixture was concentrated in vacuo and the crude residue was purified by flash column chromatography (1:9 ethyl acetate:hexane) to give compound of formula (XVII) (230 mg, 30%).

Preparation of Compound of Formula (XVIII):

To a solution of compound of formula (XVII) (230 mg, 0.52 mmol, 1 eq) in dry dioxane (5 ml) was added Pd(OAc)$_2$ (6 mg, 0.03 mmol, 0.05 eq) followed by BINAP (8 mg, 0.004 mmol, 0.075 eq), 4-amino-3-picoline (67 mg, 0.62 mmol, 1.2 eq) and Cs$_2$CO$_3$ (271 mg, 0.83 mmol, 1.5 eq). The reaction mixture was heated to 80° C. for 15 h. The reaction mixture was cooled to r.t. and filtered through Celite® and the crude material was purified by flash chromatography (9:1/ ethyl acetate:hexane) to give compound of formula (XVIII) (38 mg, 16%).

Preparation of Compound of Formula (23):

To a solution of compound of formula (XVIII) (38 mg, 0.08 mmol, 1 eq) in dry dioxane (2 ml) was added a 4 M HCl solution in dioxane (1 ml). The resultant suspension was stirred at r.t. for 2 h. The precipitate was filtered and washed with chloroform (1×3 ml), ethyl acetate (1×3 ml) and cold methanol (1×1 ml) to give compound of formula (23) (32 mg, 95%) as a white solid.

Scheme I (Synthesis of compound of formula (27))

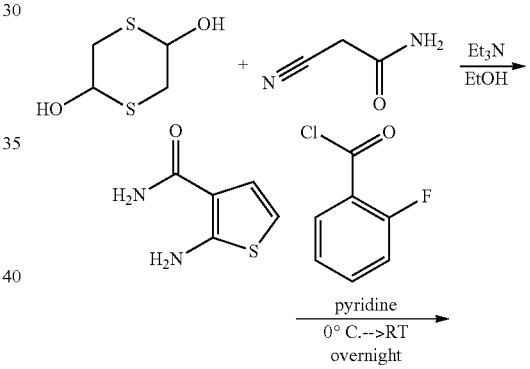

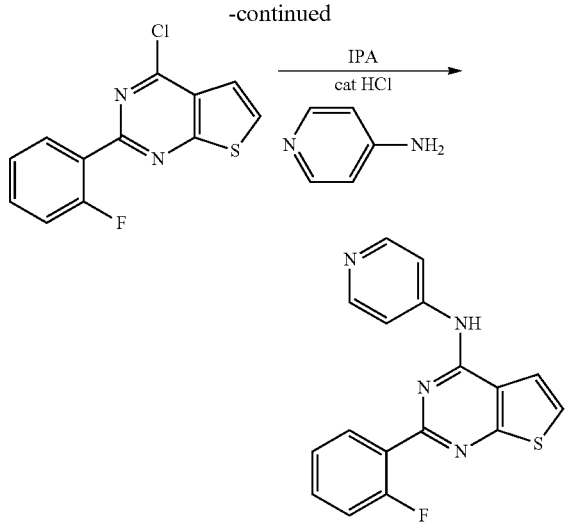

2-Amino-thiophene-3-carboxylic acid amide 1,4-dithian-2,5-diol (4.56 g, 30 mmole) and 2-cyanoacetamide (2.52 g, 30 mmole) were combined in ethanol (50 ml). Triethylamine (6 ml) was added and heated to 70° C. for 1 hour. The volume of solvent was reduced under vacuum, and the product was isolated by filtration. Product was recrystallized from ethanol to give 2.71 g of product (yield 64%).

2-(2-Fluoro-benzoylamino)-thiophene-3-carboxylic acid amide

2-Amino-thiophene-3-carboxylic acid amide (8.73 g, 61.4 mmole) was dissolved in pyridine (100 ml), cooled to 0° C., and 2-fluorobenzoyl chloride was added dropwise over 20 min, then the reaction was allowed to warm to room temperature with stirring overnight. The pyridine was removed under vacuum, dichloromethane and water were added. The product was precipitated as a grey solid and was washed with diluted hydrochloric acid, water and air dried. The dichloromethane layer was separated, washed with diluted hydrochloric acid, and water, dried over sodium sulfate (anh.) and the solvent was removed to give a total of 12.45 g product (77% yield).

2-(2-Fluoro-phenyl)-3H-thieno[2,3-d]pyrimidin-4-one 2-(2-Fluoro-benzoylamino)-thiophene-3-carboxylic acid amide (8.56 g, 32.4 mmole) was dissolved in a mixture of 20 ml 1 M sodium hydroxide and 60 ml ethanol. The mixture was brought to reflux for 4 hours. The reaction mixture was cooled and poured onto ice. The solution was acidified with dilute hydrochloric acid and the product was isolated by filtration. Upon vacuum drying 5.42 g of product was obtained (Yield: 68%).

4-Chloro-2-(2-fluoro-phenyl)-thieno[2,3-d]pyrimidine 2-(2-Fluoro-phenyl)-3H-thieno[2,3-d]pyrimidin-4-one (900 mg, 3.65 mmole) was dissolved in chloroform and thionyl chloride (0.532 ml, 7.30 mmole) was added to the mixture followed by 1 ml dimethylformamide. The reaction mixture was heated to reflux for 2.5 hours, the cooled mixture was washed with 10% sodium carbonate, the chloroform solution was dried over sodium sulfate (anh) and the solvent was removed. The crude product was chromatographed on silica gel, eluting with chloroform. Upon removal of solvent 438 mg of product was obtained (yield: 45%).

[2-(2-Fluoro-phenyl)-thieno[2,3-d]pyrimidin-4-yl]-pyridin-4-yl-amine

4-Chloro-2-(2-fluoro-phenyl)-thieno[2,3-d]pyrimidine (110 mg, 0.41 mmole) and 4-aminopyridine (78 mg, 0.830 mmole) were combined in isopropanol (3 ml), then 4 drops of 4 M HCl/dioxane were added and the reaction mixture was heated to 80° C. for 7 hours. The reaction mixture was cooled and the product was isolated by filtration, washed with minimum cold methanol and dried under vacuum to give 116 mg of product (yield: 86%).

Scheme J (Synthesis of compound of formula (28))

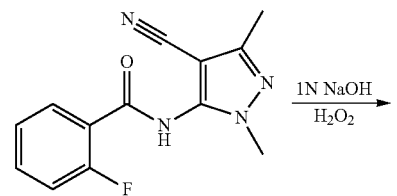

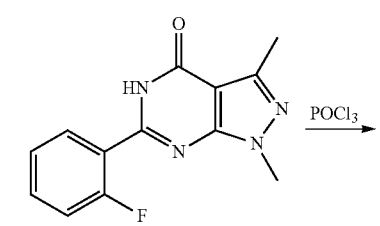

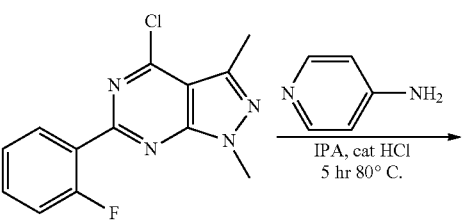

-continued

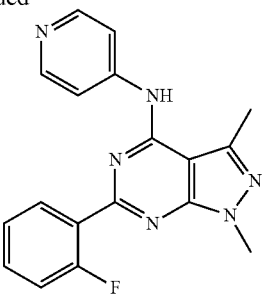

5-Amino-1,3-dimethyl-1H-pyrazole-4-carbonitrile

Methylhydrazine (5 g, 108.5 mmole) was added dropwise to a solution of (1-ethoxy-ethylidene)-malonitrile (14.7 g, 108.5 mmole) in 250 ml ethanol. The mixture was then heated to reflux for 2.5 hours. The reaction mixture was allowed to cool, the volume was reduced to about 70 ml and the product was isolated by filtration, washed with cold ethanol and dried to obtain 13.5 g of product (yield: 91%).

N-(4-Cyano-2,5-dimethyl-2H-pyrazol-3-yl)-2-fluoro-benzamide

5-Amino-1,3-dimethyl-1H-pyrazole-4-carbonitrile (10 g, 73.4 mmole) was suspended in pyridine (90 ml) and 2-fluorobenzoyl chloride was added dropwise while cooling the reaction mixture on an ice bath. The mixture reaction was stirred overnight at room temperature. Most of the pyridine was removed and 100 ml of cold water was added to precipitate the product. The product was isolated by filtration, washed with cold water and a small amount of cold ethanol, and dried under vacuum to obtain 9.15 g of product (yield: 50%).

6-(2-Fluoro-phenyl)-1,3-dimethyl-1,5-dihydro-pyrazolo[3,4-d]pyrimidin-4-one

N-(4-Cyano-2,5-dimethyl-2H-pyrazol-3-yl)-2-fluoro-benzamide (5.0 g, 19.36 mmole) was suspended in 38 ml 1M sodium hydroxide and heated to 90° C. for 3 hours followed by addition of 30% hydrogen peroxide (10 ml) and further heating overnight. The reaction mixture was cooled to room temperature and acidified with dilute hydrochloric acid. The product was isolated by filtration, washed with water, and dried overnight under vacuum to obtain 3.39 g of product. (Yield 67%).

4-Chloro-6-(2-fluoro-phenyl)-1,3-dimethyl-1H-pyrazolo[3,4-d]pyrimidine 6-(2-Fluoro-phenyl)-1,3-dimethyl-1,5-dihydro-pyrazolo[3,4-d]pyrimidin-4-one (2.0 g, 7.74 mmole) was treated with 40 ml phosphorous oxychloride and heated to reflux overnight. The excess phosphorous oxychloride was removed under vacuum and ice water was added to the residue. The product was extracted with ethyl acetate, washed with 10% sodium carbonate, water, dried over sodium sulfate (anh) and the solvent was removed to give crude product. Crude product was chromatographed on silica gel column eluting with chloroform to give 1.10 g of pure product (yield: 51%).

[6-(2-Fluoro-phenyl)-1,3-dimethyl-1H-pyrazolo[3,4-d]pyrimidin-4-yl]-pyridin-4-yl-amine 4-Chloro-6-(2-fluoro-phenyl)-1,3-dimethyl-1H-pyrazolo[3,4-d]pyrimidine (84 mg, 0.304 mmole) and 4-aminopyridine (57 mg, 0.608 mmole) were combined in 4 ml isopropanol, 3 drops 4M HCl/dioxane were added and the reaction mixture heated to 80° C. for 5 hours. The reaction mixture was cooled and the product was filtered to obtain 83 mg after vacuum drying (yield: 81%).

Scheme K (Synthesis of compound of formula (29))

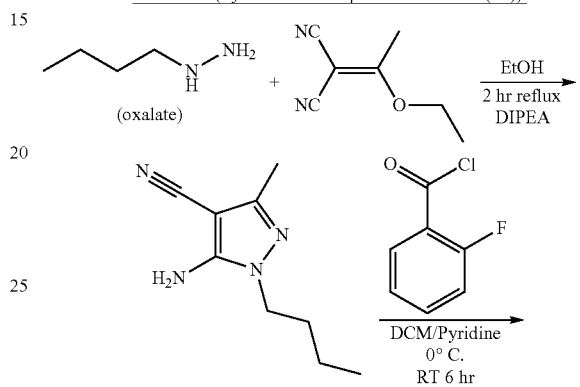

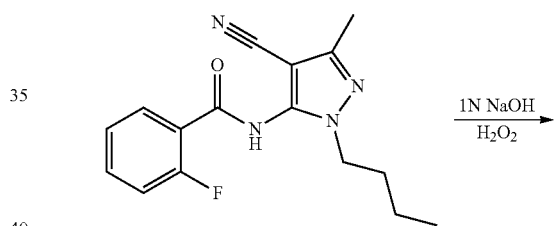

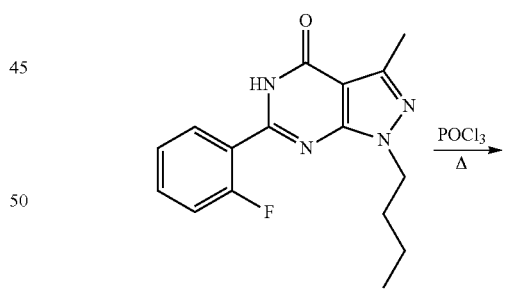

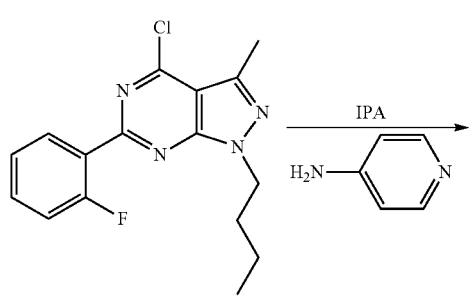

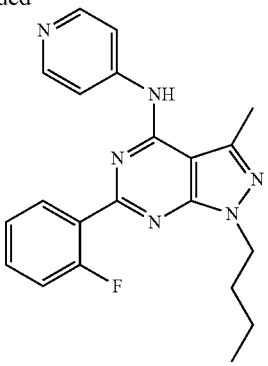

5-Amino-1-butyl-3-methyl-1H-pyrazole-4-carbonitrile

Butylhydrazine oxalate (14.25 g, 80 mmole) and (1-Ethoxyethylidine)-malonitrile (10.82 g, 80 mmole) were combined in ethanol (200 ml), and the mixture was treated with diisopropylethylamine (10.39 g, 80 mmole). The mixture was refluxed for 2 hours, then stirred at room temperature overnight. Most of the solvent was removed under vacuum and triturated with chloroform, some solid was filtered, and the chloroform filtrate was kept. The chloroform filtrate was washed with water, dried over sodium sulfate (anh) and the solvent was removed to give the product as a solid, 13.13 g (yield: 74%).

N-(2-Butyl-4-cyano-5-methyl-2H-pyrazol-3-yl)-2-fluoro-benzamide

5-Amino-1-butyl-3-methyl-1H-pyrazole-4-carbonitrile (10.0 g, 56 mmole) was dissolved in a mixture of dichloromethane/pyridine (45 ml/15 ml) and cooled to 0° C. 2-fluorobenzoyl chloride (8.87 g, 56 mmole) was added dropwise and the reaction mixture was stirred for 1 hour at 0° C., and at room temperature overnight. The solvent was removed under vacuum. The residue was taken up in ethyl acetate, washed with diluted hydrochloric acid, 0.1 M sodium hydroxide, and water, and dried over sodium sulfate (anh). The solvent was removed and the solid triturated in 30% ethyl acetate/hexanes. The product was filtered to obtain 4.16 g product (yield: 24%).

1-Butyl-6-(2-fluoro-phenyl)-3-methyl-1,5-dihydro-pyrazolo[3,4-d]pyrimidin-4-one

N-(2-Butyl-4-cyano-5-methyl-2H-pyrazol-3-yl)-2-fluoro-benzamide (4.0 g, 13.3 mmole) was suspended in 26 ml 1M sodium hydroxide, and 30% hydrogen peroxide (10 ml) and ethanol (5 ml) were added. The reaction mixture was heated to reflux for 4 hours, then more 30% hydrogen peroxide (10 ml) was added and heated to reflux overnight. The reaction mixture was cooled and acidified with diluted hydrochloric acid to pH 6.0. The product was collected by filtration and dried under vacuum to obtain 1.29 g of product (yield: 32%).

1-Butyl-4-chloro-6-(2-fluoro-phenyl)-3-methyl-1H-pyrazolo[3,4-d]pyrimidine

1-Butyl-6-(2-fluoro-phenyl)-3-methyl-1,5-dihydro-pyrazolo[3,4-d]pyrimidin-4-one (1.23 g, 4.1 mmole) was dissolved in phosphorous oxychloride (15 ml) and heated to reflux overnight. The excess phosphorous oxychloride was removed under vacuum, the residue was treated with ice water, the product was extracted into ethyl acetate, washed with water, saturated sodium chloride, then dried over sodium sulfate (anh.) and the solvent was removed to give the crude product. The product was chromatographed on silica gel eluting with chloroform to give 723 mg of purified product (yield: 55%).

[1-Butyl-6-(2-fluoro-phenyl)-3-methyl-1H-pyrazolo[3,4-d]pyrimidin-4-yl]-pyridin-4-yl-amine 1-Butyl-4-chloro-6-(2-fluoro-phenyl)-3-methyl-1H-pyrazolo[3,4-d]pyrimidine (100 mg, 0.31 mmole) and 4-aminopyridine (58 mg, 0.626 mmole) were combined in ethyleneglycol dimethoxy ether and heated to reflux for 4 hours. The reaction mixture was cooled and the product was isolated by filtration, washed with minimum cold solvent and dried to give 132 mg of product. 50 mg of this material was subjected to HPLC purification on reversed phase C18 column, eluting with gradient of water/acetonitrile/0.1% trifluoroacetic acid.

Scheme L (Synthesis of compound of formula (9))

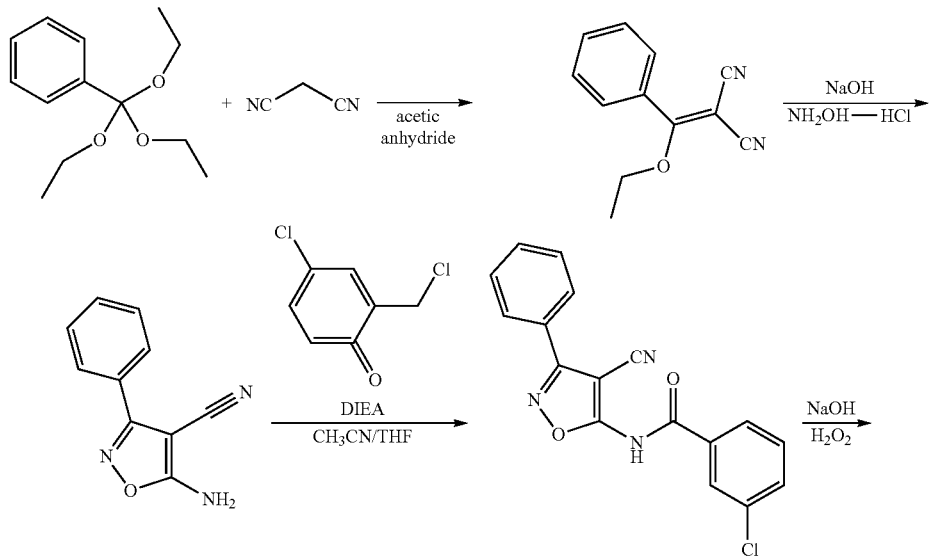

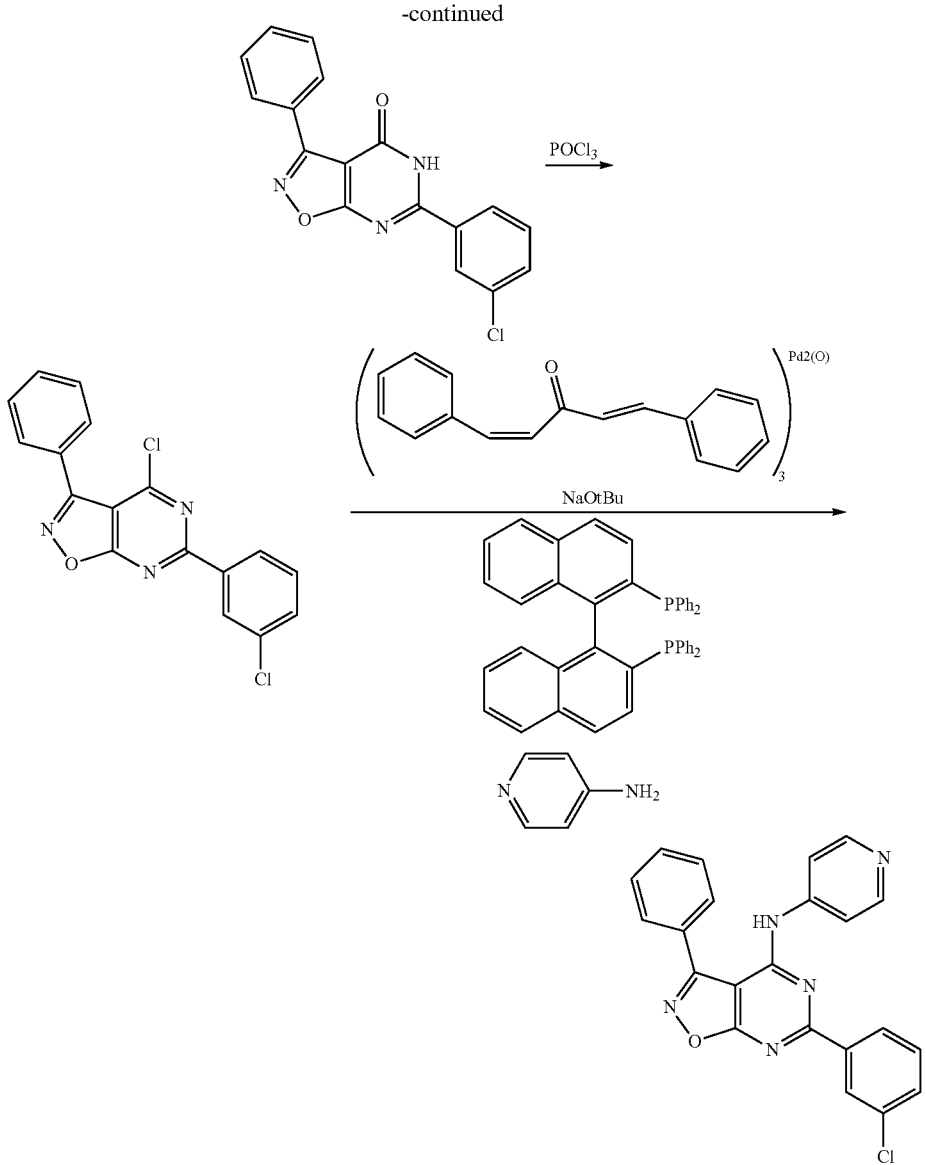

2-(Ethoxy-phenyl-methylene)-malononitrile

Triethylorthobenzoate (25 g, 0.112 mole), malonitrile (9.07 g, 0.137 mole and acetic anhydride (50 ml) were brought to reflux overnight. The excess acetic anhydride was removed under vacuum and the product was chromatographed over silica gel eluting with 30% ethylacetate/hexanes to give 21.7 g of product (yield: 97%).

5-Amino-3-phenyl-isoxazole-4-carbonitrile

Hydroxylamine hydrochloride was suspended in water (30 ml) and sodium hydroxide (4.4 g, 0.11 mole) and then ethanol (40 ml) was added, followed by batchwise addition of 2-(ethoxy-phenyl-methylene)-malononitrile (21.7 g, 0.11 mole). The reaction mixture was heated to 50° C. for 2 hours. The ethanol was removed under vacuum and the precipitate was filtered. The precipitate was redissolved in 50% ethyl acetate/hexanes and chromatographed on silica gel to give 8.2 g of product after removal of solvent (yield: 40%). The rest of the sequence was made by analogy to the methyl replacement of the phenyl analog.

Scheme M (Synthesis of compound of formula (80))

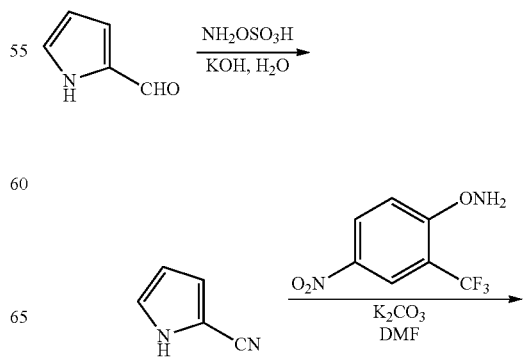

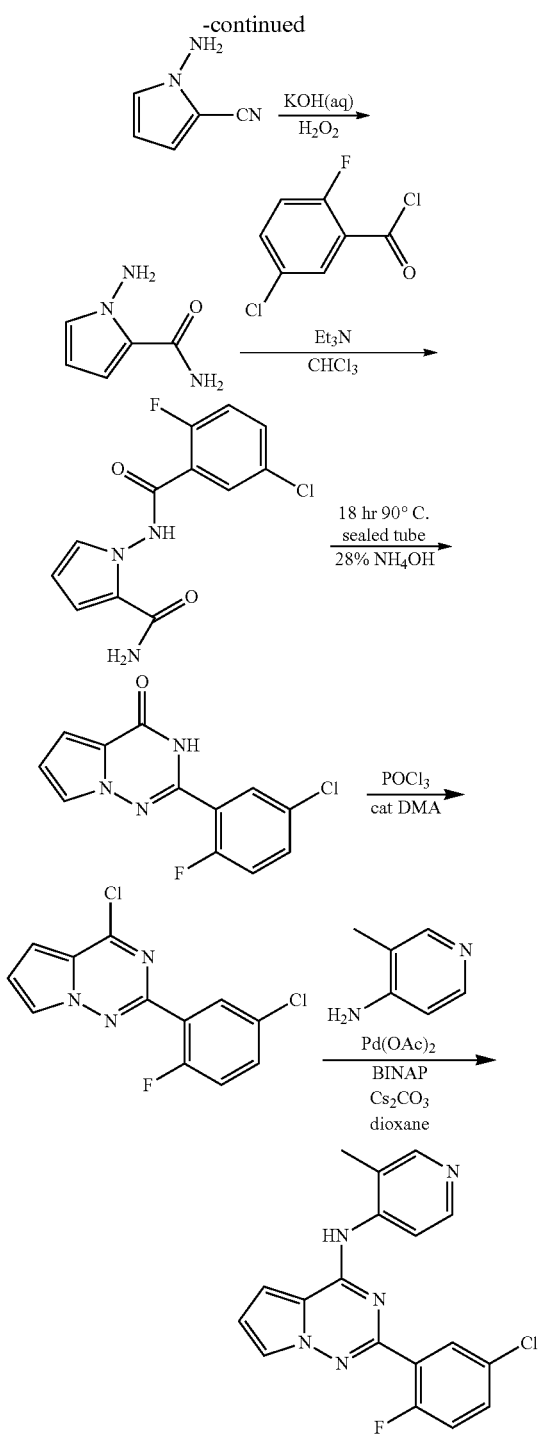

ml), the extract was dried over sodium sulfate (anh.). The solvent was removed to give 3.36 g of product as a liquid (yield: 100%).

1-Amino-1H-pyrrole-2-carbonitrile

1H-Pyrrole-2-carbonitrile (3.36 g, 36.5 mmole) was dissolved in 100 ml dimethyl-formamide to which potassium carbonate (7.51 g, 54.75 mmole) was added followed by O-(4-Nitro-2-trifluoromethyl-phenyl)-hydroxylamine (12.15 g, 54.73 mmole). The mixture was stirred at room temperature overnight. 80 ml water was added and the precipitate was filtered. The pH of the filtrate was adjusted to 10, and extracted with ethyl acetate (3×100 ml). The extract was washed with water, saturated sodium chloride and dried over sodium sulfate. The solvent was removed under vaccum to give 6.31 g product containing residual dimethyl formamide. The yield was estimated by NMR at 64%.

1-Amino-1H-pyrrole-2-carboxylic acid amide

1-Amino-1H-pyrrole-2-carbonitrile (2.52 g, 23.5 mmole) was suspended in 75 ml water, treated with potassium hydroxide (32 g, 0.57 mole), 30% hydrogen peroxide (2 ml) and stirred overnight at room temperature. The reaction mixture was cooled to 0° C. for 30 min and the product was isolated by filtration, washed with cold water and dried under vacuum to give 2.55 g of product (yield: 87%).

1-(5-Chloro-2-fluoro-benzoylamino)-1H-pyrrole-2-carboxylic acid amide

1-Amino-1H-pyrrole-2-carboxylic acid amide (1.25 g, 10 mmole) was partially dissolved in 45 ml acetonitrile, triethylamine (1.39 ml, 10 mmole) was added followed by dropwise addition of 5-chloro-2-fluorobenzoyl chloride (1.93 g, 10 mmole) in 3 ml chloroform. The reaction mixture was stirred at room temperature overnight, the solvent was removed under vacuum and the residue was taken up in chloroform, washed with 10% sodium bicarbonate, water, and dried over sodium sulfate (anh.). A solid crystallized from solution upon standing. Additional product was obtained by chromatographing the filtrate on silica gel eluting with 3% methanol/chloroform. 600 mg of product was obtained (yield: 21%).

2-(5-Chloro-2-fluoro-phenyl)-3H-pyrrolo[21-f][1,2,4]triazin-4-one 1-(5-Chloro-2-fluoro-benzoylamino)-1H-pyrrole-2-carboxylic acid amide (200 mg, 0.71 mmole) was dissolved in 5 ml of 28% ammonium hydroxide in a sealed tube and heated to 80° C. overnight. The solution was purged with nitrogen to remove excess ammonia, and acidified with 1M hydrochloric acid to pH 2. The product was isolated by filtration, washed with water and vacuum dried to give 90 mg product (yield: 48%).

4-Chloro-2-(5-chloro-2-fluoro-phenyl)-pyrrolo[2,1-f][1,2,4]triazine 2-(5-Chloro-2-fluoro-phenyl)-3H-pyrrolo[2,1-f][1,2,4]triazin-4-one (60 mg, 0.228 mmole) was added to phosphorous oxychloride (1 ml). 57 microliters N,N-dimethylaniline (catalyst) were added and heated to 110° C. overnight. The excess phosphorous oxychloride was removed under vacuum, and the residue was treated with ice, and the product extracted with chloroform. The chloroform extract was dried 1H-Pyrrole-2-carbonitrile Pyrrole-2-carboxaldehyde (3.00 g, 0.0316 mole) was combined with hydroxylamine-O-sulfonic acid (12.5 g, 0.11 mole) in 100 ml water and stirred at room temperature overnight. The reaction mixture was cooled to 0° C. and a solution of potassium hydroxide (12.06 g, 0.603 mole) in 80 ml water was added dropwise over 1 hour time period. The reaction mixture was stirred at room temperature for 3 hours. The reaction mixture was extracted with dichloromethane (3×100 over sodium sulfate (anh.) and the solvent was removed to give crude product. The product was purified by silica gel chromatography eluting with chloroform to give 36 mg of product (yield: 56%).

[2-(5-Chloro-2-fluoro-phenyl)-pyrrolo[2,1-f][1,2,4]triazin-4-yl]-(3-methyl-pyridin-4-yl)-amine 4-Chloro-2-(5-chloro-2-fluoro-phenyl)-pyrrolo[2,1-f][1,2,4]triazine (30 mg, 0.106 mmole), cesium carbonate (48.5 mg, 0.149 mmole), palladium (II) acetate (1.19 mg, 0.0053 mmole), BINAP (4.96 mg, 0.0080 mmole), and 4-aminopicoline (13.8 mg, 0.128 mmole) were combined in 4 ml dioxane (anh.) and heated to 90° C. with stirring overnight. The reaction mixture was filtered to remove solid material, the filtrate was evaporated to dryness, the residue was dissolved in chloroform (8 ml), washed with 0.5 M sodium hydroxide (1 ml), dried over sodium sulfate (anh.), evaporated to dryness, and then the residue was redissolved in dimethylformamide and purified by reversed phase HPLC. The product was isolated.

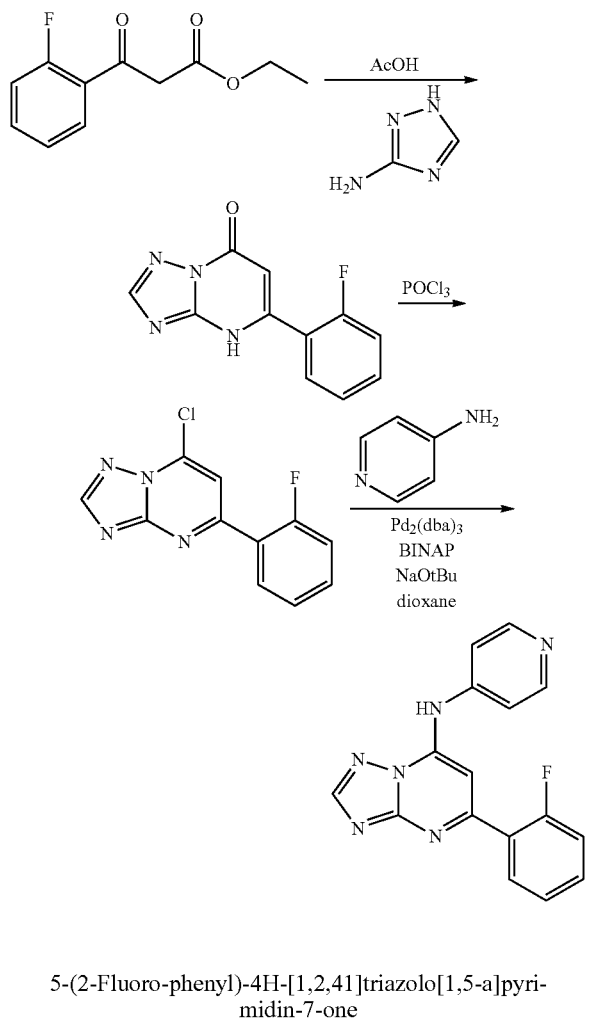

Scheme N (Synthesis of compounds of formula (81) and (82))

5-(2-Fluoro-phenyl)-4H-[1,2,4]triazolo[1,5-a]pyrimidin-7-one 3-amino-1,2,4-triazole (3.64 g, 43.25 mmole) and ethyl 2-fluorobenzoyl acetate (10 g, 47.57 mmole) were combined in acetic acid (45 ml) and heated to reflux overnight. The reaction mixture was cooled and the product was filtered, washed with diethyl ether to give 3.47 g (yield: 35%).

7-Chloro-5-(2-fluoro-phenyl)-[1,2,4]triazolo[1,5-a]pyrimidine 5-(2-Fluoro-phenyl)-4H-[1,2,4]triazolo[1,5-a]pyrimidin-7-one (840 mg, 3.64 mmole) was suspended in phosphorous oxychloride (5 ml) and heated to reflux for 45 min. The excess phosphorous oxychloride was removed under vacuum, the residue was treated with ice, the product was extracted with chloroform, then the chloroform was washed with 10% sodium bicarbonate, dried over sodium sulfate and the solvent was removed under vacuum to give 420 mg of product (yield 46%).

[5-(2-Fluoro-phenyl)-[1,2,4]triazolo[1,5-a]pyrimidin-7-yl]-pyridin-4-yl-amine

7-Chloro-5-(2-fluoro-phenyl)-[1,2,4]triazolo[1,5-a]pyrimidine (124 mg, 0.5 mmole) was suspended in dioxane (5 ml), 4-aminopyridine (56.4 mg, 0.6 mmole), sodium t-butoxide (67 mg, 0.7 mmole), BINAP (2.3 mg, 0.00375 mmole), and $Pd_2(dba)_3$ (1.14 mg, 0.00125 mole) were added and heated to 90° C. overnight. Dioxane was removed under vacuum, the residue was taken up in methanol, filtered and purified by reversed phase HPLC, and the fractions were lyophilized to obtain product as trifluoroacetate salt.

Compound of formula (81) was prepared using a procedure similar to the one described above, using ethyl 5-chloro-2-fluorobenzoyl acetate. Compound of formula (83) was prepared using a procedure similar to the one described above, using 4-amino-pyrimidine.

Scheme O (Synthesis of compound of formula (60) and (61))

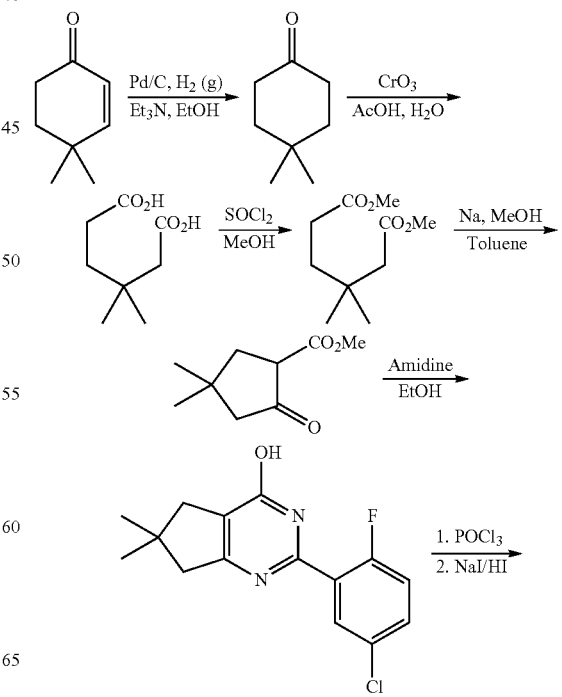

-continued

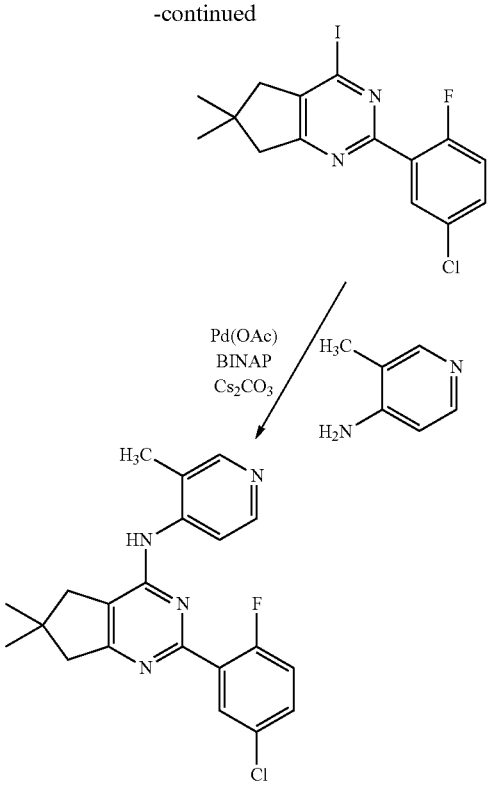

Preparation of 4,4-Dimethylcyclohexanone

Ref: *Tetrahedron Lett.*, 1992, 33(35), 5009.

A solution of 4,4-dimethylcyclohexen-2-one (10 g, 78.11 mmol) and triethylamine (10.89 mL, 78.11 mmol) in 100% ethanol (30 mL) was subjected to hydrogenation at 30 psi in a Parr apparatus, at r.t. overnight. Filtration of the contents through Celite® and evaporation of the filtrate gave clean product as a colorless oil (10.08 g, 99% yield).

Preparation of 3,3-Dimethylhexanedioic acid

Ref: *J. Med. Chem.* 1970, 13(3),531.

To a solution of 4,4-dimethylcyclohexanone (2 g, 15.85 mmol) in glacial AcOH (100 mL) was added a solution of $CrO_3$ (4.75 g, 47.54 mmol) in glacial AcOH (20 mL) and water (20 mL). The mixture was stirred at 60° C. overnight, then cooled and diluted with 40% aq. NaOH to pH 14. The mixture was washed with diethyl ether (4×100 mL), and the aqueous layer was re-acidified with conc. HCl (aq.) to pH 1. The solution was extracted with diethyl ether (4×100 mL); the organic extracts were dried (brine and $MgSO_4$) and evaporated to give crude diacid that was esterified directly.

Preparation of 3,3-Dimethylhexanedioic acid dimethyl ester

The crude 3,3-Dimethylhexanedioic acid was dissolved in methanol (50 mL) and thionyl chloride (1 mL) was added and the solution heated at 60° C. for 6 h, then it was cooled and evaporated to give the crude diester, which was purified by chromatography (1:1 hexane/ethyl acetate) to give the pure product as a colorless oil (2.90 g, 91% yield over 2 steps).

Preparation of 4,4-Dimethyl-2-oxo-cyclopentanecarboxylic acid methyl ester

Ref: *J. Chem. Soc. Perkin Trans.* 1, 1984, 799.

To a solution of 3,3-Dimethylhexanedioic acid dimethyl ester (2.90 g, 14.36 mmol) and methanol (100 µL) in dry toluene (10 mL) was added sodium metal (0.66 g, 28.72 mmol). The mixture was heated to reflux overnight, then cooled and evaporated. The residue was purified by chromatography (1:1 hexane/ethyl acetate) to give the desired cyclized product as a colorless oil (2.08 g, 85% yield).

Preparation of 2-(5-Chloro-2-fluoro-phenyl)-6,6-dimethyl-6,7-dihydro-5H-cyclopentapyrimidin-4-ol A solution of 4,4-Dimethyl-2-oxo-cyclopentanecarboxylic acid methyl ester (2.08 g, 12.21 mmol) and 5-Chloro-2-fluoro-benzamidine (2.32 g, 13.44 mmol) in 100% ethanol (40 mL) was heated to reflux overnight, then cooled and evaporated. The residue was dissolved in 1N (aq.) NaOH (50 mL) and washed with methylene chloride (2×50 mL). The aqueous layer was then acidified with glacial acetic acid to pH 4 and extracted with methylene chloride (2×100 mL). The organic extracts were dried (brine and $MgSO_4$) and evaporated to give crude product, which was purified by chromatography ($CH_2Cl_2$, 0-10% MeOH) to give the desired product as a cream solid (2.10 g, 59% yield).

Preparation of 2-(5-Chloro-2-fluoro-phenyl)-4-iodo-6,6-dimethyl-6,7-dihydro-5H-cyclopentapyrimidine A suspension of 2-(5-Chloro-2-fluoro-phenyl)-6,6-dimethyl-6,7-dihydro-5H-cyclopentapyrimidin-4-ol (2.10 g, 7.16 mmol) in phosphorus oxychloride (40 mL) was heated to reflux for 2 h, then cooled and evaporated. The residue was dissolved in methylene chloride and the solution filtered through a short pad of silica gel. The filtrate was evaporated to give a residue that was suspended in hydriodic acid (10 mL) and heated at 90° C. with sodium iodide (5.37 g, 35.82 mmol) for 3 h. The mixture was cooled and diluted with water (50 mL). Aqueous sodium thiosulfate solution (50 mL) was added and the mixture was shaken with methylene chloride (3×100 mL). The organic extracts were dried over $MgSO_4$ and evaporated to give crude product, which was purified by flash chromatography ($CH_2Cl_2$) to give the desired iodo product as a cream solid (1.75 g, 66% yield).

Preparation of [2-(5-Chloro-2-fluoro-phenyl)-6,6-dimethyl-6,7-dihydro-5H-cyclopentapyrimidin-4-yl]-(3-methyl-pyridin-4-yl)-amine To a solution of 2-(5-Chloro-2-fluoro-phenyl)-4-iodo-6,6-dimethyl-6,7-dihydro-5H-cyclopentapyrimidine (100 mg, 0.25 mmol), 3-Methyl-pyridin-4-ylamine (30 mg, 0.27 mmol), Pd(OAc)$_2$ (3 mg, 12.42 µmol) and Rac-BINAP (12 mg, 18.63 µmol) in dry dioxane (3 mL) was added $Cs_2CO_3$ (121 mg, 0.37 mmol). The mixture was heated for 48 h at 85° C., cooled and evaporated. HPLC purification gave, after lyophilization, the desired product of formula (60) as the TFA salt, which was a white solid (6.4 mg). The same procedure was used to prepare compound of formula (61).

Scheme P (Synthesis of compounds of formula (62) to (66))

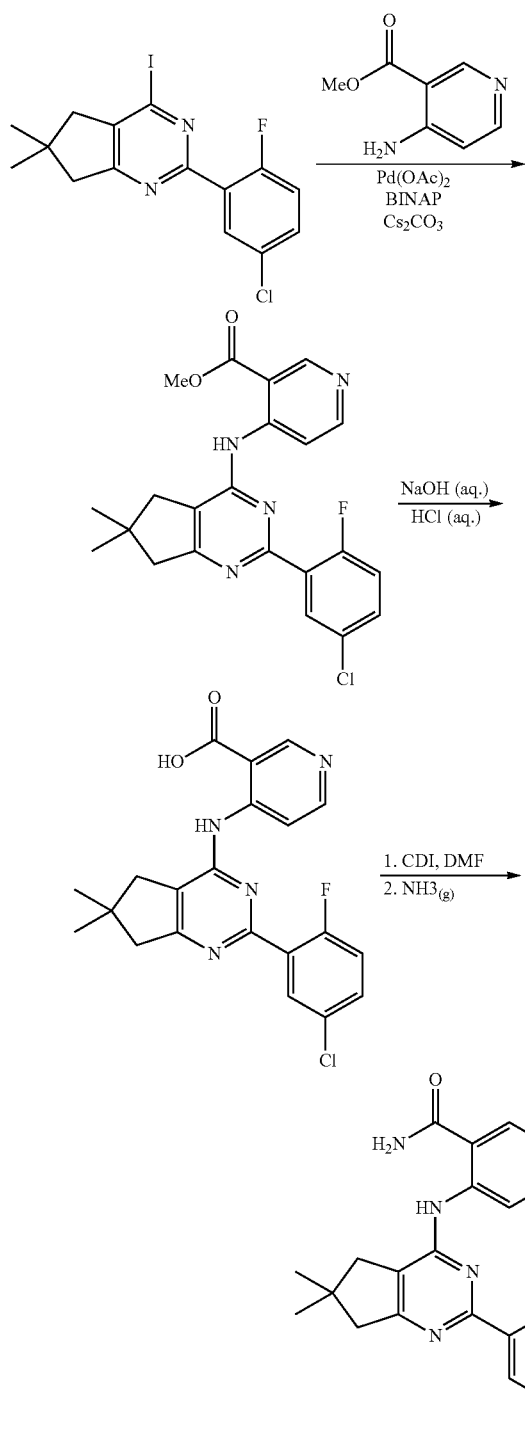

Preparation of 4-[2-(5-Chloro-2-fluoro-phenyl)-6,6-dimethyl-6,7-dihydro-5H-cyclopentapyrimidin-4-ylamino]-nicotinic acid methyl ester To a solution of 2-(5-Chloro-2-fluoro-phenyl)-4-iodo-6,6-dimethyl-6,7-dihydro-5H-cyclopentapyrimidine (500 mg, 1.24 mmol), 4-amino-nicotinic acid methyl ester (208 mg, 1.37 mmol), Pd(OAc)$_2$ (14 mg, 62.09 μmol) and Rac-BINAP (60 mg, 93.14 μmol) in dry dioxane (10 mL) was added Cs$_2$CO$_3$ (607 mg, 1.86 mmol). The mixture was heated for 12 h at 85° C., cooled and evaporated. The residue was purified by chromatography (CH$_2$Cl$_2$, 0-10% MeOH) to give the desired product (178 mg, 34% yield).

Preparation of 4-[2-(5-Chloro-2-fluoro-phenyl)-6,6-dimethyl-6,7-dihydro-5H-cyclopentapyrimidin-4-ylamino]-nicotinic acid To a solution of 4-[2-(5-Chloro-2-fluoro-phenyl)-6,6-dimethyl-6,7-dihydro-5H-cyclopentapyrimidin-4-ylamino]-nicotinic acid methyl ester (178 mg, 0.42 mmol) in dioxane (10 mL) was added NaOH (aq.) (451 μL, 0.44 mmol, 0.97N solution). The mixture was heated at 60° C. for 1 h, then cooled, and HCl (aq.) (425 μL, 0.44 mmol, 1.03N solution) was added. On addition, the acid precipitated from solution and was filtered and dried in vacuo, to give 137 mg of product.

Preparation of 4-[2-(5-Chloro-2-fluoro-phenyl)-6,6-dimethyl-6,7-dihydro-5H-cyclopentapyrimidin-4-ylamino]-nicotinamide A suspension of 4-[2-(5-Chloro-2-fluoro-phenyl)-6,6-dimethyl-6,7-dihydro-5H-cyclopentapyrimidin-4-ylamino]-nicotinic acid (25 mg, 60.56 μmol) and carbonyl-diimidazole (20 mg, 121.11 μmol) in dry DMF (3 mL) was heated at 70° C. for 1 h and then cooled to r.t. A stream of NH$_3$ gas was passed through the solution for 30 min., giving clean conversion to the amide product. Evaporation of the solution, followed by HPLC purification gave, after lyophilization, the pure amide of formula (62) as the TFA salt (20 mg).

Compounds of formula (63) to (66) were prepared using the same procedure.

Scheme Q (Synthesis of compounds of formula (76) and (77))

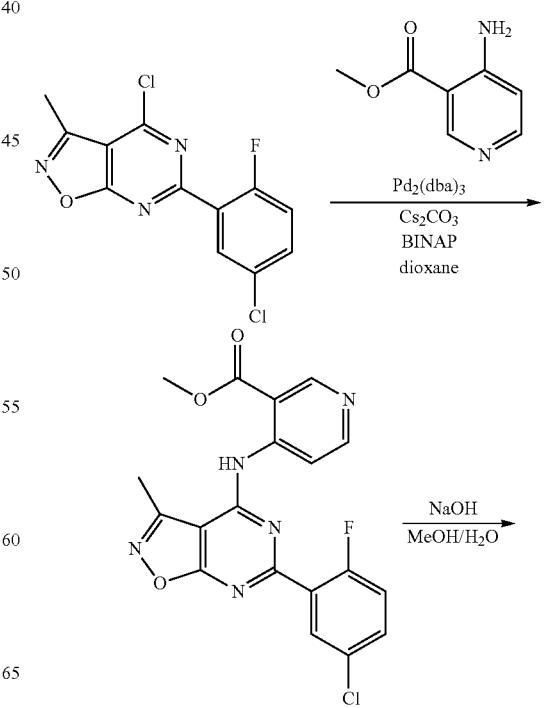

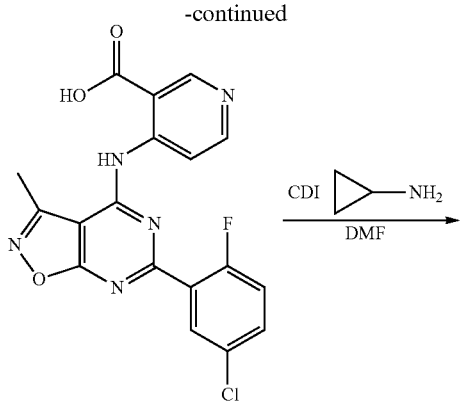

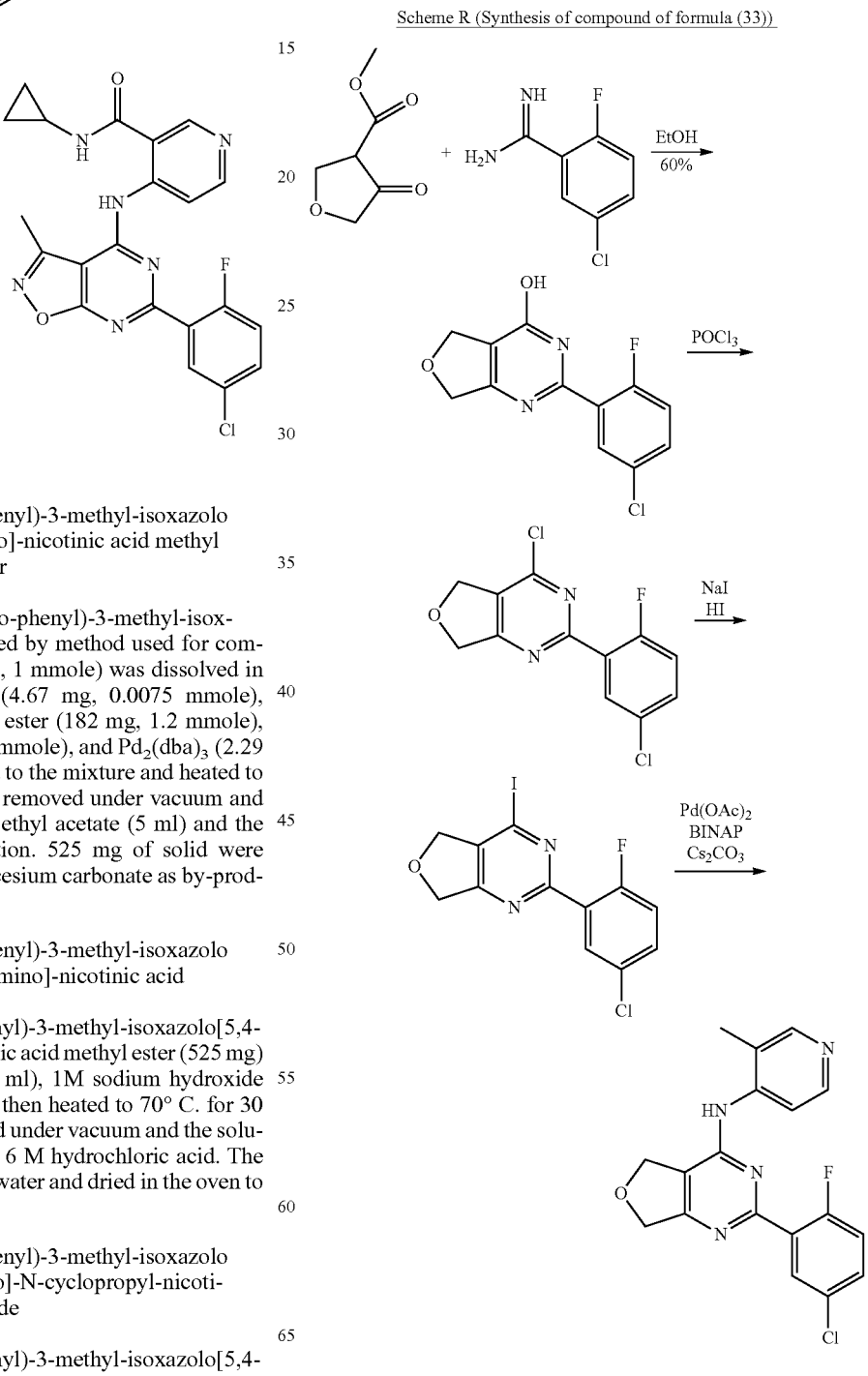

4-[6-(5-Chloro-2-fluoro-phenyl)-3-methyl-isoxazolo [5,4-d]pyrimidin-4-ylamino]-nicotinic acid methyl ester 4-Chloro-6-(5-chloro-2-fluoro-phenyl)-3-methyl-isoxazolo[5,4-d]pyrimidine (prepared by method used for compound of formula (43) (298 mg, 1 mmole) was dissolved in dioxane (4 ml), and BINAP (4.67 mg, 0.0075 mmole), 4-Amino-nicotinic acid methyl ester (182 mg, 1.2 mmole), cesium carbonate (456 mg, 1.4 mmole), and Pd$_2$(dba)$_3$ (2.29 mg, 0.0025 mmole) were added to the mixture and heated to 90° C. overnight. Dioxane was removed under vacuum and the residue was triturated with ethyl acetate (5 ml) and the product was isolated by filtration. 525 mg of solid were obtained which also contained cesium carbonate as by-product.

4-[6-(5-Chloro-2-fluoro-phenyl)-3-methyl-isoxazolo [5,4-d]pyrimidin-4-ylamino]-nicotinic acid 4-[6-(5-Chloro-2-fluoro-phenyl)-3-methyl-isoxazolo[5,4-d]pyrimidin-4-ylamino]-nicotinic acid methyl ester (525 mg) was suspended in methanol (4 ml), 1M sodium hydroxide solution (4 ml) was added, and then heated to 70° C. for 30 min. The methanol was removed under vacuum and the solution was acidified to pH 4 with 6 M hydrochloric acid. The solid was filtered, washed with water and dried in the oven to give 137 mg product.

4-[6-(5-Chloro-2-fluoro-phenyl)-3-methyl-isoxazolo [5,4-d]pyrimidin-4-ylamino]-N-cyclopropyl-nicotinamide 4-[6-(5-Chloro-2-fluoro-phenyl)-3-methyl-isoxazolo[5,4-d]pyrimidin-4-ylamino]-nicotinic acid (130 mg, 0.325 mmole) was combined with carbonyl diimidazole (105 mg, 0.650 mmole) in 2 ml dimethylformamide and heated to 70° C. for 1 hour. The mixture was cooled to room temperature, cyclopropylamine (74 mg, 1.3 mmole) was added and stirred for 1 hour at room temperature. The solution was filtered and the filtrate was subjected to HPLC purification on reversed phase HPLC. Upon lyophilization of the fractions containing pure product, 13.7 mg of pure product was obtained.

Compound of formula (77) was prepared using a procedure described above, using methylamine.

Scheme R (Synthesis of compound of formula (33))

2-(5-Chloro-2-fluorophenyl)-5,7-dihydrofuro[3,4-d]pyrimidin-4-ol

To a suspension of 4-oxo-tetrahydrofuran-3-carboxylic acid methyl ester (prepared according to Dowd, P.; Choi, S-C. *Tetrahedron*, 1991, 47, 4847-4860; 800 mg, 5.55 mmol, 1 eq) in ethanol (20 ml) was added a solution of 2-fluoro-5-chlorobenzamidine (961 mg, 5.55 mmol, 1 eq) in EtOH (10 ml). The reaction mixture was heated to 80° C. overnight. The reaction mixture was cooled to r.t. and the white precipitate was filtered and washed with cold ethyl actetate (2×20 ml). The crude residue was partitioned between chloroform and water. The aqueous layer was acidified to pH 4 and the product was extracted with chloroform (3×50 ml). The organic layers were combined, washed with brine, dried over MgSO$_4$, filtered and concentrated in vacuo to give a crude solid which was purified by flash column chromatography (5% MeOH in EtOAc) to give a white solid 2-(5-chloro-2-fluoro-phenyl)-5,7-dihydrofuro[3,4-d]pyrimidin-4-ol (440 mg, 30%).

4-Chloro-2-(5-chloro-2-fluorophenyl)-5,7-dihydrofuro[3,4-d]pyrimidine

A suspension of 2-(5-chloro-2-fluorophenyl)-5,7-dihydrofuro[3,4-d]pyrimidin-4-ol (100 mg, 0.36 mmol, 1 eq) in POCl$_3$ (5 ml) was stirred under reflux for 1 h. The solution was then cooled to room temperature and concentrated under reduced pressure to give a white solid which was dissolved in dry methylene chloride. The solution was cooled to 0° C. and ice was added followed by sat. NaHCO$_3$. The organic layer was separated, washed with brine, dried (MgSO$_4$), filtered and evaporated in vacuo to provide a crude white solid which was purified by flash column chromatography (1:9 EtOAc:Hexane) to give 4-Chloro-2-(5-chloro-2-fluorophenyl)-5,7-dihydrofuro[3,4-d]-pyrimidine (78 mg, 73%) as a white solid.

2-(5-Chloro-2-fluorophenyl)-4-iodo-5,7-dihydrofuro[3,4-d]pyrimidine

To a suspension of 4-chloro-2-(5-chloro-2-fluorophenyl)-5,7-dihydrofuro[3,4-d]-pyrimidine (78 mg, 0.275 mmol, 1 eq) in 57% HI$_{(aq)}$ (2 ml) at r.t. was added NaI (206 mg, 1.37 mmol, 5 eq). The reaction mixture was stirred at r.t. overnight and then was poured onto ice. The product was extracted with chloroform and the aqueous layer was neutralized with NaHCO$_3$ and extracted further with chloroform. The organic layers were combined washed with brine, dried (MgSO$_4$), filtered and evaporated in vacuo to provide a crude residue of 2-(5-Chloro-2-fluorophenyl)-4-iodo-5,7-dihydro-furo[3,4-d]pyrimidine which was not further purified.

[2-(5-Chloro-2-fluorophenyl)-5,7-dihydrofuro[3,4-d]pyrimidin-4-yl]-(3-methyl-pyridin-4-yl)-amine, compound of formula (33)

To a solution of 2-(5-chloro-2-fluorophenyl)-4-iodo-5,7-dihydrofuro[3,4-d]pyrimidine (80 mg, 0.21 mmol, 1 eq) in anhydrous dioxane (5 ml) was added Pd(OAc)$_2$ (2 mg, 0.01 mmol, 0.05 eq) followed by BINAP (10 mg, 0.02 mmol, 0.075 eq), 4-amino-3-picoline (25 mg, 0.23 mmol, 1.2 eq) and Cs$_2$CO$_3$ (100 mg, 0.32 mmol, 1.5 eq). The reaction mixture was heated to 80° C. for 15 h. The reaction mixture was cooled to r.t. and filtered through Celite® and the crude material was purified by flash column chromatography (9:1/ethyl acetate:hexane) to afford [2-(5-Chloro-2-fluorophenyl)-5,7-dihydrofuro[3,4-d]pyrimidin-4-yl]-(3-methyl-pyridin-4-yl)-amine, compound of formula (33) (20 mg, 26%) as a white solid.

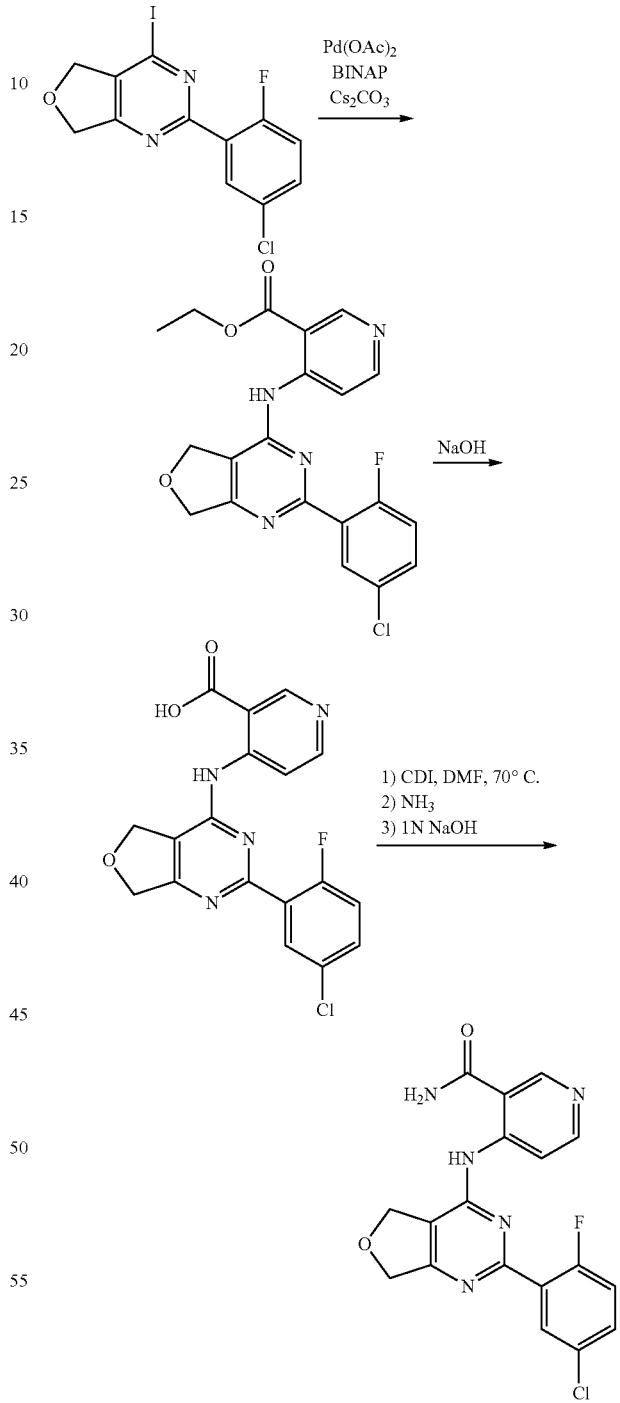

Scheme S (Synthesis of compound of formula (34))

4-[2-(5-Chloro-2-fluoro-phenyl)-5,7-dihydro-furo[3,4-d]pyrimidin-4-ylamino]-nicotinic acid ethyl ester Following the general reaction procedure used for the synthesis of [2-(5-Chloro-2-fluorophenyl)-5,7-dihydrofuro[3,4- d]pyrimidin-4-yl]-(3-methyl-pyridin-4-yl)-amine, i.e. compound of formula (33), 4-[2-(5-chloro-2-fluoro-phenyl)-5,7-dihydro-furo[3,4-d]pyrimidin-4-ylamino]-nicotinic acid ethyl ester was isolated in 73% yield.

4-[2-(5-Chloro-2-fluoro-phenyl)-5,7-dihydro-furo[3,4-d]pyrimidin-4-ylamino]-nicotinic acid To a suspension of 4-[2-(5-chloro-2-fluoro-phenyl)-5,7-dihydro-furo[3,4-d]pyrimidin-4-ylamino]-nicotinic acid ethyl ester (60 mg, 0.14 mmol, 1 eq) in MeOH (5 ml) was added a 1 N NaOH$_{(aq)}$ solution (300 µl, 0.30 mmol, 2 eq) and the reaction mixture was heated to reflux for 2 h. The solution was cooled to r.t. and concentrated in vacuo. Water (20 ml) was added to the crude material and the aqueous layer was acidified to pH 4. The solid was filtered, washed with water (2×5 ml) and dried overnight to afford 4-[2-(5-Chloro-2-fluoro-phenyl)-5,7-dihydro-furo[3,4-d]pyrimidin-4-ylamino]-nicotinic acid (50 mg, 90%).

4-[2-(5-Chloro-2-fluoro-phenyl)-5,7-dihydro-furo[3,4-d]pyrimidin-4-ylamino]-nicotinic amide compound of formula (34)

To a suspension of 4-[2-(5-chloro-2-fluoro-phenyl)-5,7-dihydro-furo[3,4-d]pyrimidin-4-ylamino]-nicotinic acid (50 mg, 0.13 mmol, 1 eq) in DMF (2 ml) was added 1-1'-carbonyldiimidazole (50 mg, 0.31 mmol, 2.4 eq) and the reaction mixture was warmed to 70° C. for 2 h. The mixture was cooled to r.t. and NH$_{3(g)}$ was bubbled through for 10 min. The reaction mixture was stirred at r.t. for an additional 1 h. The reaction was concentrated in vacuo and the residue was triturated with water (2×5 ml). To the crude residue was added 1 N NaOH (5 ml) and the suspension was heated to 100° C. for 2 h. The reaction mixture was cooled to room temperature and neutralized with 1 N HCl and the solid was filtered to give 4-[2-(5-Chloro-2-fluoro-phenyl)-5,7-dihydro-furo[3,4-d]pyrimidin-4-ylamino]-nicotinic amide, compound of formula (34) (25 mg, 50%) as a white solid.

Scheme T (Synthesis of compound of formula (38))

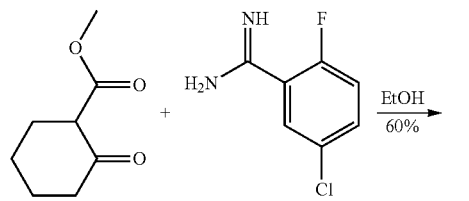

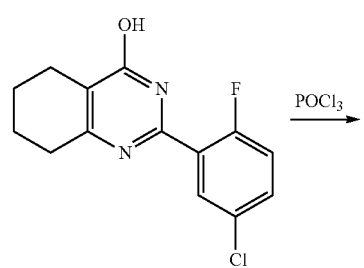

-continued

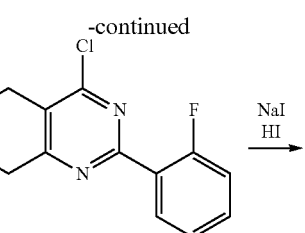

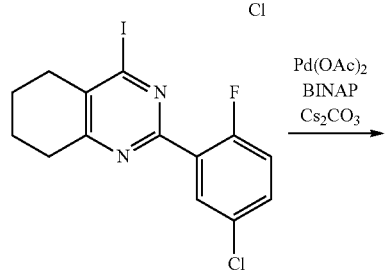

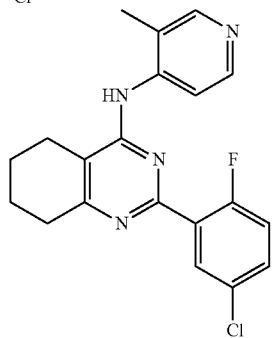

2-(5-Chloro-2-fluorophenyl)-5,6,7,8-tetrahydroquinazolin-4-ol

To a solution of methyl-2-oxocyclopentane carboxylate (2 g, 11.8 mmol, 1 eq), in dry ethanol (20 ml) was added a solution of 2-fluoro-5-chlorobenzamidine (2.04 g, 11.8 mmol, 1 eq) in ethanol (20 ml) and the reaction mixture was heated to 80° C. overnight. The reaction mixture was cooled to r.t. and the solvent was removed in vacuo to afford a crude residue which was purified by recrystallization from hot ethyl acetate to afford 2-(5-chloro-2-fluorophenyl)-5,6,7,8-tetrahydroquinazolin-4-ol (2.56 g, 78%) as a white solid.

4-Chloro-2-(5-chloro-2-fluorophenyl)-5,6,7,8-tetrahydroquinazoline

A suspension of 2-(5-chloro-2-fluorophenyl)-5,6,7,8-tetrahydroquinazolin-4-ol (500 mg, 1.89 mmol) in POCl$_3$ (6 ml) was stirred under reflux for 1 h. The solution was then cooled to room temperature and concentrated under reduced pressure to afford a white solid which was dissolved in methylene chloride. The solution was cooled to 0° C. and ice was added followed by sat. NaHCO$_3$. The organic layer was separated, washed with brine, dried (MgSO$_4$), filtered and evaporated in vacuo to provide a crude white solid 4-Chloro-2-(5-chloro-2-fluorophenyl)-5,6,7,8-tetrahydroquinazoline which was not further purified.

2-(5-Chloro-2-fluorophenyl)-4-iodo-5,6,7,8-tetrahydroquinazoline

To a suspension of 4-chloro-2-(5-chloro-2-fluorophenyl)-5,6,7,8-tetrahydroquinazoline (534 mg, 1.89 mmol, 1 eq) in a 57% HI solution in water (10 ml) at r.t. was added NaI (1.42 g, 9.47 mmol, 5 eq). The reaction mixture was stirred at r.t. overnight and then poured onto ice. The product was extracted with chloroform and the aqueous layer was neutralized with NaHCO₃ and extracted further with more chloroform. The organic layers were combined, washed with brine, dried (MgSO₄), filtered and evaporated in vacuo to provide a crude white solid 2-(5-Chloro-2-fluorophenyl)-4-iodo-5,6,7,8-tetrahydroquinazoline which was not further purified.

[2-(5-Chloro-2-fluorophenyl)-5,6,7,8-tetrahydroquinazolin-4-yl]-(3-methylpyridin-4-yl)-amine, Compound of Formula (38)

The crude 2-(5-chloro-2-fluorophenyl)-4-iodo-5,6,7,8-tetrahydroquinazoline (130 mg, 0.35 mmol, 1 eq) was dissolved in dioxane (5 ml) and to this was added Pd(OAc)₂ (4 mg, 0.02 mmol, 0.05 eq) followed by BINAP (16 mg, 0.03 mmol, 0.075 eq), 4-amino-3-picoline (49 mg, 0.45 mmol, 1.3 eq) and Cs₂CO₃ (170 mg, 0.52 mmol, 1.5 eq). The reaction mixture was heated to 80° C. for 15 h. The reaction mixture was cooled to r.t. and filtered through Celite® and the crude material was purified by flash column chromatography (1:1/ethyl acetate:hexane) to afford [2-(5-chloro-2-fluoro-phenyl)-5,6,7,8-tetrahydroquinazolin-4-yl]-(3-methylpyridin-4-yl)-amine, compound of formula (38) (110 mg, 86%).

Scheme U (Synthesis of compounds of formula (50), (40), (45), (57), (59))

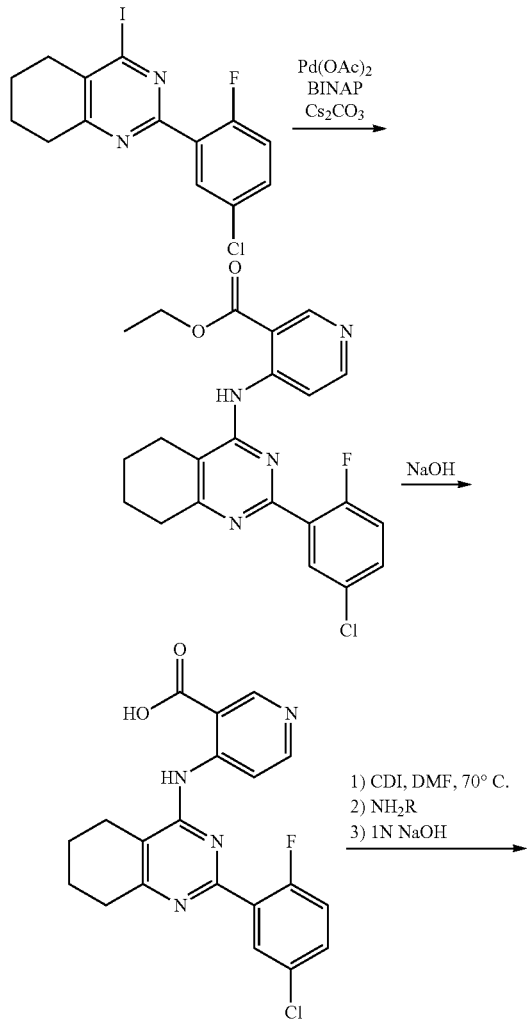

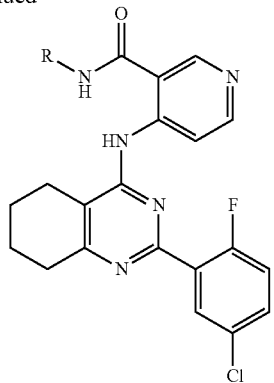

4-[2-(5-Chloro-2-fluorophenyl)-5,6,7,8-tetrahydroquinazolin-4-ylamino]-nicotinic acid ethyl ester Following the general reaction procedure for the synthesis of [2-(5-chloro-2-fluorophenyl)-5,6,7,8-tetrahydroquinazolin-4-yl]-(3-methylpyridin-4-yl)-amine, i.e. compound of formula (38), 4-[2-(5-Chloro-2-fluorophenyl)-5,6,7,8-tetrahydroquinazolin-4-ylamino]-nicotinic acid ethyl ester was isolated in 67% yield.

4-[2-(5-Chloro-2-fluorophenyl)-5,6,7,8-tetrahydroquinazolin-4-ylamino]-nicotinic acid 50

To a suspension of 4-[2-(5-chloro-2-fluorophenyl)-5,6,7,8-tetrahydroquinazolin-4-yl-amino]-nicotinic acid ethyl ester (150 mg, 0.35 mmol, 1 eq) in MeOH (5 ml) was added a 1N NaOH$_{(aq)}$ solution (423 µl, 0.42 mmol, 1.2 eq) and the reaction mixture was refluxed for 1 h. The solution was cooled to r.t. and concentrated in vacuo. Water (20 ml) was added to the crude material and the aqueous layer was acidified to pH 4. The solid was filtered, washed with water (2×5 ml) and dried overnight to give 4-[2-(5-chloro-2-fluorophenyl)-5,6,7,8-tetrahydroquinazolin-4-ylamino]-nicotinic acid, compound of formula (50) (132 mg, as a cream colored solid.

4-[2-(5-Chloro-2-fluorophenyl)-5,6,7,8-tetrahydroquinazolin-4-ylamino]-N-cyclopropyl nicotinamide, compound of formula (45)

To a suspension of 4-[2-(5-chloro-2-fluorophenyl)-5,6,7,8-tetrahydroquinazolin-4-yl-amino]-nicotinic acid (40 mg, 0.10 mmol, 1 eq) in dry DMF (1 ml) was added triethylamine (15 µl, 0.11 mmol, 1.1 eq) followed by cyclopropylamine (70 µl, 0.10 mmol, 10 eq). To the suspension was added a solution of PyBrOP (56 mg, 0.21 mmol, 1.2 eq) in DMF (500 µl) dropwise. The reaction mixture was stirred at room temperature for 16 h. The reaction was concentrated in vacuo and the residue was triturated with ether (2×20 ml). The crude residue was purified by flash column chromatography (0-5% MeOH in CHCl₃) to give 4-[2-(5-Chloro-2-fluorophenyl)-5,6,7,8-tetrahydroquinazolin-4-ylamino]-N-cyclopropyl nicotinamide, compound of formula (45), (15 mg, 34%) as a white solid.

Compound of formula (40) was prepared by the method described for the synthesis of compound of formula (45) employing methylamine in place of cyclopropylamine. Compound of formula (57) was prepared by the method described for the synthesis of compound of formula (45) employing 1-amino-propan-2-(S)-ol in place of cyclopropylamine. Compound of formula (59) was prepared by the method described for the synthesis of compound of formula (45) employing N,N-diethylethanediamine in place of cyclopropylamine

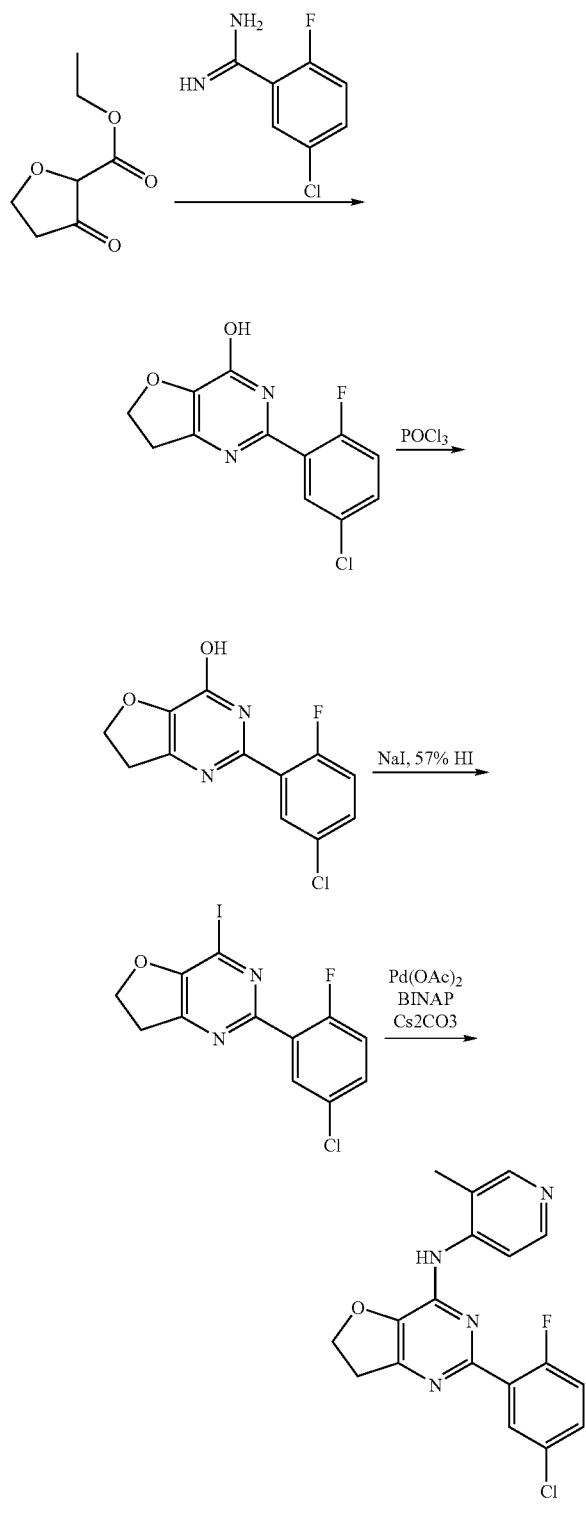

2-(5-Chloro-2-fluorophenyl)-6,7-dihydrofuro[3,2-d]pyrimidin-4-ol

To a solution of 2-fluoro-5-chlorobenzamidine (1.05 g, 6.08 mmol, 1.2 eq) in EtOH (20 ml) was added 3-oxo-tetrahydrofuran-2-carboxylic acid ethyl ester (prepared according to Moyer, M. P; Feldman, P. L.; Rapoport, H. *J. Org. Chem*, 1985, 50, 5223-5230; 800 mg, 5.06 mmol, 1 eq) in ethanol (5 ml). The reaction mixture was heated to 80° C. overnight. The reaction mixture was cooled to r.t. and the crude residue was purified by flash column chromatography (5% MeOH in $CHCl_3$) to afford a white solid 2-(5-chloro-2-fluorophenyl)-6,7-dihydrofuro[3,2-d]pyrimidin-4-ol (650 mg, 53%).

4-Chloro-2-(5-chloro-2-fluorophenyl)-6,7-dihydrofuro[3,2-d]pyrimidine

A suspension of 2-(5-chloro-2-fluorophenyl)-6,7-dihydrofuro[3,2-d]pyrimidin-4-ol (100 mg, 0.36 mmol, 1 eq) in $POCl_3$ (5 ml) was stirred under reflux for 1 h. The solution cooled to r.t. and concentrated under reduced pressure to give a white solid which was dissolved in methylene chloride. The solution was cooled to 0° C. and ice was added followed by sat. $NaHCO_3$. The organic layer was separated, washed with brine, dried ($MgSO_4$), filtered and evaporated in vacuo to provide a crude white solid which was purified by flash column chromatography (1:9 EtOAc:Hexane) to afford 4-chloro-2-(5-chloro-2-fluorophenyl)-6,7-dihydrofuro[3,2-d]pyrimidine (78 mg, 73%) as a white solid.

2-(5-Chloro-2-fluorophenyl)-4-iodo-6,7-dihydrofuro[3,2-d]pyrimidine

To a suspension of 4-chloro-2-(5-chloro-2-fluorophenyl)-6,7-dihydrofuro[3,2-d]-pyrimidine (80 mg, 0.28 mmol, 1 eq) in a 57% HI solution in water (2 ml) at rt. was added NaI (206 mg, 1.41 mmol, 5 eq). The reaction mixture was stirred at r.t. overnight and then poured onto ice. The product was extracted with chloroform and the aqueous layer was neutralized with $NaHCO_3$ and extracted further with more chloroform. The organic layers were combined washed with brine, dried ($MgSO_4$), filtered and evaporated in vacuo to provide a crude residue 2-(5-chloro-2-fluorophenyl)-4-iodo-6,7-dihydrofuro[3,2-d]pyrimidine that was not further purified.

[2-(5-Chloro-2-fluorophenyl)-6,7-dihydrofuro[3,2-d]pyrimidin-4-yl]-(3-methyl-pyridin-4-yl)-amine, compound of formula (39)

To a solution of 2-(5-chloro-2-fluorophenyl)-4-iodo-6,7-dihydrofuro[3,2-d]pyrimidine (106 mg, 0.28 mmol, 1 eq) in dioxane (5 ml) was added $Pd(OAc)_2$ (3 mg, 0.01 mmol, 0.05 eq) followed by BINAP (13 mg, 0.02 mmol, 0.075 eq), 4-amino-3-picoline (40 mg, 0.37 mmol, 1.3 eq) and $Cs_2CO_3$ (138 mg, 0.42 mmol, 1.5 eq). The reaction mixture was heated to 80° C. for 15 h. The reaction mixture was cooled to r.t. and filtered through Celite® and the crude material was purified by flash column chromatography (4:1/ethyl acetate:hexane-100% ethylacetate) to afford [2-(5-chloro-2-fluorophenyl)-6,7-dihydrofuro[3,2-d]pyrimidin-4-yl]-(3-methyl-pyridin-4-yl)-amine, i.e. compound of formula (39) (30 mg, 30%) as a white solid.

Scheme W (Synthesis of compound of formula (44))

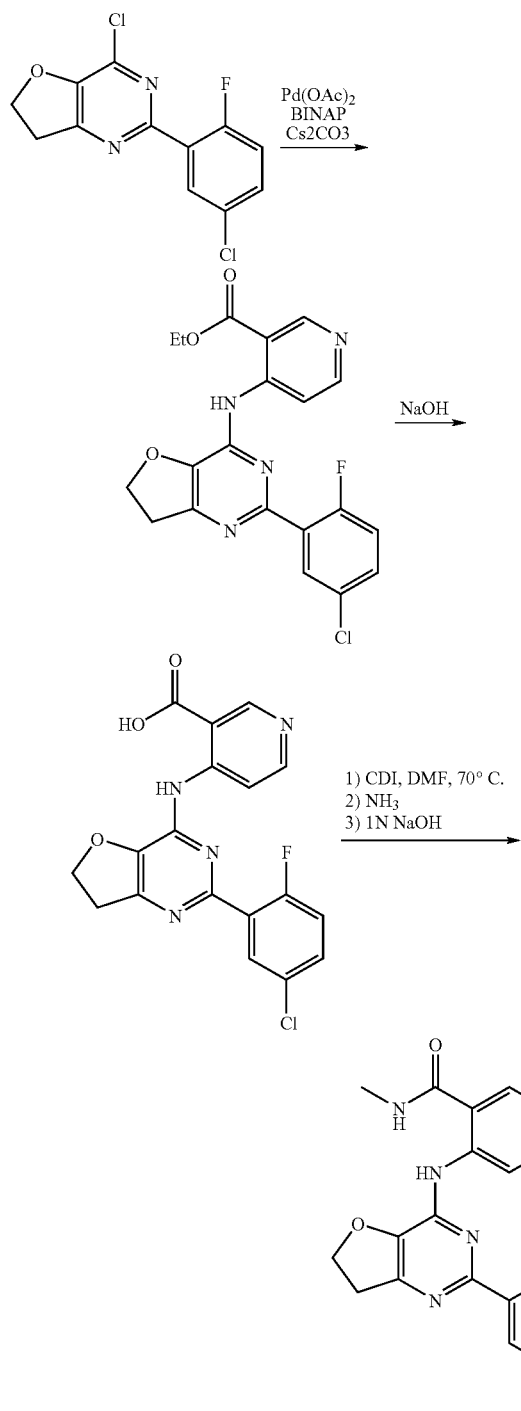

4-[2-(5-Chloro-2-fluorophenyl)-6,7-dihydrofuro[3,2-d]pyrimidin-4-ylamino]-nicotinic acid ethyl ester To a solution of 4-chloro-2-(5-chloro-2-fluorophenyl)-6,7-dihydrofuro[3,2-d]-pyrimidine (320 mg, 1.13 mmol, 1 eq) in dioxane (5 ml) was added Pd(OAc)$_2$ (13 mg, 0.06 mmol, 0.05 eq) followed by BINAP (53 mg, 0.08 mmol, 0.075 eq), 4-amino-nicotinic acid ethyl ester (206 mg, 1.24 mmol, 1.1 eq) and Cs$_2$CO$_3$ (478 mg, 1.46 mmol, 1.5 eq). The reaction mixture was heated to 80° C. for 15 h. The reaction mixture was cooled to r.t. and filtered through Celite® and the crude material was purified by flash column chromatography (0-5% MeOH in CHCl$_3$) to afford 4-[2-(5-chloro-2-fluorophenyl)-6,7-dihydrofuro[3,2-d]pyrimidin-4-ylamino]-nicotinic acid ethyl ester (100 mg, 21%) as a white solid.

4-[2-(5-Chloro-2-fluorophenyl)-6,7-dihydrofuro[3,2-d]pyrimidin-4-ylamino]-nicotinic acid To a suspension of 4-[2-(5-chloro-2-fluorophenyl)-6,7-dihydrofuro[3,2-d]pyrimidin-4-ylamino]-nicotinic acid ethyl ester (100 mg, 0.24 mmol, 1 eq) in MeOH (5 ml) was added a 1 N NaOH$_{(aq)}$ solution (290 µl, 0.29 mmol, 1.2 eq) and the reaction mixture was refluxed for 5 h. The solution was cooled to r.t. and concentrated in vacuo. Water (20 ml) was added to the crude material and the aqueous layer was acidified to pH 4. The solid was filtered, washed with water (2×5 ml) and dried overnight to afford 4-[2-(5-chloro-2-fluorophenyl)-6,7-dihydrofuro[3,2-d]pyrimidin-4-ylamino]-nicotinic acid (88 mg, 94%) as a cream colored solid.

4-[2-(5-Chloro-2-fluorophenyl)-6,7-dihydrofuro[3,2-d]pyrimidin-4-ylamino]-N-methyl nicotinamide, Compound of Formula (44)

To a suspension of 4-[2-(5-chloro-2-fluorophenyl)-6,7-dihydrofuro[3,2-d]pyrimidin-4-ylamino]-nicotinic acid (75 mg, 0.19 mmol, 1 eq) in DMF (2 ml) was added triethylamine (30 µl, 0.21 mmol, 1.1 eq) followed by methylamine (1.17 ml, 3.89 mmol, 2 M solution in THF, 20 eq). To the suspension was added a solution of PyBrOP (100 mg, 0.21 mmol, 1.2 eq) in DMF (1 ml) dropwise. The reaction mixture was stirred at room temperature for 16 h. The reaction was concentrated in vacuo and the residue was triturated with ether (2×20 ml). The crude residue was purified by flash column chromatography (5% MeOH in CHCl$_3$) to afford 4-[2-(5-chloro-2-fluorophenyl)-6,7-dihydrofuro[3,2-d]pyrimidin-4-ylamino]-N-methyl nicotinamide, i.e. compound of formula (44) (20 mg, 26%) as a white solid.

Scheme X (Synthesis of compound of formula (43))

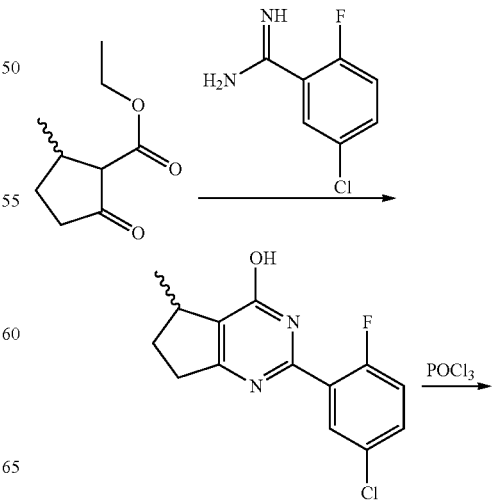

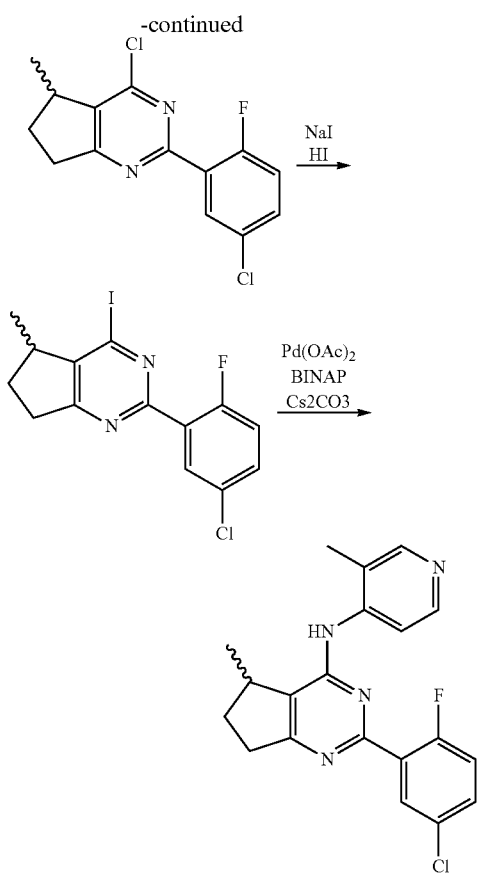

2-(5-Chloro-2-fluorophenyl)-5-methyl-6,7-dihydro-
5H-cyclopentapyrimidin-4-ol

To a solution of 2-fluoro-5-chlorobenzamidine (1.95 g, 11.27 mmol, 1.1 eq) in EtOH (20 ml) was added a solution of 2-methyl-5-oxo cyclopentanecarboxylic acid ethyl ester (prepared according to Wang, C.; Gu, X.; Yu, M. S.; Curran, D. P.: *Tetrahedron*, 1998, 29, 8355-8370; 1.60 g, 10.26 mmol, 1 eq) in ethanol (5 ml). The reaction mixture was heated to 80° C. overnight. The reaction mixture was cooled to r.t. and the solvent was removed in vacuo to give a crude residue which was purified by recrystallization from hot ethyl acetate to give 2-(5-chloro-2-fluorophenyl)-5-methyl-6,7-dihydro-5H-cyclopentapyrimidin-4-ol (1.0 g, 35%) as a white crystalline solid and the filtrate was further purified by flash column chromatography to give another 850 mg of 2-(5-chloro-2-fluorophenyl)-5-methyl-6,7-dihydro-5H-cyclopentapyrimidin-4-ol.

2-(5-Chloro-2-fluorophenyl)-4-iodo-5-methyl-6,7-dihydro-5H-cyclopentapyrimidine

A suspension of 2-(5-chloro-2-fluorophenyl)-5-methyl-6,7-dihydro-5H-cyclopentapyrimidin-4-ol (200 mg, 0.72 mmol, 1 eq) in $POCl_3$ (5 ml) was stirred under reflux for 1 h. The solution was then cooled to room temperature and concentrated under reduced pressure to give a white solid. The residual $POCl_3$ was removed by azeotrope with chloroform. To a suspension of the crude iminochloride in a 57% HI solution in water (5 ml) at r.t. was added NaI (540 mg, 3.60 mmol, 5 eq). The reaction mixture was stirred at r.t. overnight and then poured onto ice. The product was extracted with chloroform and the aqueous layer was neutralized with $NaHCO_3$ and extracted further with chloroform. The organic layers were combined washed with brine, dried ($MgSO_4$), filtered and evaporated in vacuo to provide a crude residue 2-(5-chloro-2-fluorophenyl)-4-iodo-5-methyl-6,7-dihydro-5H-cyclopentapyrimidine which was not further purified.

[2-(5-Chloro-2-fluorophenyl)-5-methyl-6,7-dihydro-5H-cyclopentapyrimidin-4-yl]-(3-methyl-pyridin-4-yl)-amine, compound of formula (43)

To a solution of 2-(5-chloro-2-fluorophenyl)-4-iodo-5-methyl-6,7-dihydro-5H-cyclopentapyrimidine (275 mg, 0.71 mmol, 1 eq) in dioxane (5 ml) was added $Pd(OAc)_2$ (8 mg, 0.04 mmol, 0.05 eq) followed by BINAP (33 mg, 0.05 mmol, 0.075 eq), 4-amino-3-picoline (84 mg, 0.78 mmol, 1.1 eq) and $Cs_2CO_3$ (347 mg, 1.06 mmol, 1.5 eq). The reaction mixture was heated to 80° C. for 15 h. The reaction mixture was cooled to r.t. and filtered through Celite® and the crude material was purified by flash column chromatography (1:1/ethyl acetate:hexane-100% ethyl acetate) to afford [2-(5-chloro-2-fluorophenyl)-5-methyl-6,7-dihydro-5H-cyclopentapyrimidin-4-yl]-(3-methyl-pyridin-4-yl)-amine, compound of formula (43) (250 mg, 96%).

Scheme Y (Synthesis of compounds of formula (48), (49), (47), (46))

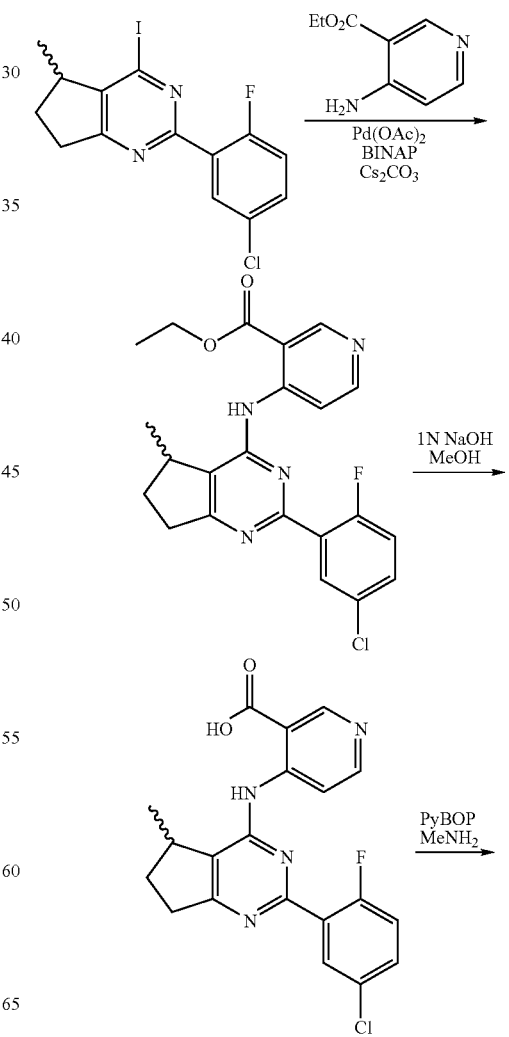

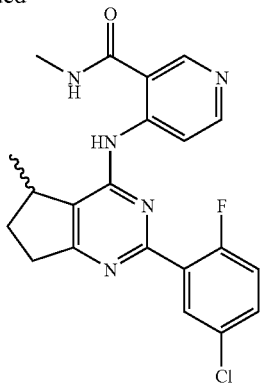

4-[2-(5-Chloro-2-fluoro-phenyl)-5-methyl-6,7-dihydro-5H-cyclopentapyrimidin-4-ylamino]-nicotinic acid ethyl ester, Compound of Formula (48)

Following the general reaction procedure for the synthesis of [2-(5-chloro-2-fluorophenyl)-5-methyl-6,7-dihydro-5H-cyclopentapyrimidin-4-yl]-(3-methyl-pyridin-4-yl)-amine, i.e. compound of formula (43), 4-[2-(5-chloro-2-fluoro-phenyl)-5-methyl-6,7-dihydro-5H-cyclopentapyrimidin-4-ylamino]-nicotinic acid ethyl ester, compound of formula (48), was isolated in 68% yield.

4-[2-(5-Chloro-2-fluoro-phenyl)-5-methyl-6,7-dihydro-5H-cyclopentapyrimidin-4-ylamino]-nicotinic acid, Compound of Formula (49)

To a suspension of 4-[2-(5-chloro-2-fluoro-phenyl)-5-methyl-6,7-dihydro-5H-cyclopentapyrimidin-4-ylamino]-nicotinic acid ethyl ester (180 mg, 0.42 mmol, 1 eq) in MeOH (5 ml) was added a 1 N NaOH$_{(aq)}$ solution (634 μl, 0.63 mmol, 1.5 eq) and the reaction mixture was heated to reflux for 1 h. The solution was cooled to r.t. and concentrated in vacuo. Water (20 ml) was added to the crude material and the aqueous layer was acidified to pH 4. The solid was filtered, washed with water (2×5 ml) and dried overnight to give 4-[2-(5-chloro-2-fluorophenyl)-5-methyl-6,7-dihydro-5H-cyclopentapyrimidin-4-ylamino]-nicotinic acid, compound of formula (49) (160 mg, 95%) as a white solid.

4-[2-(5-Chloro-2-fluoro-phenyl)-5-methyl-6,7-dihydro-5H-cyclopentapyrimidin-4-ylamino]-N-methyl-nicotinamide, Compound of Formula (47)

To a suspension of 4-[2-(5-chloro-2-fluorophenyl)-5-methyl-6,7-dihydro-5H-cyclopentapyrimidin-4-ylamino]-nicotinic acid (20 mg, 0.05 mmol, 1 eq) in DMF (2 ml) was added triethylamine (8 μl, 0.05 mmol, 1.1 eq) followed by methylamine (250 μl, 3.89 mmol, 2 M solution in THF, 10 eq). To the suspension was added a solution of PyBOP (40 mg, 0.08 mmol, 1.5 eq) in DMF (1 ml) dropwise. The reaction mixture was stirred at room temperature for 16 h. The reaction was concentrated in vacuo and the residue was triturated with ether (2×20 ml). The crude residue was purified by flash column chromatography (100% ethylacetate) to afford 4-[2-(5-chloro-2-fluorophenyl)-5-methyl-6,7-dihydro-5H-cyclopentapyrimidin-4-ylamino]-N-methyl-nicotinamide, i.e. compound of formula (47), (12 mg, 58%) as a white solid. Compound of formula (46) was prepared by the method described for the synthesis of compound of formula (47) employing ammonia in place of methylamine.

Compounds of formula (1) may be converted into each other following art-known functional group transformation reactions, comprising those described hereinafter. A number of the intermediates used to prepare the compounds of formula (1) are known compounds or are analogs of known compounds, which can be prepared following modifications of art-known methodologies readily accessible to the skilled person.

The compounds of formula (1) may be converted to the corresponding N-oxide forms following art-known procedures for converting a trivalent nitrogen into its N-oxide form. Said N-oxidation reaction may generally be carried out by reacting the starting material of formula (1) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (1) may be obtained by the application of art-known procedures. Diastereomers may be separated by physical methods such as selective crystallization and chromatographic techniques, e.g., counter-current distribution, liquid chromatography and the like.

The compounds of formula (1) may be obtained as racemic mixtures of enantiomers which can be separated from one another following art-known resolution procedures. The racemic compounds of formula (1), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (1) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

The manner of administration and formulation of the compounds useful in the invention and their related compounds will depend on the nature of the condition, the severity of the condition, the particular subject to be treated, and the judgment of the practitioner; formulation will depend on mode of administration. The compounds of the present invention or any subgroup thereof may be formulated into various pharmaceutical forms for administration purposes. As appropriate compositions there may be cited all compositions usually employed for systemically administering drugs.

To prepare the pharmaceutical compositions of this invention, a therapeutically effective amount of the particular compound, optionally in addition salt form or metal complex, as the active ingredient is combined in intimate admixture with a pharmaceutically acceptable carrier, which carrier may take a wide variety of forms depending on the form of preparation desired for administration. A therapeutically effective amount in this context is an amount sufficient to prophylactically act against, to stabilize or to reduce viral infection, and in particular HCV viral infection, or to prevent disease progression towards chronic hepatitis, liver fibrosis, cirrhosis, end-stage liver disease, HCC (hepatocellular carcinoma) and the like, in infected subjects or subjects being at risk of being infected.

The pharmaceutical compositions are desirable in unitary dosage form suitable, particularly, for administration orally, rectally, percutaneously, or by parenteral injection. In preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (1) and a pharmaceutically acceptable carrier. Preferably, the compounds of the present invention are administered via inhalation of a solution in nebulized or aerosolized doses.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The dosages of the compounds of the invention will depend on a number of factors which will vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will vary, however, depending on the conditions being treated and the judgment of the practitioner.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Due to their favorable antiviral properties, as will be apparent from the examples, the compounds of the present invention are useful in the treatment of individuals infected by HCV and for the prophylaxis of these individuals. In general, the compounds of the present invention may be useful in the treatment of warm-blooded animals infected with flaviviruses. Conditions which may be prevented or treated with the compounds of the present invention, especially conditions associated with HCV and other pathogenic flaviviruses, such as Yellow fever, Dengue fever (types 1-4), St. Louis encephalitis, Japanese encephalitis, Murray valley encephalitis, West Nile virus and Kunjin virus. The conditions associated with HCV include progressive liver fibrosis, inflammation and necrosis leading to cirrhosis, end-stage liver disease, and HCC; and for the other pathogenic flaviruses the conditions include yellow fever, dengue fever, haemorraghic fever and encephalitis.

The compounds of the present invention or any subgroup thereof may therefore be used as medicines against the above-mentioned conditions. Said use as a medicine or method of treatment comprises the systemic administration to HCV-infected subjects of an amount effective to combat the conditions associated with HCV and other pathogenic flaviviruses. Consequently, the compounds of the present invention can be used in the manufacture of a medicament useful for treating conditions associated with HCV and other pathogenic flaviviruses.

In an embodiment, the invention relates to the use of a compound of formula (1) or any subgroup thereof as defined herein in the manufacture of a medicament for treating or combating infection or disease associated with HCV infection in a mammal. The invention also relates to a method of treating a flaviviral infection, or a disease associated with flavivirus infection comprising administering to a mammal in need thereof an effective amount of a compound of formula (1) or a subgroup thereof as defined herein.

In another embodiment, the present invention relates to the use of formula (1) or any subgroup thereof as defined herein for the manufacture of a medicament useful for inhibiting HCV activity in a mammal infected with flaviviruses, in particular HCV.

In another embodiment, the present invention relates to the use of formula (1) or any subgroup thereof as defined herein for the manufacture of a medicament useful for inhibiting HCV activity in a mammal infected with flaviviruses, wherein said HCV is inhibited in its replication.

It should be noted that the compounds of formula (1) can be administered as individual active ingredients, or as mixtures of several embodiments of this formula. The compounds of the invention may be used as single therapeutic agents or in combination with other therapeutic agents.

As such, the combination of previously known anti-HCV compound, such as, for instance, interferon-α (IFN-α), pegylated interferon-α and/or ribavirin, and a compound of the present invention can be used as a medicine in a combination therapy. The term "combination therapy" relates to a product containing mandatory (a) a compound of the present invention, and (b) optionally another anti-HCV compound, as a combined preparation for simultaneous, separate or sequential use in treatment of HCV infections, in particular, in the treatment of infections with HCV type 1. Thus, to combat or treat HCV infections, the compounds of this invention may be co-administered in combination with for instance, interferon-α (IFN-α), pegylated interferon-α and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (1) or any subgroup thereof as defined above for the manufacture of a medicament useful for inhibiting HCV activity in a mammal infected with HCV viruses, wherein said medicament is used in a combination therapy, said combination therapy preferably comprising a compound of formula (1) and (pegylated) IFN-α and/or ribavirin, and possibly an anti-HIV compound.

It will be appreciated by the person skilled in the art that the compounds of formula (1) may be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter-screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counterscreen to eliminate non-selective inhibitors.

All patents, patent applications and articles referred to before or below are incorporated herein by reference.

EXAMPLES

The following examples are intended to illustrate the present invention and not to limit it thereto.

Example 1

Activity of Compounds of Formula (1) in HCV Replicon Assays

Stable Replicon Cell Reporter Assays

The compounds of the present invention were examined for activity in the inhibition of HCV RNA replication in a cellular assay. The assay demonstrated that the present compounds exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbored an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion ($neo^R$, neomycine phosphotransferase). The construct was bordered by 5' and 3' NTRs (non-translated regions) from HCV type 1b. Continued culture of the replicon cells in the presence of G418 ($neo^R$) was dependent on the replication of the HCV RNA. The stably transfected replicon cells that expressed HCV RNA, which replicated autonomously and to high levels, encoding inter alia luciferase, were used for screening the antiviral compounds.

Cellular Assay Experimental Method:

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures had high luciferase expression in the absence of any inhibitor. The inhibitory activity of the compound on luciferase activity was monitored on the Huh-Luc cells, enabling a dose-response curve for each test compound. EC50 values were then calculated, which value represented the amount of the compound required to decrease by 50% the level of detected luciferase activity, or more specifically, the ability of the genetically linked HCV replicon RNA to replicate.

In the following table, column 1 provides an identification number, column 2 displays the results on the above described Huh7-Luc assay.

| Tibotec ID | Compound Number | HCV Replicon activity (in μM) |
|---|---|---|
| TMC00362059 | 8 | 0.4 |
| TMC00362089 | 20 | 0.7 |
| TMC00362060 | 21 | 0.4 |
| TMC00362100 | 35 | 1.5 |
| TMC00362106 | 39 | 0.4 |
| TMC00362129 | 40 | 7.3 |
| TMC00363359 | 46 | 1.6 |
| TMC0036099 | 47 | 27.7 |
| TMC00362103 | 49 | 13.1 |
| TMC00363366 | 57 | 24.0 |
| TMC00362119 | 58 | 10.3 |
| TMC00362140 | 59 | 2.0 |
| TMC00362101 | 62 | 0.8 |
| TMC00362141 | 69 | 1.8 |
| TMC00363367 | 80 | 5.8 |

The invention claimed is:

1. A method comprising: administering to a subject in need thereof a therapeutically effective amount of a pharmaceutical composition, which inhibits HCV replication, comprising a compound of a formula:

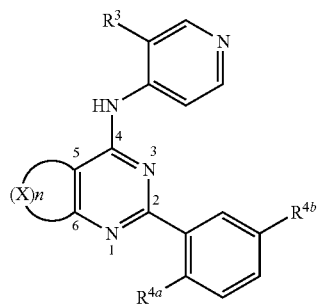
(3)

or a pharmaceutically acceptable salt thereof;

wherein the fused ring bridging positions 5 and 6 of the pyrimidine ring together with the pyrimidine ring forms a group selected from

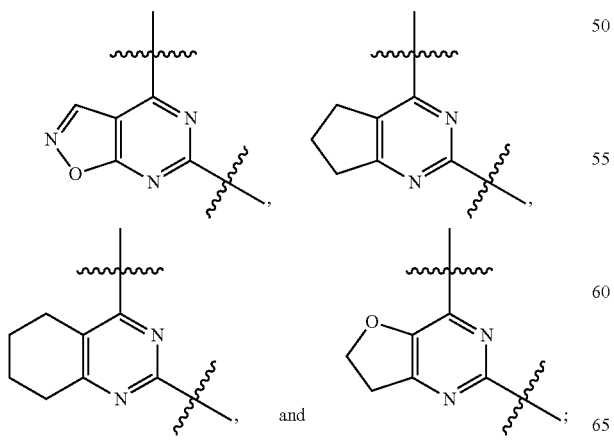

wherein any of these groups may be optionally substituted with one or two alkyl(1-6C);

$R^3$ is hydrogen, alkyl(1-6C), or —CONR$_2$;

each $R^{4a}R^{4b}$ are, independently, hydrogen or halo; and, wherein each R is independently hydrogen, hydroxyl, amino, mono- or dialkyl(1-6C)amino, cycloalkyl(3-7C), Het, or alkyl(1-6C) optionally substituted with one or two substituents selected from hydroxyl, cycloalkyl (3-7C), amino, mono- or dialkyl(1-6C)amino, and Het, wherein said method inhibits HCV replication.

2. The method of claim 1, wherein the compound is

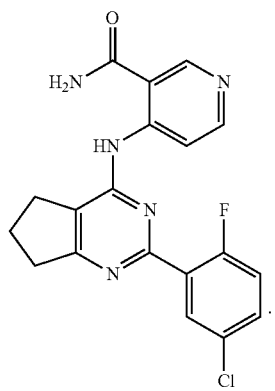

3. The method of claim 1, wherein the compound is

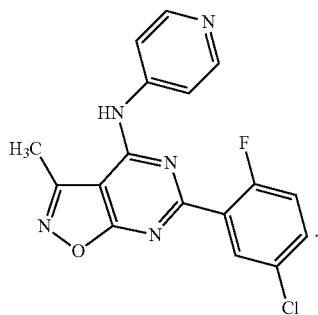

4. The method of claim 1, wherein the compound is

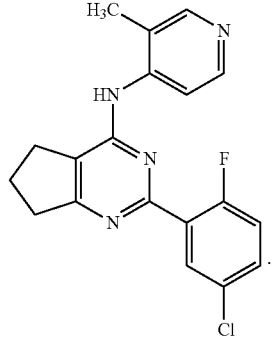

5. The method of claim 1, wherein the compound is
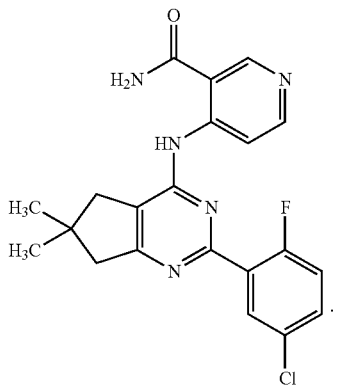
6. The method of claim 1, wherein the compound is
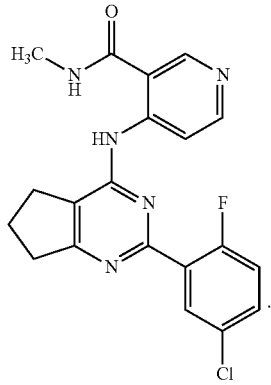
7. The method of claim 1, wherein the compound is
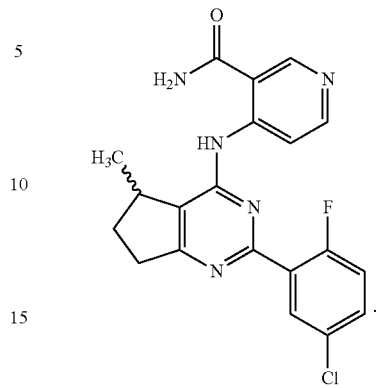
8. The method of claim 1, wherein the compound is
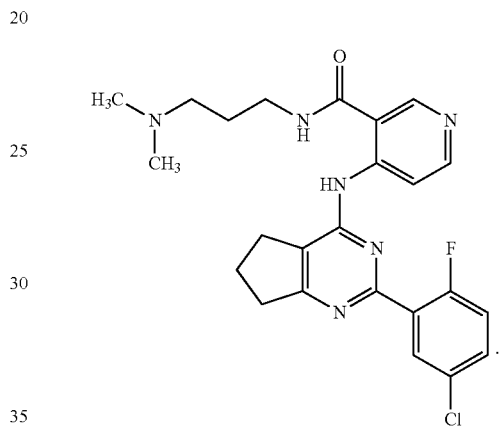
9. The method of claim 1, wherein the subject is a mammal.
\* \* \* \* \*